(12) United States Patent
Tsakraklides et al.

(10) Patent No.: US 10,443,047 B2
(45) Date of Patent: *Oct. 15, 2019

(54) INCREASING CELLULAR LIPID PRODUCTION BY INCREASING THE ACTIVITY OF DIACYLGLYCEROL ACYLTRANSFERASE AND DECREASING THE ACTIVITY OF TRIACYLGLYCEROL LIPASE

(71) Applicant: Novogy, Inc., Cambridge, MA (US)

(72) Inventors: Vasiliki Tsakraklides, Lexington, MA (US); Elena E. Brevnova, Belmont, MA (US)

(73) Assignee: Novogy, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/307,518

(22) PCT Filed: May 1, 2015

(86) PCT No.: PCT/US2015/028760
§ 371 (c)(1),
(2) Date: Oct. 28, 2016

(87) PCT Pub. No.: WO2015/168531
PCT Pub. Date: Nov. 5, 2015

(65) Prior Publication Data
US 2017/0107500 A1     Apr. 20, 2017

Related U.S. Application Data

(60) Provisional application No. 61/987,098, filed on May 1, 2014, provisional application No. 62/090,169, filed on Dec. 10, 2014.

(51) Int. Cl.
| | | |
|---|---|---|
| C12N 15/79 | (2006.01) | |
| C12N 15/81 | (2006.01) | |
| C12N 9/10 | (2006.01) | |
| C12P 7/64 | (2006.01) | |
| C12N 15/80 | (2006.01) | |

(52) U.S. Cl.
CPC ........... *C12N 9/1029* (2013.01); *C12N 15/80* (2013.01); *C12P 7/6463* (2013.01); *C12Y 203/0102* (2013.01); *Y02E 50/13* (2013.01)

(58) Field of Classification Search
None
See application file for complete search history.

(56) References Cited

U.S. PATENT DOCUMENTS

| | | | |
|---|---|---|---|
| 10,260,077 B2 * | 4/2019 | Tsakraklides | ........ C12N 9/1025 |
| 2010/0305341 A1 | 12/2010 | Bailey et al. | |
| 2012/0096588 A1 | 4/2012 | Meyer et al. | |
| 2013/0143282 A1 | 6/2013 | Stephanopoulos et al. | |
| 2013/0149754 A1 | 6/2013 | Dulermo et al. | |

FOREIGN PATENT DOCUMENTS

| | | |
|---|---|---|
| WO | WO 2012/001144 | 1/2012 |
| WO | WO 2013/059649 | 4/2013 |

OTHER PUBLICATIONS

Kurat et al. Obese Yeast. Triglyceride Lipolysis Is Functionally Conserved from Mammals to Yeast. The Journal of Biological Chemistry. vol. 281, No. 1. pp. 491-500.*

Maskow et al. On-line monitoring of lipid storage in yeasts using impedance spectroscopy. 2008. Journal of Biotechnology. vol. 135, pp. 64-70.*

Dulermo et al., "Characterization of the two intracellular lipases of Y. lipolytica encoded by TGL3 and TGL4 genes: new insights into the role of intracellular lipases and lipid body organization," Biochim Biophys Acta, 1831: 1486-1495 (Jul. 2013).

Dulermo et al., "Involvement of the G3P shuttle and Beta-oxidation pathway in the control of TAG synthesis and lipid accumulation in Yarrowia lipolytica," Metab Eng, 13: 482-491 (May 2011).

International Search Report for International Application No. PCT/US2015/028760, dated Sep. 15, 2015.

Tal et al., "Engineering the push and pull of lipid biosynthesis in oleaginous yeast *Yarrowia lipolytica* for biofuel production," Metab Eng, 15:1-9 (Sep. 2012).

Examination Report issued in Australian Patent Application No. 2015252916, dated Feb. 26, 2018.

* cited by examiner

*Primary Examiner* — Channing S Mahatan
(74) *Attorney, Agent, or Firm* — Albert Shung

(57) ABSTRACT

Disclosed are methods and compositions for increasing the triacylglycerol content of a cell by up-regulating diacylglycerol acyltransferase and down-regulating triacylglycerol lipase. In some embodiments, a DGA1 protein is expressed and a native TGL3 gene is knocked out, thereby increasing the synthesis of triacylglycerol and decreasing its consumption, respectively.

13 Claims, 3 Drawing Sheets

Specification includes a Sequence Listing.

SEQUENCE LISTING

<160> NUMBER OF SEQ ID NOS: 88

<210> SEQ ID NO 1
<211> LENGTH: 514
<212> TYPE: PRT
<213> ORGANISM: Yarrowia lipolytica

<400> SEQUENCE: 1

```
Met Thr Ile Asp Ser Gln Tyr Tyr Lys Ser Arg Asp Lys Asn Asp Thr
 1               5                  10                  15

Ala Pro Lys Ile Ala Gly Ile Arg Tyr Ala Pro Leu Ser Thr Pro Leu
            20                  25                  30

Leu Asn Arg Cys Glu Thr Phe Ser Leu Val Trp His Ile Phe Ser Ile
        35                  40                  45

Pro Thr Phe Leu Thr Ile Phe Met Leu Cys Cys Ala Ile Pro Leu Leu
    50                  55                  60

Trp Pro Phe Val Ile Ala Tyr Val Val Tyr Ala Val Lys Asp Asp Ser
65                  70                  75                  80

Pro Ser Asn Gly Gly Val Val Lys Arg Tyr Ser Pro Ile Ser Arg Asn
                85                  90                  95

Phe Phe Ile Trp Lys Leu Phe Gly Arg Tyr Phe Pro Ile Thr Leu His
            100                 105                 110

Lys Thr Val Asp Leu Glu Pro Thr His Thr Tyr Tyr Pro Leu Asp Val
        115                 120                 125

Gln Glu Tyr His Leu Ile Ala Glu Arg Tyr Trp Pro Gln Asn Lys Tyr
    130                 135                 140

Leu Arg Ala Ile Ile Thr Thr Ile Glu Tyr Phe Leu Pro Ala Phe Met
145                 150                 155                 160

Lys Arg Ser Leu Ser Ile Asn Glu Gln Glu Gln Pro Ala Glu Arg Asp
                165                 170                 175

Pro Leu Leu Ser Pro Val Ser Pro Ser Ser Pro Gly Ser Gln Pro Asp
            180                 185                 190

Lys Trp Ile Asn His Asp Ser Arg Tyr Ser Arg Gly Glu Ser Ser Gly
        195                 200                 205

Ser Asn Gly His Ala Ser Gly Ser Glu Leu Asn Gly Asn Gly Asn Asn
    210                 215                 220

Gly Thr Thr Asn Arg Arg Pro Leu Ser Ser Ala Ser Ala Gly Ser Thr
225                 230                 235                 240

Ala Ser Asp Ser Thr Leu Leu Asn Gly Ser Leu Asn Ser Tyr Ala Asn
                245                 250                 255

Gln Ile Ile Gly Glu Asn Asp Pro Gln Leu Ser Pro Thr Lys Leu Lys
            260                 265                 270

Pro Thr Gly Arg Lys Tyr Ile Phe Gly Tyr His Pro His Gly Ile Ile
        275                 280                 285

Gly Met Gly Ala Phe Gly Gly Ile Ala Thr Glu Gly Ala Gly Trp Ser
    290                 295                 300

Lys Leu Phe Pro Gly Ile Pro Val Ser Leu Met Thr Leu Thr Asn Asn
305                 310                 315                 320

Phe Arg Val Pro Leu Tyr Arg Glu Tyr Leu Met Ser Leu Gly Val Ala
                325                 330                 335

Ser Val Ser Lys Lys Ser Cys Lys Ala Leu Leu Lys Arg Asn Gln Ser
            340                 345                 350

Ile Cys Ile Val Val Gly Gly Ala Gln Glu Ser Leu Leu Ala Arg Pro
        355                 360                 365
```

```
Gly Val Met Asp Leu Val Leu Leu Lys Arg Lys Gly Phe Val Arg Leu
    370             375             380

Gly Met Glu Val Gly Asn Val Ala Leu Val Pro Ile Met Ala Phe Gly
385             390             395             400

Glu Asn Asp Leu Tyr Asp Gln Val Ser Asn Asp Lys Ser Ser Lys Leu
            405             410             415

Tyr Arg Phe Gln Gln Phe Val Lys Asn Phe Leu Gly Phe Thr Leu Pro
            420             425             430

Leu Met His Ala Arg Gly Val Phe Asn Tyr Asp Val Gly Leu Val Pro
            435             440             445

Tyr Arg Arg Pro Val Asn Ile Val Val Gly Ser Pro Ile Asp Leu Pro
450             455             460

Tyr Leu Pro His Pro Thr Asp Glu Glu Val Ser Glu Tyr His Asp Arg
465             470             475             480

Tyr Ile Ala Glu Leu Gln Arg Ile Tyr Asn Glu His Lys Asp Glu Tyr
            485             490             495

Phe Ile Asp Trp Thr Glu Glu Gly Lys Gly Ala Pro Glu Phe Arg Met
            500             505             510

Ile Glu

<210> SEQ ID NO 2
<211> LENGTH: 1545
<212> TYPE: DNA
<213> ORGANISM: Yarrowia lipolytica

<400> SEQUENCE: 2
atgactatcg actcacaata ctacaagtcg cgagacaaaa acgacacggc acccaaaatc      60
gcgggaatcc gatatgcccc gctatcgaca ccattactca accgatgtga gaccttctct     120
ctggtctggc acattttcag cattcccact ttcctcacaa ttttcatgct atgctgcgca     180
attccactgc tctggccatt tgtgattgcg tatgtagtgt acgctgttaa agacgactcc     240
ccgtccaacg gaggagtggt caagcgatac tcgcctattt caagaaactt cttcatctgg     300
aagctctttg gccgctactt ccccataact ctgcacaaga cggtggatct ggagcccacg     360
cacacatact accctctgga cgtccaggag tatcacctga ttgctgagag atactggccg     420
cagaacaagt acctccgagc aatcatcacc accatcgagt actttctgcc cgccttcatg     480
aaacggtctc tttctatcaa cgagcaggag cagcctgccg agcagatcc tctcctgtct     540 cccgtttctc ccagctctcc gggttctcaa cctgacaagt ggattaacca cgacagcaga     600
tatagccgtg gagaatcatc tggctccaac ggccacgcct cgggctccga acttaacggc     660
aacggcaaca atggcaccac taaccgacga cctttgtcgt ccgcctctgc tggctccact     720
gcatctgatt ccacgcttct taacgggtcc ctcaactcct acgccaacca gatcattggc     780
gaaaacgacc cacagctgtc gcccacaaaa ctcaagccca ctggcagaaa atacatcttc     840
ggctaccacc cccacggcat tatcggcatg ggagcctttg gtggaattgc accgagggg     900 gctggatggt ccaagctctt tccgggcatc cctgtttctc ttatgactct caccaacaac     960
ttccgagtgc ctctctacag agagtacctc atgagtctgg gagtcgcttc tgtctccaag    1020
aagtcctgca aggccctcct caagcgaaac cagtctatct gcattgtcgt tggtggagca    1080
caggaaagtc ttctggccag acccggtgtc atggacctgg tgctactcaa gcgaaagggt    1140
tttgttcgac ttggtatgga ggtcggaaat gtcgcccttg ttcccatcat ggcctttggt    1200
gagaacgacc tctatgacca ggttagcaac gacaagtcgt ccaagctgta ccgattccag    1260
```

-continued

```
cagtttgtca agaacttcct tggattcacc cttcctttga tgcatgcccg aggcgtcttc    1320
aactacgatg tcggtcttgt ccctacagg cgacccgtca acattgtggt tggttccccc    1380
attgacttgc cttatctccc acacccacc gacgaagaag tgtccgaata ccacgaccga    1440
tacatcgccg agctgcagcg aatctacaac gagcacaagg atgaatattt catcgattgg    1500
accgaggagg gcaaaggagc cccagagttc cgaatgattg agtaa                    1545
```

<210> SEQ ID NO 3
<211> LENGTH: 348
<212> TYPE: PRT
<213> ORGANISM: Rhodosporidium toruloides

<400> SEQUENCE: 3

```
Met Gly Gln Gln Ala Thr Pro Glu Glu Leu Tyr Thr Arg Ser Glu Ile
1               5                   10                  15

Ser Lys Ile Lys Phe Ala Pro Phe Gly Val Pro Arg Ser Arg Arg Leu
            20                  25                  30

Gln Thr Phe Ser Val Phe Ala Trp Thr Thr Ala Leu Pro Ile Leu Leu
        35                  40                  45

Gly Val Phe Phe Leu Leu Cys Ser Phe Pro Pro Leu Trp Pro Ala Val
    50                  55                  60

Ile Ala Tyr Leu Thr Trp Val Phe Phe Ile Asp Gln Ala Pro Ile His
65                  70                  75                  80

Gly Gly Arg Ala Gln Ser Trp Leu Arg Lys Ser Arg Ile Trp Val Trp
                85                  90                  95

Phe Ala Gly Tyr Tyr Pro Val Ser Leu Ile Lys Ser Ala Asp Leu Pro
            100                 105                 110

Pro Asp Arg Lys Tyr Val Phe Gly Tyr His Pro His Gly Val Ile Gly
        115                 120                 125

Met Gly Ala Ile Ala Asn Phe Ala Thr Asp Ala Thr Gly Phe Ser Thr
    130                 135                 140

Leu Phe Pro Gly Leu Asn Pro His Leu Leu Thr Leu Gln Ser Asn Phe
145                 150                 155                 160

Lys Leu Pro Leu Tyr Arg Glu Leu Leu Leu Ala Leu Gly Ile Cys Ser
                165                 170                 175

Val Ser Met Lys Ser Cys Gln Asn Ile Leu Arg Gln Gly Pro Gly Ser
            180                 185                 190

Ala Leu Thr Ile Val Val Gly Gly Ala Ala Glu Ser Leu Ser Ala His
        195                 200                 205

Pro Gly Thr Ala Asp Leu Thr Leu Lys Arg Arg Lys Gly Phe Ile Lys
    210                 215                 220

Leu Ala Ile Arg Gln Gly Ala Asp Leu Val Pro Val Phe Ser Phe Gly
225                 230                 235                 240

Glu Asn Asp Ile Phe Gly Gln Leu Arg Asn Glu Arg Gly Thr Arg Leu
                245                 250                 255

Tyr Lys Leu Gln Lys Arg Phe Gln Gly Val Phe Gly Phe Thr Leu Pro
            260                 265                 270

Leu Phe Tyr Gly Arg Gly Leu Phe Asn Tyr Asn Val Gly Leu Met Pro
        275                 280                 285

Tyr Arg His Pro Ile Val Ser Val Val Gly Arg Pro Ile Ser Val Glu
    290                 295                 300

Gln Lys Asp His Pro Thr Thr Ala Asp Leu Glu Glu Val Gln Ala Arg
305                 310                 315                 320

Tyr Ile Ala Glu Leu Lys Arg Ile Trp Glu Glu Tyr Lys Asp Ala Tyr
```

```
                    325                 330                 335
Ala Lys Ser Arg Thr Arg Glu Leu Asn Ile Ile Ala
            340                 345

<210> SEQ ID NO 4
<211> LENGTH: 1858
<212> TYPE: DNA
<213> ORGANISM: Rhodosporidium toruloides

<400> SEQUENCE: 4
atgggccagc aggcgacgcc cgaggagcta tacacacgct cagagatctc caagatcaag     60
caagtcgagc cagctcttct cctcaccacc ccacaacata ccccgcagcc cacgacagcc    120
ctcccacagc acctgcagcc tgctgaccag ctcgagaaca cccacagatt cgcacccttt    180
ggcgtcccgc ggtcgcgccg gctgcagacc ttctccgtct ttgcctggac gacggcactg    240
cccatcctac tcggcgtctt cttcctcctc tggtgcgtca ggcttggcgt gatctgagag    300
tagcgggcgg atcatctgac ctgcttcttc gctgcagctc gttcccaccg ctctggccgg    360
ctgtcattgc ctacctcacc tgggtctttt tcattgacca ggcgccgatt cacggtggac    420
gggcgcagtc ttggctgcgg aagagtcgga tatgggtctg gtttgcagga tactatcccg    480
tcaggtgcgt cctcttttca agcctgcgtc tcgaggcctc gctcacggcc aactcgcccg    540
accggctacc tccgaacttt ccgtcaacag cttgatcaag gtcagtctgc gcgtctctcg    600
acttcagtgc tctgtggagg agctgcgcca ttgggcccga cctgcggagg gcctcaaagg    660
acgatgccgc tgacttcctt cctccgacag agcgccgacg ttgccgcctg accggaagta    720
cgtctttggc taccaccgc acggcgtcat aggcatgggc gccatcgcca acttcgcgac    780
cgacgcaacc ggcttctcga cactcttccc cggcttgaac cctcacctcc tcaccctcca    840
aagcaacttc aagctcccgc tctaccgcga gttgctgctc gctctcggca tatgctccgt    900
ctcgatgaag agctgtcaga acattctgcg acaaggtgag cggtatgcgc aagacgggcg    960
gtcaagcgtg aacgcagtga acgagaagag ctgaccttcc gccttactcc atccgtgcag   1020
gtcctggctc ggctctcact atcgtcgtcg gtggcgccgc cgagagcttg agtgcgcatc   1080
ccggaaccgc cgatcttacg ctcaagcgac gaaaaggctt catcaaactc gcgatccggc   1140
aaggcgccga ccttgtgccc gtcttttcgt tcggcgagaa cgacgtgcgc acgctctccg   1200
agtctctaaa ccggaagcga atgctgaccg ctgcccaatt ctctctccag atctttggcc   1260
agctgcgaaa cgagcgagga acgcggctgt acaagttgca gaagcgtttc caaggcgtgt   1320
ttggcttcac cctccgtacg tctcaccgcg ccgtcttgcc gaactgctcg ttcagtcgct   1380
cacgcagctt tcactcgcgc agctctcttc tacggccggg gactcttcaa ctgtgcgctc   1440
gagttcaccg cttcgccaac agcgaggaat gcctccgagt acagcccagc tgacgcccca   1500
tctcttctca tagacaacgt cggattgatg ccgtatcgcc atccgatcgt ctctgtcggt   1560
gtgaacccgc tctgtcgctc ctacctgcgt tccttaggct gacaccactc gcgtcaaaca   1620
gtcggtcgac caatctcggt agagcagaag gaccacccga ccacggcgga cctcgaagaa   1680
gttcaggcgc ggtatatcgc agaactcaag cggtacgttc aagtcgtct gcctccgctt    1740 gccgcctcaa ataagctgag gcgtgctgac cgtatctgcc gaaccgtaca gcatctggga   1800
agaatacaag gacgcctacg ccaaaagtcg cacgcgggag ctcaatatta tcgcctga    1858

<210> SEQ ID NO 5
<211> LENGTH: 348
<212> TYPE: PRT
```

<213> ORGANISM: Rhodosporidium toruloides

<400> SEQUENCE: 5

```
Met Gly Gln Gln Ala Thr Pro Glu Glu Leu Tyr Thr Arg Ser Glu Ile
1               5                   10                  15

Ser Lys Ile Lys Phe Ala Pro Phe Gly Val Pro Arg Ser Arg Arg Leu
            20                  25                  30

Gln Thr Phe Ser Val Phe Ala Trp Thr Thr Ala Leu Pro Ile Leu Leu
        35                  40                  45

Gly Val Phe Phe Leu Leu Cys Ser Phe Pro Pro Leu Trp Pro Ala Val
    50                  55                  60

Ile Ala Tyr Leu Thr Trp Val Phe Phe Ile Asp Gln Ala Pro Ile His
65                  70                  75                  80

Gly Gly Arg Ala Gln Ser Trp Leu Arg Lys Ser Arg Ile Trp Val Trp
                85                  90                  95

Phe Ala Gly Tyr Tyr Pro Val Ser Leu Ile Lys Ser Ala Asp Leu Pro
            100                 105                 110

Pro Asp Arg Lys Tyr Val Phe Gly Tyr His Pro His Gly Val Ile Gly
        115                 120                 125

Met Gly Ala Ile Ala Asn Phe Ala Thr Asp Ala Thr Gly Phe Ser Thr
    130                 135                 140

Leu Phe Pro Gly Leu Asn Pro His Leu Leu Thr Leu Gln Ser Asn Phe
145                 150                 155                 160

Lys Leu Pro Leu Tyr Arg Glu Leu Leu Leu Ala Leu Gly Ile Cys Ser
                165                 170                 175

Val Ser Met Lys Ser Cys Gln Asn Ile Leu Arg Gln Gly Pro Gly Ser
            180                 185                 190

Ala Leu Thr Ile Val Val Gly Gly Ala Ala Glu Ser Leu Ser Ala His
        195                 200                 205

Pro Gly Thr Ala Asp Leu Thr Leu Lys Arg Arg Lys Gly Phe Ile Lys
    210                 215                 220

Leu Ala Ile Arg Gln Gly Ala Asp Leu Val Pro Val Phe Ser Phe Gly
225                 230                 235                 240

Glu Asn Asp Ile Phe Gly Gln Leu Arg Asn Glu Arg Gly Thr Arg Leu
                245                 250                 255

Tyr Lys Leu Gln Lys Arg Phe Gln Gly Val Phe Gly Phe Thr Leu Pro
            260                 265                 270

Leu Phe Tyr Gly Arg Gly Leu Phe Asn Tyr Asn Val Gly Leu Met Pro
        275                 280                 285

Tyr Arg His Pro Ile Val Ser Val Val Gly Arg Pro Ile Ser Val Glu
    290                 295                 300

Gln Lys Asp His Pro Thr Thr Ala Asp Leu Glu Glu Val Gln Ala Arg
305                 310                 315                 320

Tyr Ile Ala Glu Leu Lys Arg Ile Trp Glu Glu Tyr Lys Asp Ala Tyr
                325                 330                 335

Ala Lys Ser Arg Thr Arg Glu Leu Asn Ile Ile Ala
            340                 345
```

<210> SEQ ID NO 6
<211> LENGTH: 1047
<212> TYPE: DNA
<213> ORGANISM: Rhodosporidium toruloides

<400> SEQUENCE: 6
atgggccagc aggcgacgcc cgaggagcta tacacacgct cagagatctc caagatcaag        60

```
ttcgcaccct tggcgtccc gcggtcgcgc cggctgcaga ccttctccgt ctttgcctgg    120
acgacggcac tgcccatcct actcggcgtc ttcttcctcc tctgctcgtt cccaccgctc    180
tggccggctg tcattgccta cctcacctgg gtctttttca ttgaccaggc gccgattcac    240
ggtgacgggc cgcagtcttg gctgcggaag agtcggatat gggtctggtt tgcaggatac    300
tatcccgtca gcttgatcaa gagcgccgac ttgccgcctg accggaagta cgtctttggc    360
taccacccgc acggcgtcat aggcatgggc gccatcgcca acttcgcgac cgacgcaacc    420
ggcttctcga cactcttccc cggcttgaac cctcacctcc tcaccctcca aagcaacttc    480
aagctcccgc tctaccgcga gttgctgctc gctctcggca tatgctccgt ctcgatgaag    540
agctgtcaga acattctgcg acaaggtcct ggctcggctc tcactatcgt cgtcggtggc    600
gccgccgaga gcttgagtgc gcatcccgga accgccgatc ttacgctcaa gcacgaaaaa    660
ggcttcatca aactcgcgat ccggcaaggc gccgaccttg tgcccgtctt ttcgttcggc    720
gagaacgaca tctttggcca gctgcgaaac gagcgaggaa cgcggctgta caagttgcag    780
aagcgtttcc aaggcgtgtt tggcttcacc ctccctctct tctacggccg gggactcttc    840
aactacaacg tcggattgat gccgtatcgc catccgatcg tctctgtcgt cggtcgacca    900
atctcggtag agcagaagga ccacccgacc acggcggacc tcgaagaagt tcaggcgcgg    960
tatatcgcag aactcaagcg gatctgggaa gaatacaagg acgcctacgc caaaagtcgc   1020
acgcgggagc tcaatattat cgcctga                                       1047
```

<210> SEQ ID NO 7
<211> LENGTH: 348
<212> TYPE: PRT
<213> ORGANISM: Rhodosporidium toruloides

<400> SEQUENCE: 7

```
Met Gly Gln Gln Ala Thr Pro Glu Glu Leu Tyr Thr Arg Ser Glu Ile
1               5                   10                  15

Ser Lys Ile Lys Phe Ala Pro Phe Gly Val Pro Arg Ser Arg Arg Leu
            20                  25                  30

Gln Thr Phe Ser Val Phe Ala Trp Thr Thr Ala Leu Pro Ile Leu Leu
        35                  40                  45

Gly Val Phe Phe Leu Leu Cys Ser Phe Pro Pro Leu Trp Pro Ala Val
    50                  55                  60

Ile Ala Tyr Leu Thr Trp Val Phe Phe Ile Asp Gln Ala Pro Ile His
65                  70                  75                  80

Gly Gly Arg Ala Gln Ser Trp Leu Arg Lys Ser Arg Ile Trp Val Trp
                85                  90                  95

Phe Ala Gly Tyr Tyr Pro Val Ser Leu Ile Lys Ser Ala Asp Leu Pro
            100                 105                 110

Pro Asp Arg Lys Tyr Val Phe Gly Tyr His Pro His Gly Val Ile Gly
        115                 120                 125

Met Gly Ala Ile Ala Asn Phe Ala Thr Asp Ala Thr Gly Phe Ser Thr
    130                 135                 140

Leu Phe Pro Gly Leu Asn Pro His Leu Leu Thr Leu Gln Ser Asn Phe
145                 150                 155                 160

Lys Leu Pro Leu Tyr Arg Glu Leu Leu Leu Ala Leu Gly Ile Cys Ser
                165                 170                 175

Val Ser Met Lys Ser Cys Gln Asn Ile Leu Arg Gln Gly Pro Gly Ser
            180                 185                 190
```

Ala Leu Thr Ile Val Val Gly Gly Ala Ala Glu Ser Leu Ser Ala His
195                 200                 205

Pro Gly Thr Ala Asp Leu Thr Leu Lys Arg Arg Lys Gly Phe Ile Lys
210                 215                 220

Leu Ala Ile Arg Gln Gly Ala Asp Leu Val Pro Val Phe Ser Phe Gly
225                 230                 235                 240

Glu Asn Asp Ile Phe Gly Gln Leu Arg Asn Glu Arg Gly Thr Arg Leu
            245                 250                 255

Tyr Lys Leu Gln Lys Arg Phe Gln Val Phe Gly Phe Thr Leu Pro
        260                 265                 270

Leu Phe Tyr Gly Arg Gly Leu Phe Asn Tyr Asn Val Gly Leu Met Pro
    275                 280                 285

Tyr Arg His Pro Ile Val Ser Val Gly Arg Pro Ile Ser Val Glu
290                 295                 300

Gln Lys Asp His Pro Thr Thr Ala Asp Leu Glu Glu Val Gln Ala Arg
305                 310                 315                 320

Tyr Ile Ala Glu Leu Lys Arg Ile Trp Glu Gly Tyr Lys Asp Ala Tyr
                325                 330                 335

Ala Lys Ser Arg Thr Arg Glu Leu Asn Ile Ile Ala
            340                 345

<210> SEQ ID NO 8
<211> LENGTH: 1047
<212> TYPE: DNA
<213> ORGANISM: Rhodosporidium toruloides

<400> SEQUENCE: 8

```
atgggacagc aggctacccc cgaggagctc tacacccgat ccgagatttc taagattaag      60
ttcgcccctt ttggagtgcc ccgatcccga cgactccaga ccttctccgt ttttgcctgg     120
accactgctc tgcccattct gctcggcgtc ttctttctgc tctgctcttt cccccctctc     180
tggccccgcg tcatcgctta cctgacctgg gtgttcttta cgaccaggc ccctattcac      240
ggcggtcgag ctcagtcctg gctgcgaaag tctcgaattt gggtttggtt cgccggttac     300
tacccccgtct ctctcatcaa gtcggctgac ctgccccctg atcgaaagta cgtgttcggc    360
taccacccctc atggtgttat cggtatggga gccattgcta actttgccac cgatgctact    420
ggtttctcca ccctctttcc cggactgaac cctcacctgc tcactctcca gtctaacttc    480
aagctccccc tgtaccgaga gctgctcctg gccctgggta tctgctccgt ctctatgaag    540
tcttgtcaga acattctccg acagggacct ggttcggctc tgaccatcgt cgtgggagga    600
gctgctgagt cgctctccgc ccatcctgga accgctgacc tcactctgaa gcgacgaaag    660
ggcttcatca gctcgccat cgacagggt gctgacctgg tgcccgtttt ctcctttgga     720
gagaacgata ttttcggcca gctgcgaaac gagcgaggaa cccgactcta caagctgcag    780
aagcgatttc agggtgtgtt cggcttcacc ctccctctgt tctacggacg aggcctcttt    840
aactacaacg ttggactgat gccctaccga cacctatcg tctcggttgt cggccgaccc      900
atttccgtgg agcagaagga ccatcctacc actgccgatc tcgaggaggt gcaggcccga    960
tacatcgctg agctgaagcg aatttgggag gagtacaagg acgcctacgc taagtctcga   1020
acccgagagc tgaacatcat tgcctaa                                        1047
```

<210> SEQ ID NO 9
<211> LENGTH: 410
<212> TYPE: PRT
<213> ORGANISM: Lipomyces starkeyi

<400> SEQUENCE: 9

```
Met Ser Glu Lys Ala Glu Ile Glu Val Pro Pro Gln Lys Ser Thr Phe
1               5                   10                  15
Pro Arg Ser Val His Phe Ala Pro Leu His Ile Pro Leu Glu Arg Arg
            20                  25                  30
Leu Gln Thr Leu Ala Val Leu Phe His Thr Val Ala Leu Pro Tyr Cys
        35                  40                  45
Ile Gly Leu Phe Phe Leu Met Leu Ala Phe Pro Pro Phe Trp Pro Leu
50                  55                  60
Leu Val Met Tyr Val Ile Tyr Ala Tyr Gly Phe Asp His Ser Ser Ser
65                  70                  75                  80
Asn Gly Glu Ile Ser Arg Arg Ser Pro Leu Phe Arg Arg Leu Pro
                85                  90                  95
Leu Phe Arg Leu Tyr Cys Asp Tyr Phe Pro Ile His Ile His Arg Glu
            100                 105                 110
Val Pro Leu Glu Pro Thr Phe Pro Gly Arg Leu Arg Glu Pro Ser Gly
        115                 120                 125
Leu Val Glu Arg Trp Ile Ala Lys Met Phe Gly Val Gln Asp Ala Val
130                 135                 140
Val Glu Gly Asn Glu Ser Asp Val Lys Ala Thr Ala Asn Gly Asn Gly
145                 150                 155                 160
Thr Thr Lys Glu Ile Gly Pro Thr Tyr Val Phe Gly Tyr His Pro His
                165                 170                 175
Gly Ile Val Ser Leu Gly Ala Phe Gly Ala Ile Gly Thr Glu Gly Ala
            180                 185                 190
Gly Trp Glu Lys Leu Phe Pro Gly Ile Pro Val Ser Leu Leu Thr Leu
        195                 200                 205
Glu Thr Asn Phe Ser Leu Pro Phe Tyr Arg Glu Tyr Leu Leu Ser Leu
210                 215                 220
Gly Ile Ala Ser Val Ser Arg Arg Ser Cys Thr Asn Leu Leu Lys His
225                 230                 235                 240
Asp Gln Ser Ile Cys Ile Val Ile Gly Gly Ala Gln Glu Ser Leu Leu
                245                 250                 255
Ala Glu Pro Gly Thr Leu Asp Leu Ile Leu Val Lys Arg Arg Gly Phe
            260                 265                 270
Val Lys Leu Ala Met Ser Thr Ala Arg Val Ser Asp Gln Pro Ile Cys
        275                 280                 285
Leu Val Pro Ile Leu Ser Phe Gly Glu Asn Asp Val Tyr Asp Gln Val
290                 295                 300
Arg Gly Asp Arg Ser Ser Lys Leu Tyr Lys Ile Gln Thr Phe Ile Lys
305                 310                 315                 320
Lys Ala Ala Gly Phe Thr Leu Pro Leu Met Tyr Ala Arg Gly Ile Phe
                325                 330                 335
Asn Tyr Asp Phe Gly Leu Met Pro Tyr Arg Arg Gln Met Thr Leu Val
            340                 345                 350
Val Gly Lys Pro Ile Ala Val Pro Tyr Val Ala Gln Pro Thr Glu Ala
        355                 360                 365
Glu Ile Glu Val Tyr His Lys Gln Tyr Met Asp Glu Leu Arg Arg Leu
370                 375                 380
Trp Asp Thr Tyr Lys Asp Asp Tyr Phe Val Asp His Lys Gly Lys Gly
385                 390                 395                 400
Val Lys Asn Ser Glu Met Arg Phe Val Glu
```

<210> SEQ ID NO 10
<211> LENGTH: 1233
<212> TYPE: DNA
<213> ORGANISM: Lipomyces starkeyi

<400> SEQUENCE: 10

```
atgagtgaga aggcagagat cgaggttccg ccgcaaaaat cgacattccc tcgcagtgtg        60
cacttcgctc cacttcatat tccactggag agacgcctac agactttggc agtcttattc       120
cacactgtcg cgctaccata ctgcatcggt ctgttctttc tcatgctcgc gttccctcct       180
ttttggccat tattggtaat gtatgtcata tacgcatacg ggttcgacca ctcgagctcg       240
aacggagaga tctcccgccg gcgatcgccg ctgtttcgaa gactcccgtt gttcaggctg       300
tattgtgatt acttccccat ccacattcac cgggaggttc cgctcgagcc gacgtttcct       360
ggtcgccttc gcgaaccgag tggccttgtc gagcggtgga ttgcgaagat gttcggcgtg       420
caggacgctg ttgtcgaggg aaatgaatct gacgttaagg ccacgccaa cggcaatggg        480
acgacgaaag aaatcggacc gacgtatgtt ttcggctatc atccgcatgg aattgttagc       540
ttgggtgcgt ttggtgctat tggtacgaa ggcgctggat gggagaagct ctttcctggg        600
atcccggtgt cactgctgac tctcgaaaca aatttcagcc ttccatttta cagagagtat       660
ttgctgtcac ttgggattgc ttcagtatct cgacggtctt gtaccaatct cctcaaacac       720
gaccaatcca tctgcatcgt tatcggcggc gcccaagagt cgctcttagc ggaaccaggc       780
actctagatc tgatcctcgt taaacgtcgc ggttttgtca aacttgcaat gtcaacggcg       840
cgggtatctg accaaccgat ttgtcttgtt ccgatcctca gtttcggcga aacgacgtg        900
tacgaccaag tccgcgggga ccgatcgtcg aagttgtata agatccagac ttttatcaag       960
aaagcggccg ggtttacgct accattgatg tatgcgcgcg gtatatttaa ttacgacttt      1020
gggctgatgc cgtaccgcag gcaaatgacg ctcgtggtcg gcaagccgat tgcagtgccg      1080
tacgtggccc agcctacgga ggctgaaatc gaagtgtatc acaagcagta catggatgaa      1140
ttgaggaggt tatgggacac gtataaggac gactattttg tagaccacaa gggcaagggg      1200
gtcaagaatt ccgagatgcg ttttgtggag taa                                   1233
```

<210> SEQ ID NO 11
<211> LENGTH: 410
<212> TYPE: PRT
<213> ORGANISM: Lipomyces starkeyi

<400> SEQUENCE: 11

```
Met Ser Glu Lys Ala Glu Ile Glu Val Pro Pro Gln Lys Ser Thr Phe
  1               5                  10                  15

Pro Arg Ser Val His Phe Ala Pro Leu His Ile Pro Leu Glu Arg Arg
             20                  25                  30

Leu Gln Thr Leu Ala Val Leu Phe His Thr Val Ala Leu Pro Tyr Cys
         35                  40                  45

Ile Gly Leu Phe Phe Leu Met Leu Ala Phe Pro Pro Phe Trp Pro Leu
     50                  55                  60

Leu Val Met Tyr Val Ile Tyr Ala Tyr Gly Phe Asp His Ser Ser Ser
 65                  70                  75                  80

Asn Gly Glu Ile Ser Arg Arg Arg Ser Pro Leu Phe Arg Arg Leu Pro
                 85                  90                  95

Leu Phe Arg Leu Tyr Cys Asp Tyr Phe Pro Ile His Ile His Arg Glu
```

```
                  100                 105                 110
Val Pro Leu Glu Pro Thr Phe Pro Gly Arg Leu Arg Glu Pro Ser Gly
            115                 120                 125

Leu Val Glu Arg Trp Ile Ala Lys Met Phe Gly Val Gln Asp Ala Val
        130                 135                 140

Val Glu Gly Asn Glu Ser Asp Val Lys Ala Thr Ala Asn Gly Asn Gly
145                 150                 155                 160

Thr Thr Lys Glu Ile Gly Pro Thr Tyr Val Phe Gly Tyr His Pro His
                165                 170                 175

Gly Ile Val Ser Leu Gly Ala Phe Gly Ala Ile Gly Thr Glu Gly Ala
            180                 185                 190

Gly Trp Glu Lys Leu Phe Pro Gly Ile Pro Val Ser Leu Leu Thr Leu
        195                 200                 205

Glu Thr Asn Phe Ser Leu Pro Phe Tyr Arg Glu Tyr Leu Leu Ser Leu
    210                 215                 220

Gly Ile Ala Ser Val Ser Arg Arg Ser Cys Thr Asn Leu Leu Lys His
225                 230                 235                 240

Asp Gln Ser Ile Cys Ile Val Ile Gly Gly Ala Gln Glu Ser Leu Leu
                245                 250                 255

Ala Glu Pro Gly Thr Leu Asp Leu Ile Leu Val Lys Arg Arg Gly Phe
            260                 265                 270

Val Lys Leu Ala Met Ser Thr Ala Arg Val Ser Asp Gln Pro Ile Cys
        275                 280                 285

Leu Val Pro Ile Leu Ser Phe Gly Glu Asn Asp Val Tyr Asp Gln Val
    290                 295                 300

Arg Gly Asp Arg Ser Ser Lys Leu Tyr Lys Ile Gln Thr Phe Ile Lys
305                 310                 315                 320

Lys Ala Ala Gly Phe Thr Leu Pro Leu Met Tyr Ala Arg Gly Ile Phe
                325                 330                 335

Asn Tyr Asp Phe Gly Leu Met Pro Tyr Arg Arg Gln Met Thr Leu Val
            340                 345                 350

Val Gly Lys Pro Ile Ala Val Pro Tyr Val Ala Gln Pro Thr Glu Ala
        355                 360                 365

Glu Ile Glu Val Tyr His Lys Gln Tyr Met Asp Glu Leu Arg Arg Leu
    370                 375                 380

Trp Asp Thr Tyr Lys Asp Asp Tyr Phe Val Asp His Lys Gly Lys Gly
385                 390                 395                 400

Val Lys Asn Ser Glu Met Arg Phe Val Glu
                405                 410

<210> SEQ ID NO 12
<211> LENGTH: 1233
<212> TYPE: DNA
<213> ORGANISM: Lipomyces starkeyi

<400> SEQUENCE: 12
atgtccgaga aggctgagat tgaggtgccc ccccagaagt ctactttccc tcgatccgtt      60
catttcgccc cctgcatat cccctggag cgacgactcc agaccctggc tgtgctcttc       120
cacactgttg ccctgcctta ctgcatcgga ctcttctttc tgatgctcgc tttcccccct    180
ttttggcccc tgctcgtgat gtacgttatc tacgcctacg gattcgacca ttcctcttcg    240
aacggcgaga tctctcgacg acgatcgcct ctgttccgac gactgcccct ctttcgactc    300
tactgtgatt acttccctat ccacattcat cgagaggtcc ccctggagcc taccttttcct  360
```

```
ggtcgactgc gagagccttc cggactcgtt gagcgatgga ttgctaagat gttcggtgtc      420
caggacgccg tcgtggaggg aaacgagtct gatgtgaagg ccaccgctaa cggaaacggc      480
accactaagg agatcggccc tacttacgtc ttcggatacc accccatgg cattgtgtcc       540 ctgggagcct ttggcgctat cggtaccgag ggtgctggat gggagaagct cttccctggt      600
attcccgtct cgctgctcac cctggagact aacttctccc tccccttta ccgagagtac       660 ctgctctctc tgggaatcgc ctcggtgtcc cgacgatcgt gcaccaacct gctcaagcac      720
gaccagtcta tctgtattgt tatcggaggt gctcaggagt ccctgctcgc tgagcctgga      780
accctggacc tcattctggt caagcgacga ggcttcgtga agctggccat gtccactgct      840
cgagtgtctg atcagcctat ttgcctggtt cccatcctct ctttcggcga aacgacgtt      900 tacgatcagg tccgaggtga ccgatcctct aagctgtaca agattcagac cttcatcaag      960
aaggccgctg gctttactct ccctctgatg tacgcccgag gcatcttcaa ctacgacttt     1020
ggtctgatgc cctaccgacg acagatgacc ctcgttgtcg gcaagcctat tgccgtcccc     1080
tacgtggctc agcccactga ggccgagatc gaggtctacc acaagcagta catggacgag     1140
ctgcgacgac tctgggatac ctacaaggac gattacttcg ttgaccataa gggcaagggt     1200
gtcaagaact ctgagatgcg atttgtggag taa                                  1233
```

<210> SEQ ID NO 13
<211> LENGTH: 380
<212> TYPE: PRT
<213> ORGANISM: Aspergillus terreus

<400> SEQUENCE: 13

```
Met Pro Arg Asn Thr His Pro Pro Ala Asn Asn Ala Gly Pro Asn Ala
1               5                   10                  15

Ser His Lys Lys Asp Arg Lys Arg Gln Gly Arg Leu Phe Gln His Thr
            20                  25                  30

Val Pro Asn Lys Tyr Ser Arg Ile Arg Trp Ala Pro Leu Asn Ile Gly
        35                  40                  45

Leu Glu Arg Arg Leu Gln Thr Leu Val Val Leu Cys His Thr Leu Thr
    50                  55                  60

Ile Ala Leu Phe Leu Ala Phe Phe Phe Thr Cys Ala Ile Pro Leu
65                  70                  75                  80

Thr Trp Pro Leu Leu Phe Pro Tyr Leu Val Tyr Ile Thr Leu Phe Ser
                85                  90                  95

Thr Ala Pro Thr Ser Gly Thr Leu Lys Gly Arg Ser Asp Phe Leu Arg
            100                 105                 110

Ser Leu Pro Ile Trp Lys Leu Tyr Thr Ala Tyr Phe Pro Ala Lys Leu
        115                 120                 125

His Arg Ser Glu Pro Leu Leu Pro Thr Arg Lys Tyr Ile Phe Gly Tyr
    130                 135                 140

His Pro His Gly Ile Ile Ser His Gly Ala Phe Ala Ala Phe Ala Thr
145                 150                 155                 160

Asp Ala Leu Gly Phe Ser Lys Leu Phe Pro Gly Ile Thr Asn Thr Leu
                165                 170                 175

Leu Thr Leu Asp Ser Asn Phe Arg Ile Pro Phe Tyr Arg Glu Tyr Ala
            180                 185                 190

Met Ala Met Gly Val Ala Ser Val Ser Arg Glu Ser Cys Glu Asn Leu
        195                 200                 205

Leu Thr Lys Gly Gly Ala Asp Gly Glu Gly Met Gly Arg Ala Ile Thr
    210                 215                 220
```

```
Ile Val Val Gly Gly Ala Arg Glu Ser Leu Asp Ala Leu Pro His Thr
225                 230                 235                 240

Met Arg Leu Val Leu Lys Arg Lys Gly Phe Ile Lys Leu Ala Ile
                245                 250                 255

Arg Thr Gly Ala Asp Leu Val Pro Val Leu Ala Phe Gly Glu Asn Asp
                260                 265                 270

Leu Tyr Glu Gln Val Arg Ser Asp Gln His Pro Leu Ile Tyr Lys Val
            275                 280                 285

Gln Met Leu Val Lys Arg Phe Leu Gly Phe Thr Val Pro Leu Phe His
        290                 295                 300

Ala Arg Gly Ile Phe Asn Tyr Asp Val Gly Leu Met Pro Tyr Arg Arg
305                 310                 315                 320

Pro Leu Asn Ile Val Val Gly Arg Pro Ile Gln Val Val Arg Gln Gln
                325                 330                 335

Asp Arg Asp Lys Ile Asp Asp Glu Tyr Ile Asp Arg Leu His Ala Glu
                340                 345                 350

Tyr Val Arg Glu Leu Glu Ser Leu Trp Asp Gln Trp Lys Asp Val Tyr
            355                 360                 365

Ala Lys Asp Arg Ile Ser Glu Leu Glu Ile Val Ala
370                 375                 380

<210> SEQ ID NO 14
<211> LENGTH: 1143
<212> TYPE: DNA
<213> ORGANISM: Aspergillus terreus

<400> SEQUENCE: 14
atgccccgaa acacccaccc ccccgccaac aacgccggac ctaacgcctc tcacaagaag      60
gaccgaaagc gacagggacg actctttcag cacaccgttc ctaacaagta ctctcgaatc     120
cgatgggccc ccctcaacat tggcctggag cgacgactgc agaccctcgt cgtgctgtgc     180
cataccctca ctatcgccct gttcctcgct ttcttttttct ttacttgtgc cattcccctg    240
acctggcctc tgctcttccc ctacctcgtg tacatcaccc tgttttcgac cgctcctact    300
tccggtaccc tgaagggacg atctgacttc ctccgatcgc tgcctatttg aagctctac    360 actgcctact ttcccgctaa gctgcaccga tccgagcctc tgctccctac ccgaaagtac    420
atcttcggct accaccccca tggtatcatt cccatggag ccttcgccgc ttttgccact    480
gacgctctcg gcttctctaa gctgtttcct ggtatcacca acactctgct cacccctggat   540 tcgaacttcc gaattccctt ttaccgagag tacgccatgg ctatgggagt ggcttccgtt    600
tctcgagagt cgtgcgagaa cctgctcact aagggaggtg ctgacggaga gggaatgggc    660
cgagctatca ccattgttgt cggaggcgcc cgagagtccc tcgatgctct gcctcacact    720
atgcgactgg tcctcaagcg acgaaagggt ttcatcaagc tggccattcg aaccggagct    780
gacctcgttc ccgtcctggc cttcggcgag aacgacctct acgagcaggt gcgatctgat    840
cagcacccct gatctacaa ggtccagatg ctcgtgaagc gattcctggg ttttaccgtg     900
cccctgttcc atgctcgagg aattttttaac tacgacgttg gcctcatgcc ttaccgacga    960
cccctgaaca tcgtggttgg tcgacccatt caggtcgtgc gacagcagga ccgagataag   1020
atcgacgatg agtacattga ccgactccac gccgagtacg tccgagagct cgagtccctg   1080
tgggaccagt ggaaggatgt ttacgccaag gaccgaatct ctgagctgga gattgtcgct   1140
taa                                                                 1143
```

<210> SEQ ID NO 15
<211> LENGTH: 437
<212> TYPE: PRT
<213> ORGANISM: Claviceps purpurea

<400> SEQUENCE: 15

```
Met Ala Ala Val Gln Val Ala Arg Pro Val Pro Pro His His His Asp
1               5                   10                  15

Gly Ala Gly Arg Glu His Lys Gly Glu Arg Ala His Ser Pro Glu Arg
            20                  25                  30

Gly Glu Lys Thr Val His Asn Gly Tyr Gly Leu Ala Glu Thr His Glu
        35                  40                  45

Pro Leu Glu Leu Asn Gly Ser Ala Val Gln Asp Gly Lys His Asp Ser
    50                  55                  60

Asp Glu Thr Ile Thr Asn Gly Asp Tyr Ser Pro Tyr Pro Glu Leu Asp
65                  70                  75                  80

Cys Gly Lys Glu Arg Ala Ala His Glu Lys Glu Ala Trp Thr Ala Gly
                85                  90                  95

Gly Val Arg Phe Ala Pro Leu Arg Val Pro Phe Lys Arg Arg Met Gln
            100                 105                 110

Thr Ala Ala Val Leu Phe His Cys Met Ser Ile Ile Leu Ile Ser Ser
        115                 120                 125

Cys Phe Trp Phe Ser Leu Ala Asn Pro Ile Thr Trp Pro Ile Leu Val
    130                 135                 140

Pro Tyr Leu Val His Leu Ser Leu Ser Asn Ala Ser Thr Asp Gly Lys
145                 150                 155                 160

Leu Ser Tyr Arg Ser Glu Trp Leu Arg Ser Leu Pro Leu Trp Arg Leu
                165                 170                 175

Phe Ala Gly Tyr Phe Pro Ala Lys Leu His Lys Thr Phe Asp Leu Pro
            180                 185                 190

Pro Asn Arg Lys Tyr Ile Phe Gly Tyr His Pro His Gly Ile Ile Ser
        195                 200                 205

His Gly Ala Trp Cys Ala Phe Ala Thr Asn Ala Leu Gly Phe Val Glu
    210                 215                 220

Lys Phe Pro Gly Ile Thr Asn Ser Leu Leu Thr Leu Asp Ser Asn Phe
225                 230                 235                 240

Arg Val Pro Phe Tyr Arg Asp Trp Ile Leu Ala Met Gly Ile Arg Ser
                245                 250                 255

Val Ser Arg Glu Ser Ile Arg Asn Ile Leu Ser Lys Gly Gly Pro Asp
            260                 265                 270

Ser Asn Gly Gln Gly Arg Ala Val Thr Ile Val Ile Gly Gly Ala Arg
        275                 280                 285

Glu Ser Leu Glu Ala Gln Pro Gly Thr Leu Arg Leu Ile Leu Gln Gly
    290                 295                 300

Arg Lys Gly Phe Ile Lys Val Ala Leu Arg Ala Gly Ala Asp Leu Val
305                 310                 315                 320

Pro Val Ile Gly Phe Gly Glu Asn Asp Leu Tyr Asp Gln Leu Ser Pro
                325                 330                 335

Lys Thr His Pro Leu Val His Lys Ile Gln Met Phe Phe Leu Lys Val
            340                 345                 350

Phe Lys Phe Thr Ile Pro Ala Leu His Gly Arg Gly Leu Leu Asn Tyr
        355                 360                 365

Asp Val Gly Leu Leu Pro Tyr Arg Arg Ala Val Asn Ile Val Val Gly
    370                 375                 380
```

Arg Pro Ile Gln Ile Asp Glu Thr Tyr Gly Glu Gln Pro Gln Glu
385                 390                 395                 400

Val Ile Asp Arg Tyr His Glu Leu Tyr Val Gln Val Glu Arg Leu
            405                 410                 415

Tyr Ala Ala Tyr Lys Glu Gln Phe Ser Asn Gly Lys Lys Thr Pro Glu
        420                 425                 430

Leu Gln Ile Leu Ser
        435

<210> SEQ ID NO 16
<211> LENGTH: 1314
<212> TYPE: DNA
<213> ORGANISM: Claviceps purpurea

<400> SEQUENCE: 16
atggctgctg ttcaggttgc ccgacccgtt ccccccacc accacgatgg cgctggccga      60
gagcacaagg gagagcgagc ccattcccct gagcgaggag agaagaccgt ccacaacggc    120
tacggtctgg ccgagactca tgagccctg gagctcaacg ttctgctgt gcaggacgga     180 aagcacgact cggatgagac catcactaac ggtgactact ctccctaccc tgagctcgat    240
tgcggaaagg agcgagccgc tcatgagaag gaggcttgga ccgctggagg tgtgcgattc    300
gctcctctgc gagttccttt taagcgacga atgcagactg ccgctgtcct cttccactgc 360
atgtccatca ttctgatttc ctcttgtttc tggttttctc tcgccaaccc catcacctgg 420
cctattctcg ttccctacct ggtccacctg tcgctctcca acgcttctac tgacggcaag 480
ctctcctacc gatctgagtg gctgcgatcc ctgcctctct ggcgactgtt cgccggttac 540
tttcccgcta agctccacaa gaccttcgat ctgcccccta accgaaagta catctttggt 600
taccaccccc atggaatcat ttcccatggc gcctggtgtg ccttcgctac caacgctctg 660
ggcttcgttg agaagtttcc tggtattacc aactcgctgc tcactctcga ctccaacttc 720
cgagtgccct tttaccgaga ttggatcctg gccatgggca ttcgatctgt ttcgcgagag 780
tctatccgaa acattctctc gaagggagga cctgactcca acggacaggg ccgagctgtg 840
accatcgtta ttggtggagc ccgagagtct ctggaggctc agcccggaac tctgcgactc 900
attctgcagg gccgaaaggg cttcattaag gtggctctcc gagctggagc tgacctggtt 960
cccgtcatcg gtttcggaga gaacgacctc tacgatcagc tgtcccctaa gacccacccc 1020
ctcgttcata agatccagat gttctttctg aaggtcttca agtttactat tcctgctctg 1080
cacggacgag gtctgctcaa ctacgacgtc ggtctgctcc cttaccgacg agctgtgaac 1140
atcgtcgtgg gacgacccat ccagattgac gagacctacg gcgagcagcc ccctcaggag 1200
gtcatcgatc gataccacga gctctacgtc caggaggtgg agcgactgta cgccgcttac 1260
aaggagcagt tctcgaacgg aaagaagacc cccgagctcc agatcctgtc ctaa 1314

<210> SEQ ID NO 17
<211> LENGTH: 351
<212> TYPE: PRT
<213> ORGANISM: Aurantiochytrium limacinum

<400> SEQUENCE: 17

Met Leu Ala Trp Met Pro Val Leu Ile Ala Leu Pro Arg Arg Lys Gln
1 5 10 15

Thr Ala Val Val Leu Leu Phe Val Met Leu Leu Pro Met Ile Met Val
20 25 30

```
Val Tyr Ser Trp Thr Leu Ile Leu Ile Phe Pro Leu Thr Thr Leu
         35                  40                  45
Pro Thr Leu Ser Tyr Leu Ile Trp Ile Met Tyr Ile Asp Lys Ser His
 50                  55                  60
Glu Thr Gly Lys Arg Lys Pro Phe Met Arg Tyr Trp Lys Met Trp Arg
 65                  70                  75                  80
His Phe Ala Asn Tyr Phe Pro Leu Arg Leu Ile Arg Thr Thr Pro Leu
                 85                  90                  95
Asp Pro Arg Arg Lys Tyr Val Phe Cys Tyr His Pro His Gly Ile Ile
                100                 105                 110
Ser Leu Gly Ala Phe Gly Asn Phe Ala Thr Asp Ser Thr Gly Phe Ser
            115                 120                 125
Arg Lys Phe Pro Gly Ile Asp Leu Arg Leu Leu Thr Leu Gln Ile Asn
        130                 135                 140
Phe Tyr Cys Pro Ile Ile Arg Glu Leu Leu Leu Tyr Met Gly Leu Cys
145                 150                 155                 160
Ser Ala Ala Lys Lys Ser Cys Asn Gln Ile Leu Gln Arg Gly Pro Gly
                165                 170                 175
Ser Ala Ile Met Leu Val Val Gly Gly Ala Ala Glu Ser Leu Asp Ser
            180                 185                 190
Gln Pro Gly Thr Tyr Arg Leu Thr Leu Gly Arg Lys Gly Phe Val Arg
        195                 200                 205
Val Ala Leu Asp Asn Gly Ala Asp Leu Val Pro Val Leu Gly Phe Gly
210                 215                 220
Glu Asn Asp Val Phe Asp Thr Val Tyr Leu Pro Pro Asn Ser Trp Ala
225                 230                 235                 240
Arg Asn Val Gln Glu Phe Val Arg Lys Lys Leu Gly Phe Ala Thr Pro
                245                 250                 255
Ile Phe Ser Gly Arg Gly Ile Phe Gln Tyr Asn Met Gly Leu Met Pro
            260                 265                 270
His Arg Lys Pro Ile Ile Val Val Gly Lys Pro Ile Lys Ile Pro
        275                 280                 285
Lys Ile Pro Asp Glu Leu Lys Gly Arg Ala Leu Ser Thr Thr Ala Glu
290                 295                 300
Gly Val Ala Leu Val Asp Lys Tyr His Glu Lys Tyr Val Arg Ala Leu
305                 310                 315                 320
Arg Glu Leu Trp Asn Leu Tyr Lys Glu Glu Tyr Ala Thr Glu Pro Lys
                325                 330                 335
Ala Ala Tyr Leu Glu Pro Asn Ser Ile Arg Lys Asn Gln Asn Val
            340                 345                 350

<210> SEQ ID NO 18
<211> LENGTH: 1056
<212> TYPE: DNA
<213> ORGANISM: Aurantiochytrium limacinum

<400> SEQUENCE: 18
atgctcgcct ggatgcctgt cctcattgcc ctcccccgac gaaagcagac cgctgttgtt    60
ctcctgtttg tgatgctcct ccctatgatc atggtcgtgt actcctggac cctgatcctg   120
ctcattttcc ccctcaccac tctgcctact ctctcctacc tgatctggat tatgtacatt   180
gacaagtctc acgagaccgg aaagcgaaag ccctttatgc gatactggaa gatgtggcga   240
catttcgcca actactttcc tctccgactg atccgaacca ctcccctgga ccctcgacga   300
aagtacgtgt tctgctacca ccccatggca tcatttcccc tcggagcctt cggcaacttt   360
```

```
gctaccgact cgactggctt ctcccgaaag tttcccggta tcgatctgcg actgctcacc    420
ctccagatta acttctactg tcctatcatt cgagagctgc tcctgtacat gggtctgtgc    480
tctgccgcta agaagtcgtg taaccagatc ctccagcgag acccggctc tgctattatg    540 ctggttgtcg gcggtgccgc tgagtccctc gactctcagc ctggcaccta ccgactcact    600
ctgggtcgaa agggattcgt gcgagttgcc ctggacaacg gtgctgatct ggtccccgtg    660
ctcggtttcg gagagaacga cgtgtttgat accgtttacc tgcccctaa ctcgtgggcc     720 cgaaacgtcc aggagttcgt gcgaaagaag ctcggattcg ctaccccat cttttccggc     780 cgaggtattt ttcagtacaa catgggtctg atgccccacc gaaagcctat cattgtggtt    840
gtcggaaagc ccatcaagat tcccaagatc cctgacgagc tgaagggacg agccctctct    900
accactgccg agggcgttgc tctggtcgat aagtaccatg agaagtacgt tcgagccctc    960
cgagagctgt ggaacctcta caaggaggag tacgctaccg agcccaaggc cgcttacctc    1020
gagcctaact cgattcgaaa gaaccagaac gtctaa                             1056
```

<210> SEQ ID NO 19
<211> LENGTH: 666
<212> TYPE: PRT
<213> ORGANISM: Yarrowia lipolytica

<400> SEQUENCE: 19

```
Met Lys Ser Arg Val Ala Val Val Leu Ala Pro Val Leu Ala Pro Phe
1               5                   10                  15

Val Ala Ile Leu Lys Asn Leu Trp Val Phe Phe Thr Ala Leu Leu Glu
            20                  25                  30

Leu Leu Phe Asp Val Ser Trp His Trp Met Leu Gln Ser Trp His Trp
        35                  40                  45

Trp Cys Ser Thr Asp Gln Lys Thr Leu Gln Leu Gln Leu Asp Gln
    50                  55                  60

Ala Asp Thr Tyr Glu Glu Trp Glu Ser Ile Ala Ser Glu Leu Asp Glu
65                  70                  75                  80

Leu Leu Gly Asn Asp Val Trp Arg Gln Thr Ala Ala Ser Lys Arg Tyr
                85                  90                  95

Asp Tyr Arg Leu Ile Ala Gly Arg Leu Arg Asp Phe Ile Glu Cys Arg
            100                 105                 110

Ala Val Gly Asp Ile Ala Thr Leu Ile Ser Arg Leu Arg Ser Gly Leu
        115                 120                 125

Leu Arg Asn Leu Gly Ser Ile Ser Ser Leu Gln Leu Tyr Thr Arg Ser
    130                 135                 140

Tyr Leu Gly Ser Lys Leu Leu Ile Glu Glu Tyr Ile Thr Glu Val Ile
145                 150                 155                 160

Asp Cys Leu Lys Tyr Ile Lys Asp Tyr Gly Thr Thr Gly Gly Leu Asp
                165                 170                 175

Thr Lys Gly Val His Phe Phe Pro Lys Ser Glu Gln Arg Gln Leu Asp
            180                 185                 190

Ser Glu Gln Leu Thr Arg Gln Lys Lys His Lys Leu Phe Tyr Asp Thr
        195                 200                 205

Arg Gln Ser Phe Gly Arg Thr Ala Leu Val Leu Gln Gly Gly Thr Ile
    210                 215                 220

Phe Gly Leu Thr His Leu Gly Thr Ile Lys Ala Leu Thr Leu Gln Gly
225                 230                 235                 240

Leu Leu Pro Gly Ile Val Thr Gly Phe Lys Glu Gly Ala Phe Ile Ala
```

```
                245                 250                 255
Ala Leu Thr Gly Ile Tyr Val Ser Asp Leu Glu Leu Glu Thr Ile
            260                 265                 270
Asp Ser Leu Pro Asp Thr Leu Asn Asp Leu Tyr Gln Lys Tyr Lys Glu
            275                 280                 285
Arg Leu Ala Glu Glu Asn Lys His Lys Asp His Ser Phe Ser Asn Ser
290                 295                 300
Asn Ser Asp Tyr Asp Phe Asp Tyr Ala Phe Asp Phe Glu Gln Phe Ala
305                 310                 315                 320
Asn Thr Tyr Asn Val Thr Phe Ser Ser Val Thr Asp Lys Val Leu Arg
                325                 330                 335
Ser Glu Tyr Pro Pro Glu Val Lys Met Tyr Glu Glu Phe Ile Glu Asn
                340                 345                 350
Gln Leu Gly Asp Leu Thr Phe Glu Glu Ala Phe Asn Lys Ser Asp Arg
                355                 360                 365
Val Leu Asn Ile Val Ala His Ser His Asp Ser Ser Phe Pro Thr Leu
                370                 375                 380
Met Asn Tyr Leu Thr Thr Pro Asn Val Leu Ile Arg Ser Ala Cys Arg
385                 390                 395                 400
Ala Ser Met Val Thr Ala His Asp Glu Pro Gln Thr Lys Lys Ala Cys
                405                 410                 415
Ala His Leu Leu Val Lys Asp Asp Asn Ser Val Ile Pro Tyr Asp
                420                 425                 430
Ala Cys Lys Ser Arg Arg Gly Ser Ser Thr Asp Val Ile Leu Gly Pro
                435                 440                 445
Val Gln Glu Glu Val Asp Pro Leu Asp Ser Thr Ala Asn Gly Thr Asn
                450                 455                 460
Ser Ser Gly Pro Pro Lys Leu Glu Ile Thr Thr Asp Thr Trp Lys Arg
465                 470                 475                 480
Asn Asn Ala Asp Asp Glu Asp His Val Asp Thr Leu Pro Gly Arg Val
                485                 490                 495
Ser Ala Leu Pro Thr Pro Ser Tyr Ser Met Ile Asn Gln Gly Lys Ile
                500                 505                 510
Val Ser Pro Tyr Ala Arg Leu Ser Glu Leu Phe Asn Val Asn His Phe
                515                 520                 525
Ile Val Ser Leu Ser Arg Pro Tyr Leu Ala Pro Leu Leu Ala Ile Glu
                530                 535                 540
Gly Arg His Arg Gly Tyr His Gly Trp Arg Val Asn Leu Ile Arg Val
545                 550                 555                 560
Leu Lys Leu Glu Phe Glu His Arg Leu Ala Gln Phe Asp Tyr Ile Gly
                565                 570                 575
Leu Leu Pro Thr Ile Phe Arg Arg Phe Phe Ile Asp Lys Ile Pro
                580                 585                 590
Gly Ile Gly Pro Asn Ala Glu Val Leu Ile Val Pro Glu Leu Ala Ala
                595                 600                 605
Gly Met Ile Ser Asp Phe Lys Lys Ala Phe Ser Asn His Asp Ile Pro
610                 615                 620
Glu Lys Val Arg Tyr Trp Thr Thr Val Gly Glu Arg Ala Thr Trp Pro
625                 630                 635                 640
Leu Val Ala Ala Ile Trp Ala Arg Thr Ala Ile Glu Tyr Thr Leu Asn
                645                 650                 655
Asp Met Tyr Asn Gln Thr Lys Arg Gln Asn
                660                 665
```

<210> SEQ ID NO 20
<211> LENGTH: 2201
<212> TYPE: DNA
<213> ORGANISM: Yarrowia lipolytica

<400> SEQUENCE: 20

| | | | | | |
|---|---|---|---|---|---|
| cttttacgag | tgtgtatcat | cacatgatta | tgcagcaaga | tcagtatcat | ttcggctatc | 60 |
| cagctctctt | ccccgttca | gctccttttc | taccgcgatt | atgaaaagcc | gcgtggccgt | 120 |
| tgtcttggcg | ccggttctgg | caccatttgt | ggcgattttg | aaaaacctgt | gggtcttctt | 180 |
| cacagctcta | ctggagctct | tattcgacgt | tagctggcac | tggatgttac | aatcatggca | 240 |
| ctggtggtgc | tccaccgacc | aaaaaacact | gctacaactg | cagctggacc | aggcagacac | 300 |
| ctacgaggaa | tgggaaagca | ttgcatcgga | gctggacgag | ctgctgggca | cgacgtgtg | 360 |
| gcgtcagacc | gcagcctcga | aacgatacga | ctaccggctg | attgcaggcc | gtctgagaga | 420 |
| ctttatcgag | tgccgggcgg | tcggcgacat | tgcgacgctg | atttctcgtc | tgcgaagcgg | 480 |
| actgctgcgg | aatttgggct | cgatttcgtc | gctccagctg | tacactcgct | cgtacctcgg | 540 |
| ctctaaactg | ctcatcgaag | agtacatcac | cgaggtcatt | gactgtctca | agtacatcaa | 600 |
| ggactatggg | acgacgggcg | gactggacac | caagggagtg | catttcttcc | caaagtccga | 660 |
| acagcgacaa | ctggacagtg | aacagctgac | tcgacaaaag | aaacacaagt | tattctacga | 720 |
| cacacgacaa | tcttttggcc | gaacggccct | cgtgttgcag | ggaggaacta | ttttcggact | 780 |
| tactcatctc | ggaacaatca | aggctcttac | tctccagggt | ctgctaccgg | gtattgtcac | 840 |
| cggtttcaag | gaggggcgt | ttattgccgc | tctcacaggc | atctacgtat | ccgacctgga | 900 |
| gctgctcgaa | accattgact | ctttgccaga | cactctcaat | gacctgtacc | aaaaatacaa | 960 |
| ggagcgactg | gcggaggaaa | acaaacacaa | ggaccactcg | ttcagtaact | ccaattcgga | 1020 |
| ctacgacttt | gactacgcat | ttgactttga | acagtttgca | aacacctata | atgtgaccctt | 1080 |
| ctcgtctgtc | actgacaaag | tattgcgatc | ggagtacccc | ccggaagtca | aaatgtacga | 1140 |
| ggagttcatc | gagaatcaac | tcggagacct | cacgttcgaa | gaggccttca | caaaagcga | 1200 |
| ccgcgtgctc | aacattgtcg | cccattccca | tgactcttcc | ttcccgacac | tgatgaacta | 1260 |
| cctcaccact | cccaatgtgc | tcatcagaag | cgcatgtaga | gcttccatgg | tgaccgccca | 1320 |
| cgacgagccc | caaacgaaaa | aggcatgtgc | ccatctgctg | gtcaaggatg | acgacaacag | 1380 |
| cgtcattccc | tatgacgcct | gcaaatccag | gcgaggaagc | tcgaccgacg | tgattctggg | 1440 |
| acctgtccag | gaggaggtgg | atccattaga | ttcaacagct | aacggtacta | actcttctgg | 1500 |
| acctcccaaa | ctcgaaatca | caactgacac | ctggaaacga | aacaatgcag | acgacgagga | 1560 |
| ccacgtggat | actctcccgg | gccgcgtgag | tgctctacct | acaccttcgt | actccatgat | 1620 |
| taaccagggc | aagattgtct | ctccctacgc | tcgccttttcc | gaactcttta | acgtcaacca | 1680 |
| cttcatcgtc | tctctctcaa | gaccctacct | ggcgcctctt | ctggccatcg | aaggccgaca | 1740 |
| tagaggctac | cacggctgga | gagtgaacct | gatccgagta | ctgaaactag | aattcgaaca | 1800 |
| cagactcgcc | cagttcgact | acataggcct | gctgccgacc | atcttccgtc | ggttcttcat | 1860 |
| cgacgataag | atccctggca | tcggtcccaa | cgccgaggtc | ctcattgttc | ctgagctagc | 1920 |
| ggctggcatg | atctccgact | tcaaaaaggc | cttttcgaac | cacgacattc | ccgagaaggt | 1980 |
| ccgctactgg | accactgtgg | gcgaacgagc | cacctggcct | ctagtcgccg | ccatctgggc | 2040 |
| cagaacagca | atcgagtaca | ccctcaacga | catgtacaac | cagaccaagc | gacaaaacta | 2100 |

-continued

```
gaccccgagc agagcacata actactaacg atgagactaa agtatgtact gtatgtacta    2160
aacatacgct cgtaaacagt tgtatttatt cttttcagc a                         2201
```

<210> SEQ ID NO 21
<211> LENGTH: 341
<212> TYPE: PRT
<213> ORGANISM: Escherichia coli

<400> SEQUENCE: 21

```
Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val Tyr
    50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
    210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
                245                 250                 255

Ala Gly Ser Pro Arg Leu Arg Ala Tyr Met Leu Arg Ile Gly Leu Asp
            260                 265                 270

Gln Leu Tyr Gln Ser Leu Val Asp Gly Asn Phe Asp Asp Ala Ala Trp
        275                 280                 285

Ala Gln Gly Arg Cys Asp Ala Ile Val Arg Ser Ala Gly Thr Val
    290                 295                 300

Gly Arg Thr Gln Ile Ala Arg Arg Ser Ala Ala Val Trp Thr Asp Gly
305                 310                 315                 320

Cys Val Glu Val Leu Ala Asp Ser Gly Asn Arg Arg Pro Ser Thr Arg
                325                 330                 335

Pro Arg Ala Lys Glu
            340
```

```
<210> SEQ ID NO 22
<211> LENGTH: 1026
<212> TYPE: DNA
<213> ORGANISM: Escherichia coli

<400> SEQUENCE: 22
atgaagaagc cgagctgac cgctacctct gttgagaagt tcctgattga gaagtttgat      60
tccgtttccg acctgatgca gctgtccgag ggcgaggagt ctcgagcctt ctcctttgac    120
gtgggcggac gaggttacgt tctgcgagtg aactcgtgtg ccgacggctt ctacaaggat    180
cgatacgtct accgacactt tgcttctgcc gctctgccca tccctgaggt tctcgacatt    240
ggcgagttct ctgagtccct cacctactgc atctctcgac gagctcaggg agtcaccctg    300
caggacctcc ctgagactga gctgcctgct gtcctccagc tgttgctga ggccatggac     360 gctatcgctg ctgctgatct gtcccagacc tcgggtttcg cccccttgg acctcaggga     420 attggacagt acaccacttg gcgagacttc atctgtgcta ttgccgatcc tcacgtctac    480
cattggcaga ccgttatgga cgatactgtg tcggcttctg tcgctcaggc tctggacgag    540
ctgatgctct gggccgagga ttgccccgag gttcgacacc tggtgcatgc tgacttcggt    600
tccaacaacg ttctcaccga caacggccga atcactgccg tgattgactg gtccgaggct    660
atgtttggcg actcgcagta cgaggtggcc aacatcttct tttggcgacc ctggctggct    720
tgtatggagc agcagacccg atacttcgag cgacgacatc ctgagctcgc tggatcccct    780
cgactgcgag cttacatgct ccgaattggt ctggaccagc tctaccagtc gctggtggat    840
ggcaactttg acgatgctgc ctgggctcag ggacgatgtg acgccatcgt gcgatctggc    900
gctggaaccg tcggacgaac tcagattgcc cgacgatccg ctgctgtctg gaccgacgga    960
tgcgtggagg tcctggctga ttcgggtaac cgacgaccct ctactcgacc tcgagctaag   1020
gagtaa                                                              1026

<210> SEQ ID NO 23
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cagctctctt ccccgttca gctcctttc taccgcgatt atgaagaagc ccgagctgac      60

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agcatcgtca aagttgccat ccac                                           24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
```

```
accacttggc gagacttcat ctgt                                              24
```

<210> SEQ ID NO 26
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

```
tttagtctca tcgttagtag ttatgtgctc tgctcggggt tactccttag ctcgaggtcg       60
```

<210> SEQ ID NO 27
<211> LENGTH: 898
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
cagctctctt cccccgttca gctccttttc taccgcgatt atgaagaagc ccgagctgac       60
cgctacctct gttgagaagt tcctgattga aagtttgat tccgtttccg acctgatgca      120
gctgtccgag ggcgaggagt ctcgagcctt ctcctttgac gtgggcggac gaggttacgt     180
tctgcgagtg aactcgtgtg ccgacggctt ctacaaggat cgatacgtct accgacactt     240
tgcttctgcc gctctgccca tccctgaggt tctcgacatt ggcgagttct ctgagtccct     300
cacctactgc atctctcgac gagctcaggg agtcaccctg caggacctcc ctgagactga     360
gctgcctgct gtcctccagc ctgttgctga ggccatggac gctatcgctg ctgctgatct     420
gtcccagacc tcgggtttcg gccccttggg acctcaggga attggacagt acaccacttg     480
gcgagacttc atctgtgcta ttgccgatcc tcacgtctac cattggcaga ccgttatgga     540
cgatactgtg tcggcttctg tcgctcaggc tctggacgag ctgatgctct gggccgagga     600
ttgccccgag gttcgacacc tggtgcatgc tgacttcggt tccaacaacg ttctcaccga     660
caacggccga atcactgccg tgattgactg gtccgaggct atgtttggcg actcgcagta     720
cgaggtggcc aacatcttct tttggcgacc ctggctggct tgtatggagc agcagacccg     780
atacttcgag cgacgacatc ctgagctcgc tggatcccct cgactgcgag cttacatgct     840
ccgaattggt ctggaccagc tctaccagtc gctggtggat ggcaactttg acgatgct      898
```

<210> SEQ ID NO 28
<211> LENGTH: 633
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

```
accacttggc gagacttcat ctgtgctatt gccgatcctc acgtctacca ttggcagacc       60
gttatggacg atactgtgtc ggcttctgtc gctcaggctc tggacgagct gatgctctgg      120
gccgaggatt gccccgaggt tcgacacctg gtgcatgctg acttcggttc caacaacgtt      180
ctcaccgaca acggccgaat cactgccgtg attgactggt ccgaggctat gtttggcgac      240
tcgcagtacg aggtggccaa catcttcttt tggcgaccct ggctggcttg tatggagcag      300
cagacccgat acttcgagcg acgacatcct gagctcgctg gatccccctcg actgcgagct     360
```

```
tacatgctcc gaattggtct ggaccagctc taccagtcgc tggtggatgg caactttgac    420
gatgctgcct gggctcaggg acgatgtgac gccatcgtgc gatctggcgc tggaaccgtc    480
ggacgaactc agattgcccg acgatccgct gctgtctgga ccgacggatg cgtggaggtc    540
ctggctgatt cgggtaaccg acgaccctct actcgacctc gagctaagga gtaaccccga    600
gcagagcaca taactactaa cgatgagact aaa                                 633
```

<210> SEQ ID NO 29
<211> LENGTH: 526
<212> TYPE: PRT
<213> ORGANISM: Yarrowia lipolytica

<400> SEQUENCE: 29

```
Met Glu Val Arg Arg Arg Lys Ile Asp Val Leu Lys Ala Gln Lys Asn
1               5                   10                  15

Gly Tyr Glu Ser Gly Pro Pro Ser Arg Gln Ser Ser Gln Pro Ser Ser
            20                  25                  30

Arg Ala Ser Ser Arg Thr Arg Asn Lys His Ser Ser Thr Leu Ser
        35                  40                  45

Leu Ser Gly Leu Thr Met Lys Val Gln Lys Lys Pro Ala Gly Pro Pro
    50                  55                  60

Ala Asn Ser Lys Thr Pro Phe Leu His Ile Lys Pro Val His Thr Cys
65                  70                  75                  80

Cys Ser Thr Ser Met Leu Ser Arg Asp Tyr Asp Gly Ser Asn Pro Ser
                85                  90                  95

Phe Lys Gly Phe Lys Asn Ile Gly Met Ile Ile Leu Ile Val Gly Asn
            100                 105                 110

Leu Arg Leu Ala Phe Glu Asn Tyr Leu Lys Tyr Gly Ile Ser Asn Pro
        115                 120                 125

Phe Phe Asp Pro Lys Ile Thr Pro Ser Glu Trp Gln Leu Ser Gly Leu
    130                 135                 140

Leu Ile Val Val Ala Tyr Ala His Ile Leu Met Ala Tyr Ala Ile Glu
145                 150                 155                 160

Ser Ala Ala Lys Leu Leu Phe Leu Ser Ser Lys His His Tyr Met Ala
                165                 170                 175

Val Gly Leu Leu His Thr Met Asn Thr Leu Ser Ser Ile Ser Leu Leu
            180                 185                 190

Ser Tyr Val Val Tyr Tyr Leu Pro Asn Pro Val Ala Gly Thr Ile
        195                 200                 205

Val Glu Phe Val Ala Val Ile Leu Ser Leu Lys Leu Ala Ser Tyr Ala
    210                 215                 220

Leu Thr Asn Ser Asp Leu Arg Lys Ala Ala Ile His Ala Gln Lys Leu
225                 230                 235                 240

Asp Lys Thr Gln Asp Asp Asn Glu Lys Glu Ser Thr Ser Ser Ser Ser
                245                 250                 255

Ser Ser Asp Asp Ala Glu Thr Leu Ala Asp Ile Asp Val Ile Pro Ala
            260                 265                 270

Tyr Tyr Ala Gln Leu Pro Tyr Pro Gln Asn Val Thr Leu Ser Asn Leu
        275                 280                 285

Leu Tyr Phe Trp Phe Ala Pro Thr Leu Val Tyr Gln Pro Val Tyr Pro
    290                 295                 300

Lys Thr Glu Arg Ile Arg Pro Lys His Val Ile Arg Asn Leu Phe Glu
305                 310                 315                 320
```

```
Leu Val Ser Leu Cys Met Leu Ile Gln Phe Leu Ile Phe Gln Tyr Ala
            325                 330                 335

Tyr Pro Ile Met Gln Ser Cys Leu Ala Leu Phe Phe Gln Pro Lys Leu
            340                 345                 350

Asp Tyr Ala Asn Ile Ser Glu Arg Leu Met Lys Leu Ala Ser Val Ser
            355                 360                 365

Met Met Val Trp Leu Ile Gly Phe Tyr Ala Phe Phe Gln Asn Gly Leu
            370                 375                 380

Asn Leu Ile Ala Glu Leu Thr Cys Phe Gly Asn Arg Thr Phe Tyr Gln
385                 390                 395                 400

Gln Trp Trp Asn Ser Arg Ser Ile Gly Gln Tyr Trp Thr Leu Trp Asn
            405                 410                 415

Lys Pro Val Asn Gln Tyr Phe Arg His His Val Tyr Val Pro Leu Leu
            420                 425                 430

Ala Arg Gly Met Ser Arg Phe Asn Ala Ser Val Val Phe Phe Phe
            435                 440                 445

Ser Ala Val Ile His Glu Leu Leu Val Gly Ile Pro Thr His Asn Ile
            450                 455                 460

Ile Gly Ala Ala Phe Phe Gly Met Met Ser Gln Val Pro Leu Ile Met
465                 470                 475                 480

Ala Thr Glu Asn Leu Gln His Ile Asn Ser Ser Leu Gly Pro Phe Leu
            485                 490                 495

Gly Asn Cys Ala Phe Trp Phe Thr Phe Phe Leu Gly Gln Pro Thr Cys
            500                 505                 510

Ala Phe Leu Tyr Tyr Leu Ala Tyr Asn Tyr Lys Gln Asn Gln
            515                 520                 525

<210> SEQ ID NO 30
<211> LENGTH: 1581
<212> TYPE: DNA
<213> ORGANISM: Yarrowia lipolytica

<400> SEQUENCE: 30
atggaagtcc gacgacgaaa aatcgacgtg ctcaaggccc agaaaaacgg ctacgaatcg    60
ggcccaccat ctcgacaatc gtcgcagccc tcctcaagag catcgtccag aacccgcaac   120
aaacactcct cgtccaccct gtcgctcagc ggactgacca tgaaagtcca gaagaaacct   180
gcgggacccc cggcgaactc caaaacgcca ttcctacaca tcaagcccgt gcacacgtgc   240
tgctccacat caatgctttc gcgcgattat gacggctcca accccagctt caagggcttc   300
aaaaacatcg gcatgatcat tctcattgtg gaaatctac ggctcgcatt cgaaaactac   360
ctcaaatacg gcatttccaa cccgttcttc gaccccaaaa ttactccttc gagtggcag   420 ctctcaggct tgctcatagt cgtggcctac gcacatatcc tcatggccta cgctattgag   480
agcgctgcca agctgctgtt cctctctagc aaacaccact acatggccgt ggggcttctg   540
cataccatga acactttgtc gtccatctcg ttgctgtcct acgtcgtcta ctactacctg   600
cccaaccccg tggcaggcac aatagtcgag tttgtggccg ttattctgtc tctcaaactc   660
gcctcatacg ccctcactaa ctcggatctc cgaaaagccg caattcatgc ccagaagctc   720
gacaagacgc aagacgataa cgaaaaggaa tccacctcgt cttcctcttc ttcagatgac   780
gcagagactt tggcagacat tgacgtcatt cctgcatact acgcacagct gccctacccc   840
cagaatgtga cgctgtcgaa cctgctgtac ttctggtttg ctcccacact ggtctaccag   900
cccgtgtacc ccaagacgga gcgtattcga cccaagcacg tgatccgaaa cctgtttgag   960
```

-continued

```
ctcgtctctc tgtgcatgct tattcagttt ctcatcttcc agtacgccta ccccatcatg   1020
cagtcgtgtc tggctctgtt cttccagccc aagctcgatt atgccaacat ctccgagcgc   1080
ctcatgaagt tggcctccgt gtctatgatg gtctggctca ttggattcta cgctttcttc   1140
cagaacggtc tcaatcttat tgccgagctc acctgttttg gaaacagaac cttctaccag   1200
cagtggtgga attcccgctc cattggccag tactggactc tatggaacaa gccagtcaac   1260
cagtacttta gacaccacgt ctacgtgcct cttctcgctc ggggcatgtc gcggttcaat   1320
gcgtcggtgg tggttttctt tttctccgcc gtcatccatg aactgcttgt cggcatcccc   1380
actcacaaca tcatcggagc cgccttcttc ggcatgatgt cgcaggtgcc tctgatcatg   1440
gctactgaga accttcagca tattaactcc tctctgggcc ccttccttgg caactgtgca   1500
ttctggttca ccttttttcct gggacaaccc acttgtgcat tcctttatta tctggcttac   1560
aactacaagc agaaccagta g                                               1581
```

<210> SEQ ID NO 31
<211> LENGTH: 697
<212> TYPE: PRT
<213> ORGANISM: Rhodosporidium toruloides

<400> SEQUENCE: 31

```
Met Thr Glu Arg Ser Leu Pro Val Thr Leu Pro Leu Pro Arg Asn Phe
 1               5                  10                  15

Ala Leu Thr Pro His Gln Met Ala Ser Pro Asp Pro Pro Leu Pro Gly
            20                  25                  30

Pro Ala Asn Leu Val Asp Asp Ala Leu Arg His Pro Asp Ser Ala Pro
        35                  40                  45

Pro Ile Ser Pro Asp Ser Ala Pro Pro Ser Thr Ala Thr Arg Pro Ser
    50                  55                  60

Ala Leu Ser Arg Gly Glu Leu Ser Thr Ala Ser Ser Tyr Ala Ser Glu
65                  70                  75                  80

Val Ser Thr Arg Glu Gly Thr Pro Asp Leu Ala Asn Gly Gln Gly Val
                85                  90                  95

Thr Thr Thr Ile Thr Thr Val Thr Gly Lys Gly Gly Lys Ala Val Thr
            100                 105                 110

Gln Thr Leu Thr His Val Gly Ala Ala Ser Val Asp Ala Arg Phe Ser
        115                 120                 125

Ser Thr Thr Asn Ser Ile Thr Leu Arg Pro Ile Pro Ala Arg Gly Gly
    130                 135                 140

Asp Pro Lys Lys Ile Lys Val Leu Arg Ser Arg Arg Thr His Phe Ala
145                 150                 155                 160

Pro Arg Thr Ser His Phe Asp Arg His Asn Leu Thr Ser Ala Ser Asp
                165                 170                 175

Pro Phe Arg Gly Leu Tyr Thr Leu Phe Trp Ile Val Ile Phe Val Gly
            180                 185                 190

Ala Leu Lys Thr Val Tyr His Arg Phe Ala Glu Gln Gly Gly Trp Gly
        195                 200                 205

Gly Glu Trp Arg Phe Ala Ala Leu Ile Ser Arg Asp Gly Trp Val Leu
    210                 215                 220

Ala Val Ser Asp Ala Val Leu Val Ser Ala Ser Leu Leu Cys Val Pro
225                 230                 235                 240

Tyr Ala Lys Leu Leu Val His Gly Trp Ile Arg Tyr His Gly Ala Gly
                245                 250                 255

Val Ile Ile Gln His Ile Cys Gln Thr Leu Tyr Leu Ala Ile Ala Ile
```

```
            260                 265                 270
Arg Trp Thr Phe His Arg Asn Trp Pro Trp Val Gln Ser Gly Phe Met
            275                 280                 285
Thr Leu His Ala Leu Ser Met Leu Met Lys Ile His Ser Tyr Cys Ser
            290                 295                 300
Leu Asn Gly Glu Leu Ser Glu Arg Arg Gln Leu Lys Lys Asp Glu
305                 310                 315                 320
Lys Arg Leu Glu Glu Val Leu Glu Glu Met Gly Gly Arg Arg Lys Ala
                        325                 330                 335
Glu Arg Glu Ala Arg Glu Glu Trp Glu Arg Gln Cys Gly Glu Ala Ala
                        340                 345                 350
Arg Ala Lys Glu Gly Glu Ala Gly Val Ser Glu Gly Glu Lys Glu Ala
                        355                 360                 365
Ala Ala Thr Leu Ser Ser Thr Asp Ala Ser Asn Ser Ala Leu Ser Ser
                        370                 375                 380
Glu Asp Glu Ala Ala Ala Leu Leu Arg His Arg Gln Pro Thr Ala
385                 390                 395                 400
Arg Arg Arg Ser Ile Ser Pro Ser Ala Ser Arg Thr Gly Ser Ser Ser
                        405                 410                 415
Ala Pro Ser Ala Thr Leu Ala Pro Ser Arg Ala Glu Glu Pro Gln Glu
                        420                 425                 430
Gly Val Glu Thr Leu Thr Trp His Pro Ser Asp Gln Val Ser Lys Leu
                        435                 440                 445
Ala Ile Ala Ile Cys Glu Ala Lys Asp Leu Leu Thr Ser Asn Gly Lys
                        450                 455                 460
Lys Pro Val Thr Phe Pro Glu Asn Val Thr Phe Ala Asn Phe Ile Asp
465                 470                 475                 480
Tyr Leu Leu Val Pro Thr Leu Val Tyr Glu Leu Glu Tyr Pro Arg Thr
                        485                 490                 495
Asp Ser Ile Arg Pro Leu Tyr Ile Leu Glu Lys Thr Leu Ala Thr Phe
                        500                 505                 510
Gly Thr Phe Ser Ile Leu Val Leu Ile Val Asp Ser Phe Ile Leu Pro
                        515                 520                 525
Val Thr Ser Arg Thr Asp Thr Pro Leu Phe Gly Phe Val Leu Asp Leu
                        530                 535                 540
Ala Leu Pro Phe Thr Leu Ala Tyr Leu Leu Ile Phe Tyr Val Ile Phe
545                 550                 555                 560
Glu Gly Val Cys Asn Gly Phe Ala Glu Leu Thr Arg Phe Ala Asp Arg
                        565                 570                 575
Asn Phe Phe Asp Asp Trp Trp Asn Ser Cys Thr Phe Asp Glu Phe Ser
                        580                 585                 590
Arg Lys Trp Asn Arg Pro Val His Ala Phe Leu Leu Arg His Val Tyr
                        595                 600                 605
Ala Glu Thr Met Ala Ser Tyr Lys Leu Ser Lys Leu Ser Ala Ala Phe
                        610                 615                 620
Val Thr Phe Leu Phe Ser Ala Cys Val His Glu Leu Val Met Ala Val
625                 630                 635                 640
Val Thr Lys Lys Leu Arg Leu Tyr Leu Phe Ser Met Gln Met Ala Gln
                        645                 650                 655
Leu Pro Leu Ile Met Val Gly Arg Ala Lys Ile Phe Arg Gln Tyr Pro
                        660                 665                 670
Ala Leu Gly Asn Leu Phe Phe Trp Leu Ala Leu Leu Ser Gly Phe Pro
                        675                 680                 685
```

Leu Leu Gly Thr Leu Tyr Leu Arg Tyr
    690                 695

<210> SEQ ID NO 32
<211> LENGTH: 2094
<212> TYPE: DNA
<213> ORGANISM: Rhodosporidium toruloides

<400> SEQUENCE: 32

| | | | | | |
|---|---|---|---|---|---|
| atgacggagc | gatcccttcc | agtgacgctc | cctcttcctc | gaaactttgc | gctcacaccg | 60 |
| caccagatgg | cctcgccaga | cccgccactc | ccaggcccag | ccaacctcgt | cgacgacgca | 120 |
| ctccgacacc | cagactcggc | gccgcccatc | tcgcccgact | ccgcgcctcc | ttcgactgcg | 180 |
| actcggccct | ctgctctctc | gcgcggagag | ctctcgaccg | cttcgagcta | cgcgagcgag | 240 |
| gtgtcgacga | gggaggggac | accggatctg | gcgaatgggc | aaggggttac | gacgaccatc | 300 |
| acgactgtca | caggcaaagg | cggaaaggcc | gtcacccaga | ccctcaccca | cgtcggcgcc | 360 |
| gcctccgtcg | acgcccgctt | ctcctccacc | acaaactcca | tcactctccg | ccctatcccc | 420 |
| gcccgtggcg | cgacccgaa | aaagatcaaa | gtcctccgct | ctcgtcggac | ccacttcgcc | 480 |
| ccacgcacct | cacacttcga | ccgtcacaac | ctcacctccg | cctctgaccc | gttccgcgga | 540 |
| ctgtacacgt | tgttctggat | cgtgatcttc | gttggggcac | tcaagactgt | gtatcatcgg | 600 |
| tttgcggaac | agggtgggtg | gggtggagaa | tggaggtttg | cggcgttgat | tagtcgcgat | 660 |
| gggtgggttc | tggcggttag | tgatgcggtg | ttggttagcg | cgtcgttgtt | gtgcgtgccg | 720 |
| tatgcaaagc | tcctcgtaca | cggctggatc | cggtaccacg | gcgcaggcgt | catcatccaa | 780 |
| cacatctgtc | aaacgctcta | cctcgccatc | gcgatccgct | ggaccttcca | ccgcaactgg | 840 |
| ccctgggtcc | aaagcggttt | catgaccctc | cacgccctct | cgatgctcat | gaagatccat | 900 |
| agctactgtt | ctctgaacgg | cgagctttcg | gagcggcgga | gacagttgaa | gaaggacgag | 960 |
| aagcggttgg | aggaggtgct | ggaggagatg | ggtggacgga | ggaaggcgga | gagggaggcg | 1020 |
| agggaggagt | gggagaggca | gtgtggggag | gcggcgaggg | ccaaggaggg | tgaggcggga | 1080 |
| gtgagcgagg | gggagaagga | ggcggcggcg | actctatctt | cgacggatgc | gtcgaattcg | 1140 |
| gccctttcgt | cggaggacga | ggcggctgcg | gcgctgttgc | ggcatcgaca | gccgactgct | 1200 |
| cgacgacgat | ccatctcgcc | ctgcctca | cgcaccggtt | cctcctccgc | cccctccgct | 1260 |
| accctcgccc | cctctcgcgc | cgaagaaccc | caagaaggcg | ttgagacgct | cacctggcac | 1320 |
| ccatccgacc | aagtcagcaa | actcgctatc | gccatctgcg | aggcaaagga | cctcctcacg | 1380 |
| agtaacggca | agaagcccgt | cacgttcccc | gagaacgtca | cctttgcgaa | ctttatcgac | 1440 |
| tacttgcttg | tgccgacgtt | ggtgtacgag | ttggagtacc | ctcggacgga | ttccatccgg | 1500 |
| cccctctaca | tcctcgaaaa | gaccctcgca | accttcggca | ccttctccat | tctcgtcctc | 1560 |
| atcgtcgact | cgttcatcct | ccccgtcacc | tcgcgcaccg | acacgcccct | cttcgggttc | 1620 |
| gtcctcgacc | tcgccctgcc | gttcacgctc | gcgtacctcc | tcatcttcta | cgtcatcttt | 1680 |
| gagggcgtgt | gcaatgggtt | tgcggagttg | acgaggtttg | cggatcggaa | tttcttcgac | 1740 |
| gattggtgga | actcgtgcac | gttcgacgag | ttctcgcgca | agtggaatcg | ccccgtccac | 1800 |
| gccttcctcc | tccgccacgt | ttacgccgaa | acgatggctt | cttacaagct | ctcgaagctc | 1860 |
| tcggctgcgt | tcgtcacgtt | cttgttcagc | gcctgcgtgc | acgaactcgt | catggcggtc | 1920 |
| gtgacgaaga | agcttcggct | gtacctgttc | tcgatgcaga | tggcccagct | cccgctcatc | 1980 |
| atggtgggcc | gcgccaagat | cttccgacag | tatccagcgc | tcggcaacct | cttcttctgg | 2040 |

```
ctcgcccttc tctcgggatt cccgcttctc gggacgctgt atctgcggta ctga          2094
```

<210> SEQ ID NO 33
<211> LENGTH: 555
<212> TYPE: PRT
<213> ORGANISM: Lipomyces starkeyi

<400> SEQUENCE: 33

```
Met Ser Thr Ala Ala Gln Ser Asp Thr Asp Asn Glu Asp Ile Ser Thr
1               5                   10                  15

Val Asp Leu Val Asp Ser Arg Ala Asp Thr His Thr Ser Ser Asn Val
            20                  25                  30

Met Leu Gln Gln Lys Ser Arg Arg Leu Ile Gly Lys Asp Ala
        35                  40                  45

Glu Pro Arg Thr Gln His Pro Ser Gly Gly Lys Ser Glu Lys Glu Glu
    50                  55                  60

Leu Thr Lys Pro Asp Asp Ser Lys Gly Pro Ile Lys Leu Ser His Ile
65                  70                  75                  80

Tyr Pro Ile His Ala Val Ser Arg Gly Ser Ile Leu Ser Arg Glu Ser
                85                  90                  95

Thr Thr Pro Thr Pro Ser Phe Val Gly Phe Arg Asn Leu Ala Met Ile
            100                 105                 110

Val Leu Gly Lys Leu Gln Tyr Ser Leu Phe Phe Trp Cys Asp Arg Ala
        115                 120                 125

Asn Ile Pro Thr Ala Val Ser Asn Leu Arg Leu Val Ile Glu Asn Tyr
    130                 135                 140

Ser Lys Tyr Gly Val Leu Ile Arg Phe Ala Arg Leu Gly Ile Ser Gln
145                 150                 155                 160

Lys Asp Ile Leu Tyr Cys Ile Phe Leu Thr Ala Thr Ile Pro Leu His
                165                 170                 175

Leu Phe Ile Ala Ile Val Ile Glu Arg Leu Val Ala Ile Pro Thr Val
            180                 185                 190

Asn Tyr Val Ala Ser Leu Ser Glu Ser Glu Asp Lys Lys Arg Ser Asn
        195                 200                 205

Pro Lys Met Gly Arg Lys Gly Gly Ser Ile Ser Ile Leu Arg Pro Lys
    210                 215                 220

Pro Lys Tyr Met Trp Arg Leu Ile Val Leu Leu His Ser Ile Asn Ala
225                 230                 235                 240

Met Ala Cys Leu Trp Val Thr Thr Val Val Tyr Asn Ser Ile Tyr
                245                 250                 255

His Pro Leu Ile Gly Thr Ala Cys Glu Phe His Ala Val Ile Val Cys
            260                 265                 270

Leu Lys Val Ala Ser Phe Ala Leu Thr Asn Arg Asp Leu Arg Glu Ser
        275                 280                 285

Met Leu Asn Ser Gln Pro Val Pro Ala Ile Tyr Asn Leu Ala Pro Tyr
    290                 295                 300

Pro Lys Asn Leu Thr Leu Lys Asn Leu Ser Tyr Phe Trp Trp Ala Pro
305                 310                 315                 320

Thr Leu Val Tyr Gln Pro Val Tyr Pro Arg Ser Pro Ser Phe Arg Pro
                325                 330                 335

Leu Phe Phe Val Lys Arg Ile Leu Glu Met Val Gly Leu Ser Phe Leu
            340                 345                 350

Ile Trp Phe Leu Ser Ala Gln Tyr Ala Val Pro Thr Leu Glu Asn Ser
        355                 360                 365
```

```
Leu Val His Phe His Ser Leu Gln Phe Met Gly Ile Met Glu Arg Leu
    370                 375                 380

Met Lys Leu Ala Ser Ile Ser Met Ala Ile Trp Leu Ala Gly Phe Phe
385                 390                 395                 400

Cys Ile Phe Gln Ser Gly Leu Asn Ala Leu Ala Glu Val Met Arg Phe
                405                 410                 415

Gly Asp Arg Ala Phe Tyr Asp Asp Trp Trp Asn Ser Lys Ser Val Gly
                420                 425                 430

Glu Tyr Trp Arg Leu Trp Asn Lys Pro Val Thr Asn Tyr Phe Arg Arg
            435                 440                 445

His Ile Tyr Val Pro Leu Val Arg Arg Gly Trp Asn Ser Ala Thr Ala
    450                 455                 460

Ser Val Met Val Phe Phe Val Ser Ala Val Leu His Glu Leu Val Val
465                 470                 475                 480

Gly Val Pro Thr His Asn Val Ile Gly Val Ala Phe Ser Ser Met Ile
                485                 490                 495

Leu Gln Ile Pro Leu Ile Gln Val Thr Ala Pro Leu Glu Lys Met His
                500                 505                 510

Gly Pro Thr Ser Gly Ile Ile Gly Asn Cys Ile Phe Trp Phe Ser Phe
            515                 520                 525

Phe Ile Gly Gln Pro Leu Gly Val Leu Leu Tyr Tyr Phe Ala Trp Asn
    530                 535                 540

Val Ser Met Ser Lys Val Lys Met Val Glu Ser
545                 550                 555

<210> SEQ ID NO 34
<211> LENGTH: 1668
<212> TYPE: DNA
<213> ORGANISM: Lipomyces starkeyi

<400> SEQUENCE: 34
atgtcgaccg ctgcacaatc tgatacagac aacgaggata tatcgactgt cgatttggtt       60
gactctcgtg cagatactca cacatcttca aatgttatgt tgcaacagca aaaatcgcgt      120
cggagactaa tcgggaaaga cgccgagcca agaacacagc atccgtctgg aggcaaatcg      180
gagaaggagg agttgacgaa gccggatgac tcaaagggac ccataaaatt aagtcacata      240
tacccgatac atgccgttag ccgaggcagt attctgtcac gagagtcgac aactcctaca      300
ccgagttttg ttgggtttcg aaacttagcc atgatagtgc tagggaagtt acagtattca      360
ttattctttt ggtgcgatcg ggctaacatt ccgacagccg tcagcaatct tcgattggtg      420
attgaaaatt actcaaagta cggcgttctg atccgattcg cccgactcgg tatttcacaa      480
aaggacattc tgtattgcat attcttgacc gctaccatcc cgctgcacct atttattgct      540
attgtcattg aaagactagt tgcgattccg acggtaaact acgtcgcttc gctcagcgag      600
agcgaggata aaaacgctc caaccccaaa atgggacgga agggggggcag tatatcgatt      660 ttgcgtccta agccaaaata tatgtggcgc ctgatcgtcc tattgcattc aataaacgca      720
atggcttgct tgtgggttac gactgttgtt gtttacaatt ctatttatca tccccttatt      780
gggacagctt gtgaatttca tgcagtgatt gtgtgtctta aggtcgcatc gtttgcgctt      840
accaatcgcg atcttcggga gtcgatgctg aactctcaac ctgtgccagc catatacaac      900
ttggcccctt atccaaaaaa cttaaccctc aagaacttgt catactttg gtgggcgccg      960 actcttgttt atcaacctgt ctatccgcga tcgccttcat tccggccttt gttttttgtc     1020
```

-continued

```
aagcggattc tggagatggt gggcctatca ttttaatat ggttcttgtc agctcaatat    1080
gctgtgccga cgctagaaaa tagtttggtg cattttcaca gtttgcaatt catgggaatt    1140
atggagcgac tcatgaagct tgctagcatt agcatggcta tttggcttgc tggttttttc    1200 tgcattttc agtctggact caatgcgctt gcggaggtaa tgcggtttgg tgacagagcc    1260
ttttacgacg actggtggaa cagcaaatct gtgggagagt attggcgtct gtggaataag    1320
ccggttacga attacttccg gcgtcatatt tacgtaccgc ttgtgcgccg cgggtggaat    1380
tctgcgacag ccagtgtcat ggatttttc gtcagcgcgg tgttgcatga gctagttgtt    1440
ggagttccga cgcataacgt aattggagtt gcattctcgt cgatgattct acaaatccca    1500
ctcatacaag taaccgcgcc tctggagaag atgcatggac ctacatctgg aataataggg    1560
aactgtatct tttggtttag cttcttcatc ggtcagcctc tgggcgtgct actttactat    1620
tttgcgtgga acgttagtat gagcaaagta aagatggtcg agagctag                1668
```

<210> SEQ ID NO 35
<211> LENGTH: 517
<212> TYPE: PRT
<213> ORGANISM: Aspergillus terreus

<400> SEQUENCE: 35

```
Met Val Met Asp Thr Gln Thr Thr Ala Ser Ala Thr Ser Thr Ala Leu
1               5                   10                  15

Thr Thr Asp His Thr Val Ala Ser Arg Thr Ser Arg Ser Glu Pro Asn
            20                  25                  30

Gly Gly Val His Asn Val Ser Ser Pro Pro Thr Ser Glu Pro Thr Gly
        35                  40                  45

Gly Asn Gly Gly Gly Arg Arg Arg Ser Lys Tyr Arg His Val Ala Ala
    50                  55                  60

Tyr His Ser Glu Val Arg His Ser Ser Leu Ser Arg Glu Ser Asn Thr
65                  70                  75                  80

Ser Pro Ser Phe Leu Gly Phe Arg Asn Leu Met Val Ile Val Leu Gly
                85                  90                  95

Glu Cys Pro Ser Ala Leu Leu Arg Phe Val Asn Pro Thr Glu Asn Ser
            100                 105                 110

Tyr Gly Ser Arg Leu Val Ala Met Asn Leu Arg Leu Val Ile Glu Asn
        115                 120                 125

Tyr Val Lys Tyr Gly Val Leu Ile Cys Ile Arg Cys His Asp Tyr Arg
    130                 135                 140

Lys Gln Asp Val Val Leu Gly Ser Met Leu Phe Ala Leu Val Pro Cys
145                 150                 155                 160

Gln Leu Phe Ile Ala Tyr Leu Leu Glu Leu Ala Ala Ala Gly Arg Ala
                165                 170                 175

Lys Gln Thr Val Gly Arg Lys Lys Asp Gly Ser Ala Glu Glu Gly
            180                 185                 190

Glu Arg Glu Ala Arg Ala Phe Arg His Ile Trp Arg Phe Ala Leu Ser
        195                 200                 205

Phe His Ile Leu Asn Ile Val Leu Asn Leu Ala Val Thr Ser Phe Val
    210                 215                 220

Val Tyr Tyr Tyr Ile His His Pro Gly Ile Gly Thr Leu Cys Glu Val
225                 230                 235                 240

His Ala Ile Val Val Ala Leu Lys Asn Trp Ser Tyr Ala Phe Thr Asn
                245                 250                 255

Arg Asp Leu Arg Glu Ala Met Leu Asn Pro Ser Ala Glu Ser Ala Leu
```

```
                260                 265                 270
Pro Glu Ile Tyr Ser Ser Leu Pro Tyr Pro Lys Asn Ile Thr Leu Gly
            275                 280                 285

Asn Leu Thr Tyr Phe Trp Leu Ala Pro Thr Leu Leu Tyr Gln Pro Val
        290                 295                 300

Tyr Pro Arg Ser Pro Ser Ile Arg Trp Pro Phe Val Ala Lys Arg Leu
305                 310                 315                 320

Ser Glu Phe Ala Cys Leu Ser Val Phe Ile Trp Leu Leu Ser Ala Gln
                325                 330                 335

Tyr Ala Ala Pro Val Leu Arg Asn Ser Ile Asp Lys Ile Arg Asp Met
            340                 345                 350

Ala Tyr Ala Ser Ile Phe Glu Arg Val Met Lys Leu Ser Thr Ile Ser
        355                 360                 365

Leu Val Ile Trp Leu Ala Gly Phe Phe Ala Ile Phe Gln Ser Leu Leu
    370                 375                 380

Asn Ala Leu Ala Glu Ile Met Lys Phe Gly Asp Arg Glu Phe Tyr Thr
385                 390                 395                 400

Asp Trp Trp Asn Ser Pro Ser Leu Gly Val Tyr Trp Arg Ser Trp Asn
                405                 410                 415

Arg Pro Val Tyr Gln Phe Met Lys Arg His Val Tyr Ser Pro Leu Ile
            420                 425                 430

Gly Arg Gly Tyr Ser Pro Phe Val Ala Ser Thr Val Val Phe Thr Ile
        435                 440                 445

Ser Ala Leu Leu His Glu Leu Leu Val Gly Ile Pro Thr His Asn Met
    450                 455                 460

Ile Gly Val Ala Leu Val Gly Met Leu Phe Gln Leu Pro Leu Ile Ala
465                 470                 475                 480

Ile Thr Ala Pro Leu Glu Lys Met Lys Asp Pro Leu Gly Lys Pro Leu
                485                 490                 495

Gly Ala Leu Leu Tyr Phe Phe Ala Trp Gln Ala Lys Tyr Gly Ser Val
            500                 505                 510

Ser Arg Met Gly Asn
        515

<210> SEQ ID NO 36
<211> LENGTH: 1554
<212> TYPE: DNA
<213> ORGANISM: Aspergillus terreus

<400> SEQUENCE: 36
atggtgatgg acacacaaac cacagcatcc gccaccagca cggcgctcac gaccgaccac      60
actgttgcct ctcggacgtc ccgctctgag ccgaacggtg gtgtgcataa tgtatcgtca     120
cctccaacga gcgaaccgac tgggggaaat ggcggaggcc ggcgaaggag taaataccgg     180
catgtcgcag cgtaccattc cgaagtgcgc cattccagtc tcagtcggga atcgaatact     240
tctccgagtt tcctcggatt ccggaacctc atggtaatcg tattaggtga gtgccctagt     300
gctctcctac gttttgtgaa cccgacggag aactcatacg ggtcgcgact agttgctatg     360
aatcttcgat tggttatcga gaattacgtg aagtatgggg tcttgatctg catcagatgc     420
cacgattatc gaaagcagga cgttgtcctg ggctcaatgt tatttgctct cgtcccatgc     480
cagctattca tcgcctacct cctggaattg gccgcagcgg taggccaa acagactgtg      540 ggccgaaaga aaaaggacgg atcagccgag gagggcgaac gtgaagcacg tgcttttcga     600
cacatctggc ggtttgcatt gtcctttcac atcctcaaca ttgttctcaa tctcgccgtc     660
```

```
acgagcttcg ttgtgtatta ctacatccac catcccggca ttggtacgct ctgtgaagtg    720
catgcgatcg ttgtcgcgtt gaaaaactgg tcctatgcgt tcaccaatcg ggatctgcga    780
gaggcgatgc ttaatccctc ggcggagtcg gcgcttcccg agatctattc cagcctcccg    840
tacccgaaaa acatcacgtt aggaaatcta acgtacttct ggcttgcacc gacactgttg    900
tatcagccag tataccccag gtcgccttcc atccgatggc cattcgtggc caaacgcttg    960
tcggaatttg cgtgcttgtc ggtgttcatt tggctacttt cggcccaata cgctgcgcca   1020
gttttgcgca actccattga caagattcgt gatatggcat atgcatccat tttgagcgc   1080 gttatgaagc tatccaccat ctctctcgtc atttggctgg ctgggttctt tgcgattttc   1140
caatcactct tgaatgcttt ggcggagatc atgaagtttg gcgatcggga attctacacc   1200
gattggtgga atagcccaag tctcggtgtt tactggcggt catggaatcg gccagtgtac   1260
cagttcatga agcggcacgt atattctccg ttgatagggc gggggtacag cccgtttgtg   1320
gcaagcactg tcgtattcac catctccgct ctccttcatg agctcctcgt ggggataccc   1380
acgcacaaca tgataggcgt cgcgcttgtt ggaatgctgt tccagctccc gttgatcgcc   1440
atcactgccc cattggaaaa gatgaaagat ccattgggta agcccctggg agcactgctg   1500
tatttctttg cctggcaggc aaaatatggc agtgtgagca ggatgggcaa ctga         1554
```

```

<210> SEQ ID NO 37
<211> LENGTH: 506
<212> TYPE: PRT
<213> ORGANISM: Claviceps purpurea

<400> SEQUENCE: 37

Met Ser Ala Thr Gly Val Asp Val Ala Asn Gly Arg Ser Gly Ala Arg
1               5                   10                  15

Arg Arg Asn Asp Thr Ala Val Asp Glu Thr Ile Ser Ala Val Thr Ala
            20                  25                  30

Glu Met Arg Ser Ser Ser His Pro Thr Tyr Arg His Val Ser Ala Val
        35                  40                  45

His Ser Thr Ser Arg Pro Ser Cys Leu Ser His Asp Ser Asp Ala Ala
    50                  55                  60

Pro Ser Phe Ile Gly Phe Arg Asn Leu Met Val Ile Val Leu Val Val
65                  70                  75                  80

Gly Asn Val Arg Leu Met Ile Glu Asn Leu Lys Lys Tyr Gly Val Leu
                85                  90                  95

Ile Cys Leu Arg Cys His Ser Tyr Lys Asn Glu Asp Ile Ile Ile Gly
            100                 105                 110

Gly Leu Leu Tyr Phe Leu Ile Pro Cys His Leu Leu Val Ala Tyr Gly
        115                 120                 125

Ile Glu Leu Ala Ala Ala Arg Gln Ala Arg Glu Ser Arg Thr Arg Pro
    130                 135                 140

Pro Gly Gln Ser Asp Thr Ala Ser Lys Ser Thr Glu Asp Asp Asn Lys
145                 150                 155                 160

His Phe His Ser Thr Trp Val Leu Ala Ala Trp Ala His Ile Ile Asn
                165                 170                 175

Met Thr Leu Ser Phe Ile Leu Thr Thr Phe Val Val Tyr Tyr Tyr Val
            180                 185                 190

His His Pro Leu Val Gly Thr Leu Thr Glu Met His Ala Val Ile Val
        195                 200                 205

Ser Leu Lys Thr Ala Ser Tyr Ala Phe Thr Asn Arg Asp Leu Arg His
```

```
    210                 215                 220

Ala Tyr Leu His Pro Asp Lys Arg Lys His Ile Pro Glu Leu Tyr Leu
225                 230                 235                 240

Glu Cys Pro Tyr Pro Gln Asn Leu Thr Phe Gly Asn Leu Val Tyr Phe
                245                 250                 255

Trp Trp Ala Pro Thr Leu Val Tyr Gln Pro Val Tyr Pro Arg Thr Asp
            260                 265                 270

Lys Ile Arg Trp Val Phe Val Phe Lys Arg Leu Gly Glu Val Cys Cys
        275                 280                 285

Leu Ser Ala Phe Ile Trp Phe Ala Ser Phe Gln Tyr Ala Ala Pro Val
    290                 295                 300

Leu Arg Asn Ser Leu Asp Lys Ile Ala Ser Leu Asp Phe Ile Met Ile
305                 310                 315                 320

Phe Glu Arg Leu Leu Lys Leu Ser Thr Ile Ser Leu Val Ile Trp Leu
                325                 330                 335

Ala Gly Phe Phe Ala Leu Phe Gln Ser Phe Leu Asn Ala Leu Ala Glu
            340                 345                 350

Val Leu Arg Phe Gly Asp Arg Cys Phe Tyr Asp Asp Trp Trp Asn Ser
        355                 360                 365

Glu Ser Leu Gly Ala Tyr Trp Arg Thr Trp Asn Arg Pro Val Tyr Thr
    370                 375                 380

Tyr Phe Lys Arg His Val Tyr Val Pro Met Ile Gly Arg Gly Trp Ser
385                 390                 395                 400

Pro Trp Thr Ala Ser Cys Thr Val Phe Phe Val Ser Ala Val Leu His
                405                 410                 415

Glu Val Leu Val Gly Val Pro Thr His Asn Ile Ile Gly Val Ala Phe
            420                 425                 430

Val Gly Met Phe Leu Gln Leu Pro Leu Ile Ala Leu Thr Ala Pro Met
        435                 440                 445

Glu Lys Lys Lys Trp Gly His Thr Gly Arg Val Met Gly Asn Val Ile
    450                 455                 460

Phe Trp Val Ser Phe Thr Ile Phe Gly Gln Pro Phe Ala Ala Leu Met
465                 470                 475                 480

Tyr Phe Tyr Ala Trp Gln Ala Lys Tyr Gly Ser Val Ser Arg Gln Ile
                485                 490                 495

Val Leu Val Asn Pro Val Glu Glu Ala Ser
            500                 505

<210> SEQ ID NO 38
<211> LENGTH: 1521
<212> TYPE: DNA
<213> ORGANISM: Claviceps purpurea
<400> SEQUENCE: 38
atgtccgcca cgggcgttga tgtggccaac ggccgcagcg gcgcgcgacg acgcaacgat      60
actgccgtcg acgagactat atccgccgtc acggccgaga tgcgttcctc gtcgcatcca     120
acataccgcc atgtgtctgc tgtgcactcc acgagccggc cctcgtgtct gagccatgat     180
tctgacgctg cgccgagctt cattggcttt cgaaatctca tggtcattgt tctggtcgtt     240
ggcaatgttc gattaatgat tgaaaatcta aaaaagtacg gcgtactgat atgcctccga     300
tgtcactcgt ataaaaacga agacatcatt atcggcggac tgctctactt cctgatcccc     360
tgccacttgc ttgtcgccta cggaatcgag ttagccgccg ccagacaagc acgcgaatct     420
cgaactcgtc caccaggcca gtccgacacg gcgtcgaaat caacagaaga tgacaacaag     480
```

```
cacttccact caacatgggt gctcgctgcc tgggcacaca tcatcaacat gacactttcc    540
ttcatcctca ccaccttcgt cgtctactac tacgtgcacc atcccctcgt cggcaccctg    600
accgagatgc acgccgtcat cgtctctctc aaaacagctt cctacgcatt caccaaccga    660
gatcttcgcc acgcatacct ccatcctgac aagcgcaagc acatcccga gctatatctc     720 gaatgtccct accccagaa cctcaccttt ggcaatctcg tgtatttctg gtgggccccc      780
acgctggtat accagcccgt gtatccgcgc accgacaaga tcagatgggt ttttgttttt    840
aaaagactag gcgaagtctg ctgtctcagc gcattcatct ggttcgccag cttccagtac    900
gccgcgcccg tgttgcggaa ctccctggac aagattgcgt ctctcgactt catcatgatc    960
tttgagcgcc ttctcaagct atccaccatt tctctcgtca tctggctcgc cggcttcttc   1020
gccctgttcc agtctttcct gaatgccctg gctgaggtat tgcgctttgg ggaccggtgc   1080
ttctacgacg attggtggaa tagcgagagt ctggggcgt attggaggac gtggaacagg    1140
cctgtgtata cctacttcaa gcgccatgtg tatgtgccca tgattgggag gggatggagt   1200
ccctggactg ctagttgtac tgtttttttt gtgtcggcgg tgctgcacga ggttcttgtt   1260
ggggtgccca cccacaatat cattggtgtc gcctttgtgg gcatgtttct gcagcttccc   1320
ctaatagccc tcaccgctcc catggaaaag aagaaatggg gccacaccgg ccgtgtgatg   1380
ggcaatgtta ttttctgggt gtcctttaca atctttgggc agccctttgc agcgctcatg   1440
tacttttatg cctggcaggc caagtacggg agcgtgagtc ggcaaattgt gctggtgaat   1500
ccggtggagg aggcgtcttg a                                              1521
```

<210> SEQ ID NO 39
<211> LENGTH: 551
<212> TYPE: PRT
<213> ORGANISM: Chaetomium globosum

<400> SEQUENCE: 39

```
Met Lys Ala Glu Thr Gly Thr Thr Met Ala Thr Ser Thr Ser Leu Glu
1               5                   10                  15

Thr Ser Gln Val Asn Gly Val Thr Asn Arg Ala Pro Val Gly Pro Ser
            20                  25                  30

His Asp Pro His Ala Thr Thr Pro Thr His Glu Thr Thr Thr Ile
        35                  40                  45

Pro Ser Asp Val Leu Ala Asn Gly Ser Thr Asn Gly Thr Thr Asn Gly
    50                  55                  60

Thr Thr Asp Asp Ser Leu Asp Ile Ser Glu Leu Arg Lys Ala Phe Arg
65                  70                  75                  80

Asn Lys Tyr Arg His Val Glu Ala Val His Ser Glu Ser Lys Pro Ser
                85                  90                  95

Cys Leu Ser His Asp Ala Thr Glu Thr Pro Ser Phe Ile Gly Phe Arg
            100                 105                 110

Asn Leu Met Val Ile Val Leu Val Ala Ala Asn Leu Arg Leu Val Ile
        115                 120                 125

Glu Asn Ile Gln Lys Tyr Gly Val Leu Ile Cys Ile Lys Cys His Asp
    130                 135                 140

Phe Arg Pro Asn Asp Val Arg Leu Gly Leu Leu Tyr Ile Leu Ile
145                 150                 155                 160

Pro Trp His Leu Met Leu Ala Tyr Leu Ile Glu Leu Val Ala Ala Ala
                165                 170                 175

Asn Ala Arg Asn Ser Arg Ala Lys Ala Lys Lys Arg Asp Gly Ser Thr
```

180                 185                 190
Ser Pro Thr Glu Asp Glu Ser Lys Gln Phe Leu Gln Thr Trp Arg Met
            195                 200                 205

Leu Arg Ile Leu His Ala Val Asn Val Thr Ala Ala Leu Ala Val Thr
210                 215                 220

Ser Tyr Val Val Tyr Tyr Ile His His Pro Leu Ile Gly Thr Leu
225                 230                 235                 240

Ser Glu Leu His Ala Ile Ile Val Trp Leu Lys Thr Ala Ser Tyr Ala
            245                 250                 255

Leu Thr Asn Arg Asp Leu Arg His Ala Tyr Leu His Pro Val Arg Gly
        260                 265                 270

Glu Arg Asp Ala Leu Pro Glu Ile Tyr Ala Gln Cys Pro Tyr Pro Ala
    275                 280                 285

Asn Val Thr Phe Ser Asn Leu Thr Tyr Phe Trp Ala Pro Thr Leu
290                 295                 300

Val Tyr Gln Pro Ala Tyr Pro Arg Thr Gln Arg Ile Arg Trp Val Phe
305                 310                 315                 320

Val Ala Lys Arg Leu Gly Glu Val Val Cys Leu Ser Ala Phe Ile Trp
            325                 330                 335

Phe Ala Ser Ala Gln Tyr Ala Thr Pro Val Leu Arg Asn Ser Leu Asp
        340                 345                 350

Lys Ile Ala Thr Leu Asp Tyr Met Ser Ile Val Glu Arg Leu Leu Lys
    355                 360                 365

Leu Ser Thr Ile Ser Leu Val Ile Trp Leu Ala Gly Phe Ala Leu
370                 375                 380

Phe Gln Ser Phe Leu Asn Ala Leu Ala Glu Val Met Arg Phe Gly Asp
385                 390                 395                 400

Arg Glu Phe Tyr Glu Ala Trp Trp Asn Ser Glu Ser Leu Gly Ala Tyr
            405                 410                 415

Trp Arg Thr Trp Asn Lys Pro Val Tyr Gln Phe Phe Arg Arg His Val
        420                 425                 430

Tyr Ser Pro Met Arg Ser Arg Gly Trp Ser His Leu Ser Ala Ser Leu
    435                 440                 445

Ala Val Phe Leu Leu Ser Ala Val Leu His Glu Leu Leu Val Gly Val
450                 455                 460

Pro Thr His Asn Ile Ile Gly Val Ala Phe Leu Gly Met Phe Leu Gln
465                 470                 475                 480

Leu Pro Leu Ile Ala Met Thr Ala Arg Leu Gly Gly Arg Arg Gly Asn
            485                 490                 495

Thr Ala His Gly Arg Leu Leu Gly Asn Thr Ile Phe Trp Val Ser Phe
        500                 505                 510

Thr Ile Phe Gly Gln Pro Phe Ala Leu Met Tyr Phe Tyr Ala Trp
    515                 520                 525

Gln Ala Lys Tyr Gly Ser Val Ser Lys Met Pro Leu Ala Gln Pro Gly
530                 535                 540

Thr Cys Pro Ala Val Val Val
545                 550

<210> SEQ ID NO 40
<211> LENGTH: 1656
<212> TYPE: DNA
<213> ORGANISM: Chaetomium globosum

<400> SEQUENCE: 40

| | | | | | | |
|---|---|---|---|---|---|---|
| atgaaggcag | aaacgggcac | aacgatggca | acgtcgacta | gtctcgagac | ttcccaagtc | 60 |
| aatggcgtca | ccaaccgggc | ccctgttggc | cctagtcacg | accccacgc | tacaactccg | 120 |
| actcatgaga | cgacaaccac | cataccgtcc | gacgtcctcg | ccaatggttc | tacaaatggg | 180 |
| actacgaatg | ggacgacaga | tgattcattg | gacatatccg | aattgcgcaa | agcgttccgc | 240 |
| aacaagtatc | gccatgtcga | ggctgtccac | tccgaatcga | aaccatcctg | tctgagccat | 300 |
| gacgctacag | agacacccag | tttcatcggt | tttaggaatc | tcatggtgat | gtgtgttggt | 360 |
| gctgccaatc | ttcgcctggt | catcgagaac | attcaaaagt | atggagttct | gatctgcatc | 420 |
| aaatgccacg | actttcgccc | caacgatgta | cgcctgggc | cctcctcta | catcctgatc | 480 |
| ccatggcacc | tcatgctcgc | ctacctcatt | gagctggtcg | ccgccgccaa | tgcccgcaac | 540 |
| tcccgggcca | aggcgaagaa | gcgggacggc | agtaccagcc | cgaccgaaga | cgagtccaag | 600 |
| caattcctgc | agacctggcg | gatgctccgc | attctccacg | ccgtcaacgt | cacggccgcc | 660 |
| ctggccgtca | cctcctacgt | ggtctactac | tacattcacc | accgctgat | cggcacgctc | 720 |
| tcggagctgc | acgccatcat | cgtgtggctc | aagacggcgt | cgtacgcgct | caccaaccgc | 780 |
| gacctgcgcc | acgcctacct | acaccccggtg | cgcggcgagc | gcgacgctct | gcccgagatc | 840 |
| tacgcccagt | gcccctaccc | ggccaacgtg | accttctcca | acttgaccta | cttctggtgg | 900 |
| gcgcccaccc | tggtgtacca | gccggcgtac | ccgcgcactc | agcgcatccg | ctgggtcttt | 960 |
| gtggctaagc | gcctcggcga | ggtcgtctgc | ttgagcgcct | tcatctggtt | cgccagcgcc | 1020 |
| cagtacgcta | ccccgtgct | gcgaaactcg | ctcgacaaga | tcgctaccct | ggattacatg | 1080 |
| tccattgtcg | agcgtctgtt | gaagctgtcg | accatctcgc | tggtcatctg | gctggcgggc | 1140 |
| ttctttgcgc | tgtttcagag | tttcctgaat | gccttggccg | aggtgatgcg | gtttggagac | 1200 |
| cgcgagttct | acgaagcatg | gtggaacagc | gaaagcctcg | gcgcctactg | gcgcacctgg | 1260 |
| aacaaacccg | tgtaccaatt | cttccggcgg | cacgtctact | cgccgatgcg | gtcgcgcggg | 1320 |
| tggagccact | tgtcggccag | cctgccgtg | tttctgctct | cggccgtgct | acacgagctg | 1380 |
| ctggtggggg | tgccgacgca | caacatcatc | ggcgtcgcct | tcctgggcat | gttcctgcag | 1440 |
| ctgccgctca | tcgccatgac | ggcgcgcctg | ggcggccgcc | gcgggaacac | cgcccacggc | 1500 |
| cgcctgctcg | gcaacactat | cttttgggtg | tcatttacca | ttttggcca | gccgtttgcc | 1560 |
| gcgctgatgt | atttttatgc | atggcaggcc | aagtatggta | gtgtgagcaa | gatgccgctg | 1620 |
| gcgcagccgg | ggacgtgtcc | ggctgtggtt | gtttga | | | 1656 |

<210> SEQ ID NO 41
<211> LENGTH: 388
<212> TYPE: PRT
<213> ORGANISM: Arxula adeninivorans

<400> SEQUENCE: 41

Met Val Arg Phe Ala Pro Leu Asn Val Pro Leu His Arg Arg Leu Glu
1               5                   10                  15

Thr Phe Ala Leu Thr Tyr His Ile Leu Ser Ile Pro Val Trp Met Ser
            20                  25                  30

Phe Phe Leu Leu Cys Cys Ala Ile Pro Leu Met Trp Pro Leu Val Ile
        35                  40                  45

Ile Tyr Leu Leu Tyr Tyr Ala Ser Asp Asn Ser Ser Glu Asn Gly Gly
    50                  55                  60

Val Ala Ser Arg Tyr Ser Pro Lys Phe Arg Ser Val Pro Leu Trp Lys
65                  70                  75                  80

```
Tyr Phe Ala Asn Tyr Phe Pro Ile Thr Leu His Arg Thr Gln Glu Leu
                85                  90                  95

Pro Pro Ala Phe Val Tyr Gln Gly Glu Asp Leu Asp Pro Glu Thr Pro
            100                 105                 110

Asp Asp Ser Asp Gly His Ala Lys Ser Lys Ser Ile Val Leu Lys
        115                 120                 125

Leu Trp Lys Val Ala Phe Trp Trp Tyr Leu Pro Lys His Phe Leu
130                 135                 140

Arg Lys Pro Glu Val Arg Pro Thr Gly Arg Arg Tyr Ile Phe Gly Tyr
145                 150                 155                 160

His Pro His Gly Ile Ile Gly Met Gly Ala Ile Gly Ala Ile Ala Thr
                165                 170                 175

Glu Gly Ala Gly Trp Ser Lys Leu Phe Pro Gly Ile Pro Val Ser Leu
            180                 185                 190

Leu Thr Leu Ala Asn Asn Phe Arg Ile Pro Leu Tyr Arg Glu Tyr Leu
        195                 200                 205

Met Ser Leu Gly Ile Ala Ser Val Ser Arg Arg Ser Cys Glu Ala Leu
    210                 215                 220

Leu Lys Arg Gly Gln Ser Ile Cys Ile Val Ile Gly Gly Ala Gln Glu
225                 230                 235                 240

Ser Leu Leu Ala His Pro Gly His Met Asp Leu Val Leu Lys Arg Arg
                245                 250                 255

Lys Gly Phe Ile Lys Leu Ala Leu Glu Val Gly Asn Thr Asp Leu Val
            260                 265                 270

Pro Val Met Ala Phe Gly Glu Asn Asp Leu Tyr Gln Gln Val Asn Ser
        275                 280                 285

Ser Lys Ser Ser Arg Leu Tyr Lys Leu Gln Ser Leu Val Lys Asn Ala
    290                 295                 300

Leu Gly Phe Thr Leu Pro Leu Met His Ala Arg Gly Val Phe Asn Tyr
305                 310                 315                 320

Asp Val Gly Ile Ile Pro Tyr Arg Arg Pro Ile Asn Val Val Gly
                325                 330                 335

Lys Pro Ile Pro Ile Pro His Ile Pro Asn Pro Ser Ala Asp Gln Val
            340                 345                 350

Asn Arg Tyr Gln Ile Gln Tyr Met Thr Glu Leu Lys Glu Leu Tyr Asp
        355                 360                 365

Lys Tyr Lys Asp Lys Cys Ser Asn Lys Asp Leu Pro Val Pro Glu Leu
    370                 375                 380

Thr Phe Val Glu
385

<210> SEQ ID NO 42
<211> LENGTH: 1167
<212> TYPE: DNA
<213> ORGANISM: Arxula adeninivorans

<400> SEQUENCE: 42
atggttcggt tcgctccttt aaatgttcct cttcatcgga ggttagagac gttcgcgctc    60
acctaccata tcctgtcgat tccagtatgg atgtccttct ttttgctatg ctgtgccatt   120
cctttaatgt ggccgttggt tatcatctac ctgctgtact atgcttccga caacagctct   180
gagaatggag gggttgcgag caggtattcg ccaaagttca ggtccgtgcc tctttggaag   240
tactttgcaa actactttcc aatcacccct caccgtactc aagagctacc gcccgcattc   300
gtgtaccaag gcgaagactt ggaccctgag acgcccgatg acagtgacga cgggcatgca   360
```

```
aagtcaaagt ctattgtatt aaagctgtgg aaagttgcat tctggtggta ctacttgccc      420
aagcattttc ttcgcaaacc agaggttcgt cctacgggtc gaagatacat ctttggatat      480
cacccccatg gaatcattgg catgggtgcc attggcgcaa ttgctactga aggtgcgggg      540
tggtccaagc tcttccccgg gatccctgtc agtttgctca ctctggcaaa caactttcga      600 atcccctgt accgggaata tctcatgtct ctgggcattg cctcggtatc tagacggtcc       660
tgtgaagctt tattaaaaag aggacagtca atttgcattg taattggagg cgctcaggaa      720
agtcttcttg cacatccagg gcacatggat ttggtgctca agcgacgcaa gggattcatt      780
aaactagctc ttgaagttgg caacaccgac ttggtgccag ttatggcatt tggagaaaac      840
gatctctacc agcaagtgaa cagtagcaaa tcctcccgtc tatacaagct ccagagccta      900
gttaagaatg ccttgggatt cacgcttccg ctgatgcacg ctcgaggagt gttcaattat      960
gacgtgggca taatacccta tcgaagacca attaacgttg tagtgggcaa gcccatcccc     1020
attccacaca ttccaaaccc atctgccgac caggtcaatc ggtaccagat ccagtacatg     1080
actgaactca agaattgta cgacaagtac aaagacaagt gcagtaacaa ggatcttcca      1140
gttccggagc ttacatttgt agagtag                                          1167

<210> SEQ ID NO 43
<211> LENGTH: 346
<212> TYPE: PRT
<213> ORGANISM: Rhodotorula graminis

<400> SEQUENCE: 43

Met Gly Ala Gln Glu Glu Val Asp Tyr Asp Gln Ser Asp His Thr Lys
1               5                   10                  15

Ile Lys Phe Val Pro Phe Val Pro Arg His Arg Leu Gln Thr
            20                  25                  30

Phe Ser Val Phe Leu Trp Thr Thr Ala Leu Pro Ile Ser Leu Gly Ile
        35                  40                  45

Phe Cys Ile Leu Cys Ser Phe Pro Pro Leu Trp Pro Leu Val Ile Gly
    50                  55                  60

Tyr Leu Thr Trp Val Phe Leu Ile Asp Gln Ala Pro Met Arg Gly Gly
65                  70                  75                  80

Arg Pro Gln Ala Trp Leu Arg Lys Ser Arg Val Trp Glu Trp Phe Ala
                85                  90                  95

Gly Tyr Tyr Pro Val Ser Leu Ile Lys Ser Ala Asp Leu Pro Pro Asp
            100                 105                 110

Gln Arg Tyr Val Phe Gly Tyr His Pro His Gly Val Ile Gly Met Gly
        115                 120                 125

Ala Ile Ala Asn Phe Gly Thr Asp Ala Thr Gly Phe Ser Arg Leu Phe
    130                 135                 140

Pro Gly Ile Thr Pro His Leu Leu Thr Leu Ala Ser Asn Phe Lys Leu
145                 150                 155                 160

Pro Val Tyr Arg Glu Leu Leu Leu Ala Leu Gly Ile Ser Ser Val Ser
                165                 170                 175

Met Lys Ser Cys Gln Asn Ile Leu Arg Gln Gly Pro Gly Ser Ser Ile
            180                 185                 190

Thr Ile Val Val Gly Gly Ala Ala Glu Ser Leu Ser Ala His Pro Gly
        195                 200                 205

Thr Ala Asp Leu Thr Leu Lys Arg Arg Lys Gly Phe Ile Lys Leu Ala
    210                 215                 220
```

```
Ile Arg Thr Gly Ala Ser Leu Val Pro Val Phe Ser Phe Gly Glu Asn
225                 230                 235                 240

Asp Ile Phe Asn Gln Leu Ser Asn Glu Arg Gly Thr Arg Leu Tyr Lys
            245                 250                 255

Leu Gln Lys Arg Phe Gln Ala Val Phe Gly Phe Thr Leu Pro Ile Phe
        260                 265                 270

Phe Gly Arg Gly Leu Phe Asn Tyr Asn Met Gly Leu Met Pro Tyr Arg
    275                 280                 285

His Pro Ile Val Ser Val Val Gly Arg Pro Ile Lys Val Lys Gln Lys
290                 295                 300

Asp His Pro Ser Thr Ala Asp Leu Glu Glu Val Gln Glu Arg Tyr Ile
305                 310                 315                 320

Ala Glu Leu Lys Arg Ile Trp Glu Asp Tyr Lys Glu Val Tyr Ala Lys
            325                 330                 335

Ser Arg Thr Lys Glu Leu Thr Ile Ile Ala
        340                 345

<210> SEQ ID NO 44
<211> LENGTH: 1041
<212> TYPE: DNA
<213> ORGANISM: Rhodotorula graminis

<400> SEQUENCE: 44
atgggcgcac aagaagaggt cgactacgac cagtcggacc acaccaagat caagttcgtg      60 cccttgtcg tcccgcggca ccgtcgcctc cagacgttct cggtcttcct gtggacgacg      120
gccctcccta tctcgctcgg catcttctgc atcctgtgct ccttccctcc tctttggccg      180
ctcgtcatcg ggtacctcac ctgggtcttc ctcattgacc aggcgccgat gcgcggcggg      240
aggccacaag cctggctgcg aaagtcgcgc gtgtgggagt ggttcgccgg ctactatccc      300
gtcagcctca tcaagagcgc cgacctcccg cccgaccagc gttacgtctt tggctaccac      360
cctcacggcg tcatcggcat gggcgccatc gccaactttg caccgacgc gaccgggttc      420 tcgcgcctgt tcccgggcat cacgccgcac ctcctcacgc tcgcgagcaa cttcaagctc      480
ccagtctacc gagagctcct cctcgccctc ggcatctcgt ccgtctcgat gaagagctgc      540
cagaacatcc tgcggcaagg tcccggctcg tccatcacga tcgtcgtcgg cggcgccgcc      600
gagagcctga gcgcgcaccc tggcacggcc gacctgacgc tcaagcgccg caagggcttc      660
atcaagctcg ccatccgcac cggcgcctcg ctcgtgcccg tcttttcctt tggcgagaac      720
gacatcttca accagctgtc gaacgagcga gggacgcgcc tgtacaagct gcagaagcgg      780
ttccaggccg tctttggctt cacattgccc atcttcttcg gccgaggcct gttcaactac      840
aacatgggct tgatgccgta ccgacacccc atcgtctcgg tcgtcggccg cccgatcaag      900
gtcaagcaga aggaccaccc gtcgactgcc gacctcgaag aagtccagga gcggtacatc      960
gccgagctca aaaggatctg ggaggactac aaggaggtgt acgccaagag tcgcaccaag     1020
gagctcacca tcatcgcctg a                                              1041

<210> SEQ ID NO 45
<211> LENGTH: 635
<212> TYPE: PRT
<213> ORGANISM: Pichia guilliermondii

<400> SEQUENCE: 45

Met Thr Lys Glu Val Asp Glu Ser Thr Gly Gly Ala Ser Asp Ile Pro
1               5                   10                  15
```

-continued

Asn Met Val Glu Glu Ala Lys Ser Ser Ser Phe Asp Arg Glu Thr Glu
        20                      25                      30

Glu Asn Leu Leu Leu Glu Thr Thr Lys Pro Asp Glu Asn Leu Val Pro
            35                      40                      45

Glu Ser Thr Lys His Asp Glu Lys Leu Val Pro Glu Ile Thr Lys His
    50                      55                      60

Glu Asp Asn Pro Met Glu Asn Asp Gln Val Ser Gln Asn Thr Ala Thr
65                      70                      75                      80

Ser Pro Met Thr Gly Ala Gly Ser Glu Glu Thr Arg Asp Leu Ile Thr
                85                      90                      95

Glu Asn Ile Glu Lys Pro Asp Glu Gly Asp Leu Leu Ile Glu Leu Ile
            100                     105                     110

Ser Lys Asp Asn Asp Gly Asp Gly Asp Asp Gly Leu Lys Asn Arg Lys
        115                     120                     125

Gln Lys Arg Ser Ser Ser Glu Val Lys Arg Leu Arg Met Ser Ser Leu
    130                     135                     140

Ala Pro Lys Gly Pro Thr Pro Gln Lys His Glu Arg Pro Lys Tyr Ile
145                     150                     155                     160

Asn Val Ala Pro Leu Asn Ile Pro Ile Arg Arg Arg Leu Glu Met Val
                165                     170                     175

Gly Ile Ile Trp His Thr Ile Cys Ile Pro Thr Phe Val Ser Leu Phe
            180                     185                     190

Phe Leu Thr Leu Ser Leu Gly Pro Phe Ala Trp Val Gly Val Ile Leu
        195                     200                     205

Pro Tyr Phe Leu Trp Trp Tyr Leu Ile Asp Leu His Thr Pro Thr Asn
210                     215                     220

Gly Lys Val Ala Tyr Arg Ser Arg Asp Trp Met Lys Asn Phe Ile Val
225                     230                     235                     240

Trp Asp Trp Phe Val Asp Tyr Phe Pro Ile Arg Val His Lys Ser Cys
                245                     250                     255

Glu Leu Glu Pro Thr Phe Ser Asp Val Ile Glu Asp Val Val
            260                     265                     270

Pro Asp Asp Glu Glu Asp Leu Ile Ser Glu Gln Ser Arg Thr Gly Val
        275                     280                     285

Asp Lys Leu Phe Lys Phe Leu Gly Leu Arg Lys Arg Leu Asn Asp Asp
    290                     295                     300

Ser Asp Ala Ser Ser Gln Cys Ser Leu Leu Gln Glu Ser Leu Ser Thr
305                     310                     315                     320

Arg Arg Lys Val Lys Arg Met Ser Thr Gly Pro Arg Tyr Ile Phe Gly
                325                     330                     335

Tyr His Pro His Gly Val Ile Ser Met Gly Val Phe Gly Thr Phe Ala
            340                     345                     350

Thr Asn Ala Leu Arg Asn Glu Pro Tyr Glu Pro Pro Leu Arg Leu Leu
        355                     360                     365

Lys Pro Phe Phe His Asp Ser Lys Gly Glu Arg Leu Phe Pro Gly
    370                     375                     380

Ile Gly Thr Val Phe Pro Leu Thr Leu Thr Thr Gln Phe Ile Val Pro
385                     390                     395                     400

Tyr Tyr Arg Asp Tyr Ile Leu Gly Met Gly Leu Thr Ser Ala Ser Ala
                405                     410                     415

Lys Asn Ile Lys Ser Leu Ile Ser Asn Gly Asp Asn Ser Ile Cys Val
            420                     425                     430

Val Val Gly Gly Ala Gln Glu Ser Leu Leu Asn Asp Met Val Ala Ala

|  | 435 |  |  | 440 |  |  | 445 |  |  |  |  |
|---|---|---|---|---|---|---|---|---|---|---|---|
| Thr | Thr | Val | Pro | Gly | Arg | Tyr | Gly | Lys | Ser | Asn | Leu | Pro | Asn | Asp | Ser |
| 450 |  |  |  |  | 455 |  |  |  |  | 460 |  |

Asp Thr Asp Ser Glu Phe Asp Pro Gln Arg Lys Ile Glu Glu Asn Lys
465           470             475                 480

Glu Glu Thr Gly Val Lys Lys Ile Glu Leu Val Leu Asn Lys Arg Lys
                485             490                 495

Gly Phe Val Lys Ile Ala Ile Glu Leu Gly Asn Val Ser Leu Val Pro
            500             505                 510

Thr Phe Gly Phe Gly Glu Ala Asp Ile Tyr Arg Ile Thr Lys Pro Lys
            515             520                 525

Pro Gly Ser Phe Gly Glu Met Phe Gln Ser Trp Met Lys Arg Thr Phe
        530             535                 540

Gln Phe Thr Val Pro Phe Phe Ser Ala Arg Gly Val Phe Ile Tyr Asp
545             550             555                 560

Phe Gly Phe Leu Pro Tyr Arg Asn Pro Ile Asn Val Cys Phe Gly Arg
                565             570                 575

Pro Ile His Ile Pro Ala Gly Leu Leu Asp Gln Tyr Lys Glu Pro Glu
            580             585                 590

Thr Glu Lys Asp Glu Lys Glu Lys Glu Lys Asn Val Phe Gln Phe Thr
            595             600                 605

Gln Asp Lys Gln Ala Pro Ala Phe Asn Ile Gln Ser Ile Gln Val Phe
610             615             620

Gln Gly Glu Ala Thr Ile Lys Glu Glu Thr Ser
625             630             635

<210> SEQ ID NO 46
<211> LENGTH: 1908
<212> TYPE: DNA
<213> ORGANISM: Pichia guilliermondii

<400> SEQUENCE: 46

```
atgaccaagg aggttgatga aagcactggg ggtgccagtg atataccaaa tatggttgaa      60
gaagcgaaat catcgagttt tgaccgtgaa actgaagaga atctgctact ggagaccact     120
aaacctgacg agaatctggt accggagagt actaaacatg acgagaaact tgtaccggag     180
atcactaaac atgaagacaa tcccatggaa atgaccaagt ttcccaaaa cacagccacc     240 agtcctatga caggagctgg ttccgaagaa acccgtgatt tgattacaga gaacattgag     300
aaaccagatg agggtgatct gctaattgag cttatttcca agataacga tggtgatgga     360 gatgatgggt tgaaaaatag aaaacaaaaa cgatcttctt ctgaagtgaa aaggctgcgc     420
atgtcgtctc tggctcctaa aggtccaact cctcaaaagc atgaacgtcc caagtatata     480
aatgtggcac ctcttaatat ccccattcga cggcgcttgg agatggtggg gataatctgg     540
cacaccattt gtattcccac gtttgtcagt ttgttttttct tgactttgtc gttgggtccg     600
tttgcttggg tagggtgat attgccgtac ttttatggt ggtatcttat cgatttacat     660
actcctacaa acggtaaggt tgcgtatcgg tctcgcgact ggatgaagaa tttcattgtg     720
tgggattggt tcgttgacta tttttcctatc agggtccaca agtcttgtga ttggagcct     780 acctttagcg atgttattat tgaagacgat gtggtgcccg atgatgaaga agaccttatc     840
tcagagcaat cacgaactgg agtcgataaa cttttcaaat ttttgggggct tcgaaaacgc     900 ttaaatgacg actcggatgc ttcgtcgcag tgctcactgc tgcaagagtc tttaagcaca     960
agacgtaaag tgaaacgtat gtctactggt cctcgctaca tctttggata ccatccccat    1020
```

```
ggagtaattt cgatgggtgt ttttggaact ttcgctacca atgcgttgcg taacgagccg   1080
tacgaacctc ccttgcgttt gctaaagcca tttttccacg actcttccaa gggagaacgg   1140
ttgtttcccg gtattggcac cgtctttcca ttgacattga caacccaatt tattgtgccg   1200
tactaccgtg actatatctt gggcatggga ctcaccagtg cttcggctaa aaacatcaag   1260
agccttataa gcaacggaga caactcgata tgtgtcgttg ttggaggtgc tcaggaatcg   1320
ctcctaaacg atatggtagc cgcaaccaca gttcccggtc gttacggaaa gagcaatttg   1380
cccaatgaca gtgataccga tagcgagttt gatcctcagc gtaagattga agaaaacaag   1440
gaagaaaccg gcgtaaagaa aattgaactt gtacttaata agagaaaggg tttcgtcaag   1500
atagcgattg agttgggcaa cgtttcactc gtgcctacgt ttggttttgg agaagctgac   1560
atctacagaa tcaccaaacc caaaccaggt tcatttggag aaatgttcca atcttggatg   1620
aaacgcacat ttcaattcac ggttccattt ttcagcgcta gaggtgtgtt catttacgac   1680
tttgggtttc ttccttacag aaatcccatc aatgtctgct ttggacggcc cattcatatt   1740
ccagccggct tattggatca atacaaagag cccgaaactg agaaagatga aaaagaaaag   1800
gaaaaaaacg tcttccagtt cactcaagac aaacaagcgc cagccttcaa tatccaatct   1860
attcaagttt tccaagggga agcaaccatc aaagaggaaa cgagttag                 1908
```
<210> SEQ ID NO 47
<211> LENGTH: 370
<212> TYPE: PRT
<213> ORGANISM: Microbotryum violaceum

<400> SEQUENCE: 47

```
Met Thr Ser Leu Arg Asp Val Asn Pro Thr Ser Thr Gln Ala Ser Leu
1               5                   10                  15

Tyr Lys Asp Glu Gly Lys Asp Lys Glu Asp Val Ala Pro Gln Glu Lys
            20                  25                  30

Tyr Thr Gln Ser Leu Arg Thr Asn Ile Lys Phe Ala Pro Leu Ala Val
        35                  40                  45

Pro Arg His Arg Arg Leu Gln Thr Met Ala Val Leu Gly Trp Thr Thr
    50                  55                  60

Ala Leu Pro Leu Met Leu Gly Leu Phe Phe Leu Leu Cys Ser Ile Pro
65                  70                  75                  80

Leu Leu Trp Pro Ile Ile Val Pro Tyr Leu Phe Trp Ile His Leu Ile
                85                  90                  95

Asp Asn Ser Pro Thr Gln Gly Gly Arg Ala Ser Lys Trp Leu Arg Gln
            100                 105                 110

Ser Arg Phe Trp Val Trp Phe Thr Gly Tyr Tyr Pro Ile Ser Leu Val
        115                 120                 125

Lys Thr Val Asp Leu Pro Pro Asp Arg Lys Tyr Val Phe Gly Tyr His
    130                 135                 140

Pro His Gly Ile Ile Gly Met Gly Ala Ile Ala Asn Phe Gly Thr Asp
145                 150                 155                 160

Ala Thr Gly Phe Ser Glu Leu Phe Pro Gly Leu Asn Pro His Leu Leu
                165                 170                 175

Thr Leu Ala Ser Asn Phe Lys Leu Pro Ile Tyr Arg Asp Phe Leu Leu
            180                 185                 190

Ala Leu Gly Ile Cys Ser Val Ser Met Lys Ser Cys Gln Asn Ile Leu
        195                 200                 205

Lys Gln Gly Pro Gly Ser Ala Leu Thr Ile Val Val Gly Gly Ala Ala
```

```
        210                 215                 220
Glu Ser Leu Ser Ala His Pro Gly Thr Ala Asn Leu Thr Leu Arg Arg
225                 230                 235                 240

Arg Met Gly Phe Ile Lys Leu Ala Met Arg Gln Gly Ala Asp Leu Val
                245                 250                 255

Pro Val Phe Ser Phe Gly Glu Asn Asp Ile Phe Glu Gln Met Pro Asn
                260                 265                 270

Glu Arg Gly Thr Lys Leu Tyr Lys Met Gln Lys Lys Phe Gln Thr Ala
                275                 280                 285

Phe Gly Phe Thr Leu Pro Ile Phe His Gly Arg Gly Ile Phe Asn Tyr
                290                 295                 300

Asn Leu Gly Ile Leu Pro Tyr Arg His Pro Ile Val Ser Val Val Gly
305                 310                 315                 320

Arg Pro Ile Arg Val Ser Gln Arg Asp Asn Pro Thr Lys Glu Glu Leu
                325                 330                 335

Glu Glu Val Gln Glu Arg Tyr Ile Glu Glu Leu Lys Arg Ile Trp Asp
                340                 345                 350

Asp Tyr Lys Asn Gln His Ala Ile Lys Arg Lys Gly Glu Leu Arg Ile
                355                 360                 365

Ile Ala
    370

<210> SEQ ID NO 48
<211> LENGTH: 1113
<212> TYPE: DNA
<213> ORGANISM: Microbotryum violaceum

<400> SEQUENCE: 48
atgacgtcgc tgcgagacgt gaacccgacc tcgacccaag catcgttgta caaagacgag      60
ggcaaggaca aggaggatgt cgcaccgcag agaaatacac gcagtcgct ccggaccaac      120 atcaaatttg cacctctagc tgtaccacgc catcgacgac tgcagaccat ggcagtgttg      180
ggatggacga ccgcactgcc actcatgctt ggtttgttct ttctattgtg ctcaatcccc      240
cttctatggc ccatcatcgt gccctatctc ttctggatcc acctcatcga caactcgccg      300
acgcagggag gacgagcgag caaatggctt cgccaaagtc ggttctgggt gtggttcaca      360
gggtactatc ctatcagtct cgtcaagacg gtcgatttac ctccagatcg gaaatacgtc      420
ttcggttacc accccatgg cataattgga atgggtgcaa ttgccaattt tgggaccgac      480
gccactgggt tctctgagct cttcccagga ctcaaccctc atctcctcac acttgccagc      540
aacttcaaat tgccgatata tcgagacttc ttgcttgcgc tcggcatctg ctcagtcagt      600
atgaaatctt gccaaaacat cctcaaacag ggcccgggt ctgctttgac cattgtcgtc      660
ggaggagctg cggaatccct ttcggcgcat cctggcacag ccaacttgac actccgtcgc      720
cgaatgggct tcatcaagct ggcgatgcgt caaggcgcgg atcttgtacc cgtcttttca      780
ttcggagaga acgatatctt cgaacagatg ccgaacgaga gagggacgaa gctgtacaag      840
atgcaaaaga gtttcagac cgcttttgga ttcactctac cgatcttcca cggccgagga      900
atttttaact ataaccttgg catcttgccg taccgtcatc cgatcgtgtc ggtcgtcggt      960
cggcccatcc gcgtttcgca gcgtgacaac cctactaagg aggaactcga ggaggtgcag     1020
gaacgatata tcgaggagtt gaagagaatc tgggacgatt acaaaaatca acatgccatc     1080
aagcgaaagg gcgaacttcg tattattgcc tga                                  1113
```

<210> SEQ ID NO 49
<211> LENGTH: 365
<212> TYPE: PRT
<213> ORGANISM: Puccinia graminis

<400> SEQUENCE: 49

```
Met Lys Asp Asp Ser Arg Ser Pro Ser Gly Ser Glu Pro Glu Gly Asp
1               5                   10                  15

Asn His Lys Lys Glu Lys Arg Pro Ile Trp Ala Pro Ile Arg Val Pro
            20                  25                  30

Pro Tyr Arg Arg Ile Gln Thr Ala Ala Val Leu Leu Trp Thr Ser Gln
        35                  40                  45

Leu Ser Leu Cys Ile Ser Leu Phe Phe Phe Leu Met Ser Tyr Pro Ile
    50                  55                  60

Thr Trp Pro Ile Leu Leu Pro Tyr Val Ile Trp Ile Leu Val Ile Asp
65                  70                  75                  80

Pro Ala Pro Glu Lys Gly Gly Arg Leu Asn Gln Ser Val Arg Thr Trp
                85                  90                  95

Lys Phe Trp Asn Leu Phe Ala Ser Tyr Phe Pro Ile Ser Leu Ile Lys
            100                 105                 110

Thr Val Asp Leu Pro Ser Asp Arg Lys Tyr Val Phe Gly Tyr His Pro
        115                 120                 125

His Gly Ile Ile Gly Met Gly Ala Val Ala Asn Phe Gly Thr Glu Ala
    130                 135                 140

Thr Gly Phe Ser Glu Lys Phe Pro Gly Leu Asn Pro His Leu Leu Thr
145                 150                 155                 160

Leu Ser Thr Asn Phe Ile Ile Pro Phe Tyr Arg Asp Leu Ile Leu Ser
                165                 170                 175

Leu Gly Ile Cys Ser Val Ser Ile Lys Ser Cys Ile Ser Ile Leu Lys
            180                 185                 190

Ser Lys Asn Lys Arg Ser Ala Asp Val Lys Asn Asn Lys Gly Glu Gly
        195                 200                 205

Asn Cys Leu Val Ile Val Val Gly Gly Ala Ala Glu Ser Leu Ser Ala
    210                 215                 220

His Pro Gly Thr Ala Asp Leu Thr Leu Lys Arg Arg Leu Gly Phe Ile
225                 230                 235                 240

Lys Leu Ala Ile Arg Glu Gly Ala Asp Leu Val Pro Val Phe Ser Phe
                245                 250                 255

Gly Glu Asn Asp Ile Tyr Ala Gln Leu Ser Asn Ser Lys Gly Thr Ala
            260                 265                 270

Leu Tyr Ser Leu Gln Lys Arg Phe Gln Ala Val Phe Gly Phe Thr Leu
        275                 280                 285

Pro Val Phe His Gly Arg Gly Ile Phe Asn Tyr Ser Leu Gly Leu Leu
    290                 295                 300

Pro Tyr Arg His Pro Ile Val Ser Val Val Gly Lys Pro Ile Arg Val
305                 310                 315                 320

Glu Gln Asn Lys Asn Pro Gly Leu Glu Glu Ile Glu Lys Val Gln Lys
                325                 330                 335

Glu Tyr Ile Ala Glu Leu Thr Ala Val Trp Asp Gln Tyr Lys Asp Leu
            340                 345                 350

Tyr Ala Arg Asn Arg Lys Ser Glu Leu Thr Leu Ile Ala
        355                 360                 365
```

<210> SEQ ID NO 50
<211> LENGTH: 1098

<212> TYPE: DNA
<213> ORGANISM: Puccinia graminis

<400> SEQUENCE: 50
atgaaggatg actccagaag cccgtctggg tccgaacccg agggcgataa tcacaagaag 60
gagaaaaggc caatctgggc tccgattcgt gtacctcctt acaggcgcat ccaaacggcc 120
gcagtactct tatggacttc tcaactctca ctatgcattt ccttattctt tttcttaatg 180
tcttacccga tcacctggcc gatcctcctt ccatacgtta tttggatctt ggtcatagat 240
cctgctcccg agaagggtgg ccggttgaat caatctgttc ggacctggaa gttttggaat 300
ctatttgcgt cgtatttccc aatcagttta atcaaaactg ttgatttgcc cagtgaccgc 360
aaatatgtct ttggttacca ccctcatggt atcatcggaa tgggcgcggt ggccaacttt 420
ggaacggaag cgacaggatt ttcggaaaaa ttccctggtc tcaatccaca tctactcaca 480
ttgagcacga actttatcat cccattctat cgagacctga tcctcagtct tggaatctgt 540
tcggtgtcga tcaaatcatg catctcgatc ctcaaatcca aaaacaaacg ctcagctgat 600
gtcaagaaca ataagggcga aggaaattgt ttggttatcg ttgtcggtgg ggctgcggaa 660
agtttgtctg ctcatcctgg aacagccgat ctcactctaa aacgacggct gggtttcatc 720
aaactggcca ttcgagaagg agccgatctc gtccctgtgt tctcctttgg agagaatgac 780
atttacgccc aattatcaaa ctcaaaaggc acggcactct actctcttca aaaacgattt 840
caagctgtat ttggctttac cttacctgtt ttccatggcc gaggtatctt caactactct 900
ctcggcttgc ttccctatcg acacccgatt gtttcagtag ttggtaaacc tattcgagtc 960
gagcaaaata aaaaccccgg gctcgaagaa atcgaaaagg ttcagaaaga atacattgct 1020
gaacttaccg cagtatggga tcagtataaa gatttatacg ctagaaatcg gaagagtgaa 1080
ttgactttga ttgcttag 1098

<210> SEQ ID NO 51
<211> LENGTH: 373
<212> TYPE: PRT
<213> ORGANISM: Gloeophyllum trabeum

<400> SEQUENCE: 51

Met Asp Ala Gly Arg Ala Phe Ser Ser Ala Ser Arg Ser Leu Ser Ser
1 5 10 15

Ser Ser Leu Lys Asp Lys Leu Ser Lys Val Ser Lys Leu Ser Thr Thr
20 25 30

Pro Leu Arg Pro Val Ala Ala His Val Lys Asn Ile Asp Phe Val Pro
35 40 45

Ser Lys Ile Pro Arg Lys Arg Arg Leu Gln Met Leu Ala Val Ala Val
50 55 60

Trp Ala Leu Leu Ile Pro Ile Thr Thr Phe Leu Phe Leu Ile Leu Cys
65 70 75 80

Ser Phe Pro Pro Leu Trp Pro Phe Leu Ala Ala Tyr Leu Ile Trp Ile
85 90 95

Arg Trp Ile Asp Arg Ser Pro Glu His Gly Gly Arg Ile Ser Pro Trp
100 105 110

Phe Arg Ser Met Arg Phe Trp Arg Tyr Phe Ala Asp Tyr Tyr Pro Ala
115 120 125

Ser Phe Leu Lys Glu Cys Asp Leu Pro Pro Asp Arg Pro Tyr Val Phe
130 135 140

Gly Tyr His Pro His Gly Ile Ile Gly Met Gly Ala Met Ala Thr Phe

```
145                 150                 155                 160
Ala Thr Glu Ala Thr Gly Phe Ser Glu Gln Phe Pro Gly Leu Thr Pro
                165                 170                 175

His Leu Leu Thr Leu Ala Thr Asn Phe Thr Met Pro Ile Tyr Arg Asp
            180                 185                 190

Ile Ile Leu Ala Leu Gly Ile Cys Ser Val Ser Lys Gln Ser Cys Ser
            195                 200                 205

Asn Ile Leu Ser Ser Gly Pro Gly Gln Ala Ile Thr Ile Val Val Gly
    210                 215                 220

Gly Ala Glu Ser Leu Ser Ala Arg Pro Gly Thr Ala Asp Leu Thr
225                 230                 235                 240

Leu Lys Arg Arg Leu Gly Phe Ile Lys Ile Ala Ile Gln His Gly Ala
                245                 250                 255

Ala Leu Val Pro Val Phe Ser Phe Gly Glu Asn Asp Ile Tyr Gln Gln
                260                 265                 270

Met Pro Asn Glu Lys Gly Thr Thr Ile Tyr Ala Leu Gln Lys Lys Phe
            275                 280                 285

Gln Ser Val Phe Gly Phe Thr Leu Pro Leu Phe His Gly Arg Gly Met
    290                 295                 300

Leu Asn Tyr Asn Leu Gly Leu Met Pro Tyr Arg Arg Ile Val Ser
305                 310                 315                 320

Val Ile Gly Arg Pro Ile Leu Cys Glu Lys Cys Glu Lys Pro Ser Met
                325                 330                 335

Glu Glu Val Thr Arg Val Gln Gln Glu Tyr Ile Ala Glu Leu Leu Arg
            340                 345                 350

Ile Trp Asp Thr Tyr Lys Asp Gln Phe Ala Arg Ser Arg Lys Arg Glu
    355                 360                 365

Leu Ser Ile Ile Asp
        370

<210> SEQ ID NO 52
<211> LENGTH: 1122
<212> TYPE: DNA
<213> ORGANISM: Gloeophyllum trabeum

<400> SEQUENCE: 52
atggacgctg tcgcgccctt ctcctctgca tcccgctcgt tatcgtcctc gtccctgaag      60
gacaagctgt caaaggtctc gaagctcagc accactcctc tgcgaccggt cgctgcccat     120
gtcaagaata tcgacttcgt cccgtccaag atccccggga acggaggct gcagatgctc      180 gctgttgcag tatgggcgct cctgataccc atcacgacgt ttttgttcct catactatgt     240
tcttttccac cgctgtggcc attttttagcg gcgtatctta tatggataag atggatagac     300
cggagtcctg agcatggcgg aggataagt ccgtggttcc gctcgatgag gttctggaga      360
tactttgccg actactaccc tgcatcgttc ttgaaggaat gcgacctccc cccagaccga     420
ccttacgtct tcgggtatca ccctcatggc atcattggca tgggtgccat ggccactttc     480
gccaccgaag ccactggatt cagcgaacag ttccctgggc tcactcccca cctgctcacc     540
ctagccacaa atttcaccat gcccatatac agagacatca tcctcgccct gggcatatgc     600
tccgtcagca agcagtcctg ctcgaacatc ctcagcagcg ccccgggca ggctatcaca      660 atcgtagtag gaggcgcagc agagagtctt agcgctcggc cgggcacggc cgacctcacg     720
ctcaaacgga ggcttggctt catcaagatt gctatacaac acggagcggc actggtccct     780 gtatttctctt tcggcgagaa tgatatttat caacaaatgc ccaacgaaaa gggaaccaca     840
```

```
atatatgccc tacagaagaa attccagagc gtcttcggct tcacgttgcc cttgttccac    900
ggtcggggca tgctaaatta taaccttggt ttgatgccgt atcgacggcg gatcgtgtct    960
gtcatcggtc ggcccatatt atgcgagaag tgcgagaagc caagcatgga ggaggttacg   1020
cgggtgcaac aggagtacat cgcagagctg ctcagaatat gggacacgta caaagatcaa   1080
tttgctcggt cgcggaagag agaactgagt attattgatt ga                      1122
```

<210> SEQ ID NO 53
<211> LENGTH: 346
<212> TYPE: PRT
<213> ORGANISM: Rhodosporidium diobovatum

<400> SEQUENCE: 53

```
Met Gly Ala Leu Asp Ala Gly Asp His Glu Gly Thr Glu His Pro Lys
1               5                   10                  15

Ile Lys Phe Val Pro Phe Val Pro Arg His Arg Arg Leu Gln Thr
            20                  25                  30

Phe Ser Val Phe Leu Trp Thr Thr Ala Leu Pro Leu Ser Leu Gly Ile
        35                  40                  45

Phe Cys Ile Leu Cys Ser Phe Pro Pro Leu Trp Pro Leu Val Ile Gly
    50                  55                  60

Tyr Leu Thr Trp Val Phe Leu Ile Asp Gln Ala Pro Met Arg Gly Gly
65                  70                  75                  80

Arg Pro Gln Ala Trp Leu Arg Lys Ser Arg Val Trp Glu Trp Phe Ala
                85                  90                  95

Gly Tyr Tyr Pro Val Ser Leu Ile Lys Ser Ala Asp Leu Pro Pro Asp
            100                 105                 110

Gln Arg Tyr Val Phe Gly Tyr His Pro His Gly Val Ile Gly Met Gly
        115                 120                 125

Ala Ile Ala Asn Phe Gly Thr Asp Ala Thr Gly Phe Ser Arg Leu Phe
    130                 135                 140

Pro Gly Ile Lys Pro His Leu Leu Thr Leu Ala Ser Asn Phe Lys Leu
145                 150                 155                 160

Pro Leu Tyr Arg Glu Leu Leu Leu Ala Leu Gly Ile Ser Ser Val Ser
                165                 170                 175

Met Lys Ser Cys Gln Asn Ile Leu Arg Gln Gly Pro Gly Ser Ser Ile
            180                 185                 190

Thr Ile Val Val Gly Gly Ala Ala Glu Ser Leu Ser Ala His Pro Gly
        195                 200                 205

Thr Ala Asp Leu Thr Leu Lys Arg Arg Lys Gly Phe Ile Lys Leu Ala
    210                 215                 220

Ile Arg Ser Gly Ala Tyr Leu Val Pro Val Phe Ser Phe Gly Glu Asn
225                 230                 235                 240

Asp Ile Phe Asn Gln Leu Ser Asn Glu Arg Gly Thr Arg Leu Tyr Lys
                245                 250                 255

Leu Gln Lys Arg Phe Gln Ala Val Phe Gly Phe Thr Leu Pro Ile Phe
            260                 265                 270

Phe Gly Arg Gly Leu Phe Asn Tyr Asn Met Gly Leu Met Pro Tyr Arg
        275                 280                 285

His Pro Ile Val Ser Val Val Gly Arg Pro Ile Lys Val Thr Gln Lys
    290                 295                 300

Asp His Pro Ser Thr Ala Asp Leu Glu Glu Val Gln Asp Arg Tyr Ile
305                 310                 315                 320
```

-continued

```
Ala Glu Leu Lys Arg Ile Trp Glu Asp Tyr Lys Glu Val Tyr Ala Lys
                325                 330                 335
Ser Arg Thr Lys Glu Leu Thr Ile Ile Ala
        340                 345
```

<210> SEQ ID NO 54
<211> LENGTH: 1041
<212> TYPE: DNA
<213> ORGANISM: Rhodosporidium diobovatum

<400> SEQUENCE: 54

| | | | | | |
|---|---|---|---|---|---|
| atgggagcac | tagatgcggg | cgaccacgag | gggaccgaac | accccaagat | caagttcgtt | 60 |
| cctttcgttg | tgccgcgaca | ccgcaggctg | cagaccttt | cggtgtttct | gtggacgacc | 120 |
| gcgctgcctc | tgtcgctcgg | catcttctgc | attctctgct | ccttcccccc | actctggccc | 180 |
| ctcgtcatag | ggtatctcac | gtgggtattc | ctcatcgacc | aggcgcccat | gcggggtggc | 240 |
| aggcctcagg | cctggttgcg | caagtcgcgt | gtgtgggagt | ggttcgccgg | ctactaccct | 300 |
| gtcagcttga | tcaagagcgc | cgacctcccg | cccgaccagc | gctacgtctt | tggctaccac | 360 |
| ccacacggcg | tcattgggat | gggcgccatc | gccaactttg | gtaccgacgc | gaccggcttc | 420 |
| tcgcggctgt | tccccggcat | caagccgcac | tcctcacgc | tcgccagcaa | cttcaagctg | 480 |
| ccgctctacc | gagaactgct | cctcgccttg | gcatttcgt | ccgtgtcgat | gaagagctgc | 540 |
| cagaacatcc | tgcgccaagg | tcccggctcg | tcgatcacga | ttgtcgtcgg | aggggcagca | 600 |
| gaaagcctca | gcgcgcaccc | gggaacggca | gacctgacgc | tcaagcggcg | gaaggggttc | 660 |
| atcaagctcg | cgatccgctc | aggggcctac | ctcgtcccgg | tattttcctt | tggcgagaat | 720 |
| gacatcttca | accagctgtc | gaatgagcgc | ggcacccgac | tctacaagct | gcaaaagcgg | 780 |
| ttccaggccg | tctttggctt | caccttgccc | atcttcttcg | gtcgcggcct | cttcaactac | 840 |
| aacatgggct | tgatgccata | tcgacacccg | atcgtctcgg | tcgtcggacg | ccccatcaag | 900 |
| gtcacgcaga | aggatcaccc | gtcgacggcc | gacctcgaag | aggtacagga | ccgctacatt | 960 |
| gccgagttga | agaggatctg | ggaggactac | aaagaggtgt | acgccaagag | ccgcaccaag | 1020 |
| gagctcacca | tcatcgcatg | a | | | | 1041 |

<210> SEQ ID NO 55
<211> LENGTH: 359
<212> TYPE: PRT
<213> ORGANISM: Phaeodactylum tricornutum

<400> SEQUENCE: 55

```
Met Lys Glu Arg Arg Ser Gly Leu Asn Pro Ser Gly Ser Ser Val Tyr
1               5                   10                  15
Pro Leu His Pro Pro Asp Ser Arg Val Leu Val Arg Val Pro Ser Asp
            20                  25                  30
Ile Ser Phe Leu Asp Arg Leu Ile Val Ala Gly Ser Ser Ile Phe Ile
        35                  40                  45
Val Gly Ser Leu Val Trp Val Pro Leu Thr Ala Arg Trp Val Tyr Arg
    50                  55                  60
Arg Trp Lys Gln Ala Lys Asp Lys Arg Lys Ala Met Tyr Ala Ser
65                  70                  75                  80
Leu Leu Val Ile Leu Ala Val Leu Val Ile Gly Gly Pro His Arg Ser
                85                  90                  95
Pro Arg Val Gly Lys Trp Leu Gln Val Arg Lys Trp Ser Leu Phe Gln
            100                 105                 110
```

Ala Trp Val Lys Phe Ile Ala Met Glu Val Ile Leu Asp Gln Pro Lys
        115                 120                 125

Gly Ile Thr Met Asp Val Gln Gln Asp Lys Ala Ile Phe Ala Phe Ala
    130                 135                 140

Pro His Gly Ile Phe Pro Phe Ala Phe Ala Phe Gly Val Leu Pro Asp
145                 150                 155                 160

Ile Ala Thr Gln Ser Phe Gly Tyr Val Arg Pro Val Val Ala Thr Ala
                165                 170                 175

Thr Arg Leu Phe Pro Val Val Arg Asp Phe Ile Ser Trp Ala Asn Pro
            180                 185                 190

Val Asp Ala Ser Lys Asp Ser Val Glu Arg Ala Leu Ala Leu Gly Asp
        195                 200                 205

Arg Ile Ala Val Ile Pro Gly Gly Ile Ala Glu Ile Phe Glu Gly Tyr
210                 215                 220

Pro Lys Pro Asn Thr His Pro Asp Glu Glu Tyr Ala Ile Val Arg Ser
225                 230                 235                 240

Gly Phe Leu Arg Leu Ala Ile Lys His Gly Ile Pro Val Ile Pro Val
                245                 250                 255

Tyr Cys Phe Gly Ala Thr Lys Met Leu Lys Arg Leu Glu Leu Pro Gly
            260                 265                 270

Leu Glu Gln Leu Ser Leu Phe Leu Arg Val Ser Ile Cys Leu Phe Phe
        275                 280                 285

Gly Val Gly Gly Leu Pro Ile Pro Phe Arg Gln Arg Leu Ser Tyr Val
290                 295                 300

Met Gly Gln Pro Ile Leu Pro Pro Val Arg Thr Thr Gly Ser Asp Ile
305                 310                 315                 320

Ser Asp Ala His Val Lys Glu Met Gln Asp Arg Phe Cys Ala Glu Val
                325                 330                 335

Gln Arg Leu Phe Asp Arg His Lys Glu Ala Tyr Gly Trp Ser Tyr Lys
            340                 345                 350

Thr Leu Lys Leu Leu Glu Gln
        355

<210> SEQ ID NO 56
<211> LENGTH: 1080
<212> TYPE: DNA
<213> ORGANISM: Phaeodactylum tricornutum

<400> SEQUENCE: 56
atgaaagaaa aagatctgg cctaaatccg tcaggatcct ccgtgtatcc attgcaccct      60
cctgacagtc gcgttctcgt tcgagtcccc tccgatattt cctttcttga tcgtctcatc    120
gtcgctggca gcagtatctt tattgtcggt tcgctagtat gggttccatt gaccgcaaga    180
tgggtctaca ggcggtggaa gcaagctaaa gataaacgaa agcgggctat gtatgcctct    240
ctactcgtga ttctggcagt tctcgttatt ggcggacccc accgatctcc tcgtgtcggc    300
aaatggctcc aagtacgaaa gtggtccctc ttccaagcgt gggtaaagtt tattgccatg    360
gaagtgattt tggatcaacc gaaaggcatt actatggacg tccaacaaga caaggcgatt    420
tttgcattcg cgccacatgg aatctttccg tttgcgttcg cctttggagt gcttcccgat    480
attgccacac aatcgtttgg ctacgttcgt ccggtcgtgg caaccgccac aaggttgttt    540
cctgtagtcc gggatttcat ctcttgggcg aatccggtag acgcttccaa agattccgtt    600
gaacgtgctt tagcattggg cgatcgcatt gctgtaatac ctggaggaat tgcagaaatt    660
ttcgaaggat atccgaaacc gaacacgcat ccggatgaag agtacgctat cgtacggagt    720

```
ggattttttgc gtttggcaat aaaacacggt atcccagtga ttcccgtata ctgtttcggc    780
gctaccaaaa tgttgaagcg tctggagctt cccggcctgg agcaactgtc cctgtttcta    840
cgcgtgagca tttgcctctt ttttggagtc ggcgggttgc ccatcccttt ccgacaacga    900
ttgtcgtacg taatgggaca accaattttg ccacccgtaa ggacaacggg cagcgatatt    960
tcggacgcac acgtcaaaga aatgcaagat cgcttttgtg ctgaggtcca gcggctcttt   1020
gatcgacata aggaagctta tggttggtca tacaaaacgc tgaaactatt ggaacagtga   1080
```

<210> SEQ ID NO 57
<211> LENGTH: 329
<212> TYPE: PRT
<213> ORGANISM: Phaeodactylum tricornutum

<400> SEQUENCE: 57

```
Met Glu Arg Thr Lys Ile Gln Asp Glu His Lys Ser Pro Pro Asn Pro
1               5                   10                  15

Ser Thr Phe Arg Trp Phe Leu Gly Leu Leu Val Ala Ser Thr Phe Ser
            20                  25                  30

Met Val Tyr Phe Val Ala Pro Phe Tyr Met Leu Thr Val Val Phe Ala
        35                  40                  45

Leu Val Phe Lys Tyr Pro Ser Val Glu Ile Ala Trp Met Tyr Ala Ile
    50                  55                  60

Pro Met Ile Val Ser Ala Ile Leu Pro Pro Met Ala Ser Pro Leu Ala
65                  70                  75                  80

Leu Arg Leu Ile Ser Pro Leu Ile Asp Tyr Phe Asp Tyr Glu Glu Ile
                85                  90                  95

His Glu Thr Ser Pro Val Asp Val Gln Lys Glu Ile Leu Ser Asn Asn
            100                 105                 110

Lys Asn Tyr Leu Leu Val Phe Gln Pro His Gly Ala Leu Ser Phe Thr
        115                 120                 125

Gly Ile Thr Ser Met Val Thr Ala Pro Gln Ala Met Lys Gly Lys Leu
    130                 135                 140

Pro Thr Ala Val Ala Asp Ala Leu Leu Tyr Thr Pro Ile Leu Lys His
145                 150                 155                 160

Val Leu Gly Ile Phe Gly Leu Ile Ser Ala Ser Lys Ser Ser Met Ile
                165                 170                 175

Arg Thr Leu Lys Lys Gly Val Glu Gly Thr Ile Val Leu Tyr Val
            180                 185                 190

Gly Gly Ile Ala Glu Leu Phe Leu Thr Asp Glu Thr Asp Glu Arg Leu
    195                 200                 205

Tyr Leu Arg Lys Arg Lys Gly Phe Ile Lys Leu Ala Leu Gln Gln Gly
    210                 215                 220

Val Asp Val Val Pro Val Tyr Leu Phe Gly Asn Thr Asn Ala Leu Ser
225                 230                 235                 240

Val Leu Lys Thr Gly Phe Leu Ala Ala Ile Ser Arg Lys Leu Gln Ile
                245                 250                 255

Ser Leu Thr Tyr Ile Trp Gly Lys Trp Tyr Leu Pro Ile Pro Arg Asp
            260                 265                 270

Cys Lys Leu Leu Tyr Ala Ser Gly Gln Pro Leu Gly Met Pro His Ile
        275                 280                 285

Leu Asp Pro Ser Gln Ala Asp Ile Asp Lys Trp His Glu Lys Tyr Cys
    290                 295                 300

Ser Glu Val Met Arg Ile Phe Glu Lys Tyr Lys Glu Lys Val Pro Glu
```

Tyr Lys His Lys Lys Leu Glu Ile Ile
            325

<210> SEQ ID NO 58
<211> LENGTH: 990
<212> TYPE: DNA
<213> ORGANISM: Phaeodactylum tricornutum

<400> SEQUENCE: 58

| | | | | | |
|---|---|---|---|---|---|
| atggagagaa | caaagataca | agacgagcac | aaaagtcccc | ctaatccgtc | gacatttcga | 60 |
| tggttcctcg | gccttctagt | ggcgtcgacg | ttttccatgg | tctattttgt | ggctcccttt | 120 |
| tacatgctta | cagtcgtgtt | tgcactagtt | ttcaaatatc | cttcggtaga | aattgcatgg | 180 |
| atgtacgcta | ttccgatgat | tgtctcggcc | attttgccac | caatggcttc | tccactggcc | 240 |
| ttgcgactca | tctccccgct | cattgactac | ttcgattacg | aagagatcca | cgaaacctca | 300 |
| ccggtggacg | tccagaagga | aatactaagc | aacaacaaaa | actatttgct | agtctttcaa | 360 |
| ccgcatggag | cactgtcgtt | tacaggaatc | acttcaatgg | tgacagctcc | acaagcaatg | 420 |
| aaaggcaaat | tgccaacagc | tgtggctgac | gcactcttgt | acacacctat | actgaaacat | 480 |
| gtcttaggaa | ttttcgggct | gattagtgcc | tccaaaagca | gcatgatccg | aactttaaaa | 540 |
| aagaagggtg | tggaaggaac | cattgttttg | tacgttggtg | ggattgccga | gctctttttg | 600 |
| accgacgaga | cggacgagcg | cctctatctg | cgaaagcgaa | aagggtttat | caaattagct | 660 |
| ctacaacagg | gtgtcgatgt | tgtacctgtg | tatctatttg | ggaacacaaa | cgcgctgtcg | 720 |
| gtactaaaga | cgggatttct | cgcggcaatt | tcgcgaaaat | tacagatatc | tctgacgtac | 780 |
| atttggggaa | agtggtatct | tccgattccc | cgtgattgca | aattgctgta | tgcttccggt | 840 |
| cagccattag | gaatgcctca | tattttagac | ccaagccaag | ccgacattga | taaatggcac | 900 |
| gaaaagtact | gctccgaggt | catgcggatc | ttcgaaaaat | acaaggaaaa | ggttccggaa | 960 |
| tacaagcaca | agaaattaga | aattatttga | | | | 990 |

<210> SEQ ID NO 59
<211> LENGTH: 392
<212> TYPE: PRT
<213> ORGANISM: Phaeodactylum tricornutum

<400> SEQUENCE: 59

Met Arg Glu Arg Ser Cys Ala Asn Ala Ser Asp Asp Ser Ile His
1               5                   10                  15

Lys Gln Ser Pro Glu Leu Glu Ala Glu Phe Leu His Thr Ser Lys Leu
            20                  25                  30

Thr Leu Ala Asp Met Arg Arg Leu Ala His Asp Pro Lys Asp Arg Gly
        35                  40                  45

Leu Ala Thr Lys Pro Ala Ala Gln Ala Thr Lys Glu Asp Val Leu Thr
    50                  55                  60

Val Gln Pro Met Ser Phe Val Glu His Thr Ala Cys Cys Leu Phe Leu
65                  70                  75                  80

Ala Phe Gly Val Pro Asn Gly Ala Leu Thr Ile Pro Ile Ala Thr Trp
                85                  90                  95

Leu Ile Gly Lys Phe Val Leu Arg Asn Val Phe Leu Ala Phe Leu Leu
            100                 105                 110

Ala Gly Cys Ile Leu Leu Pro Leu Ala Ile Leu Pro Gln Glu Tyr Val
        115                 120                 125

```
Pro Ala Arg Leu Gln Ser Trp Leu Ala Leu Gln Ile Leu Lys Tyr Phe
    130                 135                 140
Ser Phe Ser Leu Val Met Glu Glu Arg Pro Pro Thr Met Cys Thr Gly
145                 150                 155                 160
Lys Gln Leu Ile Glu Gln Pro Ala Arg Pro Arg Ile Val Thr Ala Tyr
                165                 170                 175
Pro His Gly Val Phe Pro Tyr Gly Asn Ala Leu Thr Val Val Thr Trp
                180                 185                 190
Pro Leu Leu Thr Gly His His Ile Val Gly Leu Ala Ala Asn Ala Ala
                195                 200                 205
Leu Arg Thr Pro Ile Phe Lys Gln Ile Leu Arg Ser Ile Gly Val Lys
    210                 215                 220
Asp Ala Ser Arg Ala Ser Val Arg Asn Ala Leu Glu Thr Trp Pro Phe
225                 230                 235                 240
Thr Val Gly Ile Ser Pro Gly Gly Val Ala Glu Val Phe Glu Thr Asn
                245                 250                 255
His Phe Asn Glu His Ile Leu Leu Lys Glu Arg Ile Gly Val Ile Lys
                260                 265                 270
Met Ala Ile Arg Thr Gly Ala Asp Leu Val Pro Gly Tyr Met Tyr Gly
    275                 280                 285
Asn Thr Asn Leu Tyr Trp Cys Trp Thr Gly Glu Gly Ile Pro Gly Ala
290                 295                 300
Arg Trp Leu Leu Glu Tyr Val Ser Arg Lys Ile Leu Gly Phe Ala Leu
305                 310                 315                 320
Val Pro Ile Ala Gly Arg Trp Arg Leu Pro Ile Pro Tyr Arg Thr Pro
                325                 330                 335
Ile Leu Cys Val Val Gly Lys Pro Ile Pro Thr Ile His Leu Gln Thr
                340                 345                 350
Glu Glu Pro Ser Met Glu Gln Ile Val Asp Ile Gln Glu Gln Leu Ser
    355                 360                 365
Thr Glu Leu Lys Ser Met Phe Asp Arg Tyr Lys His Leu Tyr Gly Trp
    370                 375                 380
Glu Asp Arg Met Leu Val Ile Thr
385                 390

<210> SEQ ID NO 60
<211> LENGTH: 1179
<212> TYPE: DNA
<213> ORGANISM: Phaeodactylum tricornutum

<400> SEQUENCE: 60
atgcgtgagc gaagctgcgc caacgcttct gacgatgaca gcattcacaa gcagtcgcca      60
gaattggagg ctgagtttct tcataccagc aagttgacct tagccgacat gcgacgattg     120
gcgcacgatc cgaaggatcg ggggttggca acaaaacctg cggcgcaagc tacgaaagaa     180
gacgtcttga cggtacaacc catgagtttc gtagaacaca ctgcttgctg tctgtttctc     240
gcgtttggag tgcccaatgg cgctctgacg attcccatag caacgtggct gatcggaaaa     300
ttcgtgttgc gcaacgtttt cttggcgttt ctgttagcag gctgtatact tctaccgctt     360
gcgatactgc cgcaagaata tgtgcccgcc cgattgcaat cgtggcttgc tttgcagata     420
ctgaaatatt tttctttctc tttggtcatg gaggaacgcc ctccgacaat gtgtactggc     480
aagcagctga tcgagcagcc cgctcggcca cgaatcgtca cagcctatcc gcacggagtt     540
ttcccatacg gaaacgcgtt gactgtagtc acatggccgt tgttgacggg acaccatatt     600
```

```
gtgggtttgg cagcaaatgc cgctttgcgg acaccgatct ttaaacaaat cttgcggagc    660
attggcgtca aggacgcctc tcgagcgtcg gtacggaatg cgctggaaac atggcctttc    720
accgtcggga tttcgccagg tggcgtggcg gaagttttg aaacaaacca cttcaatgag     780
cacattctgt tgaaagaacg tattggtgtc atcaagatgg ccattcgcac cggtgcggat    840
cttgtaccag gctatatgta tggtaatact aatctgtact ggtgctggac aggggaaggt    900
attcctggag ctcggtggct attggagtat gtttcgcgta aaatcctagg ttttgccctc    960
gtgcctatag cgggtagatg gagactacca ataccgtaca ggactccgat attgtgtgtc   1020
gtgggcaagc caataccaac cattcatttg caaaccgaag aaccatcaat ggagcaaatc   1080
gtggacattc aggaacaatt gtcaacagaa ttgaaatcaa tgttcgaccg ctataagcac   1140
ctgtacggat gggaagatcg aatgctagtg atcacataa                          1179
```

<210> SEQ ID NO 61
<211> LENGTH: 320
<212> TYPE: PRT
<213> ORGANISM: Phaeodactylum tricornutum

<400> SEQUENCE: 61

```
Met Thr Arg Ser Lys Phe Ile Gly Ser Ala Gly Ala Ile Gly Leu Phe
1               5                   10                  15

Cys Leu Met Ile Ile Pro Asn Val Gly Ile Leu Ile Ala Thr Phe Leu
            20                  25                  30

Tyr Pro Lys Val Leu Gly Leu Tyr Phe Leu Ile Pro Tyr Tyr Ala Tyr
        35                  40                  45

Asn Leu Ser Ile Gly Lys His Glu Ala Arg Asp Gly Asn Gly Trp Asn
    50                  55                  60

Trp Phe Ser Glu Asn Phe Phe Val Phe Asn Ile Val Arg Gly Tyr Leu
65                  70                  75                  80

Asn Leu Lys Ile Glu Ala Asp Ser Glu Leu Lys Glu Ala Glu Ala Lys
                85                  90                  95

Glu Gly Ala Gln Phe Val Phe Ala Val Ser Pro His Gly Thr Asn Ala
            100                 105                 110

Asp Tyr Arg Val Phe Ile Asp Gly Met Leu His Glu Ala Leu Pro Gln
        115                 120                 125

Thr Ala Ser Lys Ile Arg Thr Leu Ala Ala Thr Val Leu Phe His Ile
    130                 135                 140

Pro Leu Val Arg Glu Ile Ala Leu Trp Thr Gly Cys Val Asp Ala Ser
145                 150                 155                 160

Arg Ala Val Ala Val Glu Arg Leu Lys Glu Glu Gly Gly Ser Leu Leu
                165                 170                 175

Val Ile Pro Gly Gly Gln Ala Glu Gln Met Tyr Thr Gln Tyr Gly Arg
            180                 185                 190

Glu Arg Val Tyr Leu Lys Arg Lys Gly Phe Leu Lys Leu Cys Leu
        195                 200                 205

Lys Tyr Glu Ile Pro Val Val Pro Ala Tyr Val Phe Gly Val Ser Asp
    210                 215                 220

Tyr Tyr Phe Thr Ser Ala Lys Leu Phe Gly Leu Arg Met Trp Leu Val
225                 230                 235                 240

Gln Asn Leu Gly Ile Ala Leu Pro Leu Cys Trp Gly Arg Tyr Gly Leu
                245                 250                 255

Pro Ile Cys Pro Arg Pro Val Asp Thr Thr Leu Val Phe Asp Lys Pro
            260                 265                 270
```

```
Leu Tyr Leu Ser Cys Gln Asn Pro Ser Asn Pro Ser Glu Asp Val
            275                 280                 285

Asp Lys Ala His Leu Gln Phe Cys Gln Ala Leu Glu Lys Leu Phe Asp
290                 295                 300

Thr His Lys Glu Arg Leu Gly Tyr Gly Asp Arg Lys Leu Glu Ile Ile
305                 310                 315                 320

<210> SEQ ID NO 62
<211> LENGTH: 963
<212> TYPE: DNA
<213> ORGANISM: Phaeodactylum tricornutum

<400> SEQUENCE: 62
atgaccagat cgaagtttat aggaagtgct ggagctattg gcttattttg tttgatgatc     60
ataccgaatg tgggaattct gatcgcaaca tttctttatc ccaaagtact tgggctctac    120
tttctgattc cgtactacgc atacaacttg tccattggca acacgaagc tcgagacggc     180 aacggctgga attggttcag cgagaatttc tttgtcttta acattgtgag gggatatcta    240
aatcttaaga ttgaagctga ctccgagctc aaggaagccg aagcgaaaga aggcgcccaa    300
tttgtgttcg ccgttagccc tcacggaacg aacgcagact atcgagtttt tattgacggt    360
atgctacatg aggcactccc acagactgca agcaagatca gaacactagc ggcgacagta    420
ctgttccaca ttcccttggt tcgtgaaatc gcactttgga caggatgtgt cgatgccagc    480
cgcgcagttg ctgtcgagag attaaaagaa gaaggtggtt cactgcttgt gattcccggt    540
ggccaagcag aacaaatgta cacccaatat ggacgtgaaa gagtatatct gaaacggcgc    600
aaaggatttt tgaagctttg cttgaagtac gagattccgg tcgtcccagc ttatgttttt    660
ggcgtatctg actattactt cacgtccgca aagctctttg gtctgcgaat gtggctcgtt    720
cagaatcttg gcattgctct tccactgtgc tggggaagat atggtctacc aatctgtcct    780
agaccagtcg ataccaccct tgtctttgac aaacctttat acctatcctg ccagaatccg    840
tcgaatccct cggaagacga ggttgacaag gctcatctgc aattttgcca agccctcgag    900
aagctgtttg atacacacaa agagaggctt gggtacggcg atcgaaagct ggaataatt     960 tag                                                                  963

<210> SEQ ID NO 63
<211> LENGTH: 663
<212> TYPE: PRT
<213> ORGANISM: Rhodotorula graminis

<400> SEQUENCE: 63

Met Ser Thr Ala Asp Leu Pro Pro Gly Pro Ala Gln Leu Leu Glu Asp
1               5                   10                  15

Ala Leu Arg Gln Pro Asp Gly Pro Pro Leu Leu Ser Thr Ser Ala Ala
            20                  25                  30

Asp Pro Ser Ser Pro Leu Gln Leu Asp His Asp His Arg Pro Gly Met
        35                  40                  45

Ala Ala Asp Ala Ala Ser Ser Ala Ser Asp Ser Ser Ile Ser Thr Val
    50                  55                  60

Ser Ser Val Leu Arg Gly Gln Gln Ala Thr Thr Thr Val Thr Thr Asn
65                  70                  75                  80

Arg Gly Glu Gly Gly Arg Glu Thr Thr Glu Thr Phe Thr His Val Gly
                85                  90                  95

Ala Ala Asn Val Asp Ala Glu Tyr Ser Ser Ser Thr Gly His Ile Thr
            100                 105                 110
```

-continued

```
Leu Arg Pro Val Val Ala Lys Gly Gly Asp Pro Arg Ile Arg Leu
        115                 120                 125

Val Arg Ser Arg Arg Thr His Phe Glu Pro Arg Ile Ser His Phe Asp
130                 135                 140

Arg His Asn Lys Thr Ser Ala Glu Asp Thr Phe Arg Gly Phe Phe Ser
145                 150                 155                 160

Leu Phe Trp Ile Val Ile Ala Val Gly Thr Arg Thr Ile Tyr Asn
                165                 170                 175

Arg Val Ala Glu Thr Gly Gly Leu Leu Gly Gly Trp Gln Phe Ala Ala
                180                 185                 190

Leu Ile Ser Glu Asp Ala Trp Ala Leu Ala Leu Ser Asp Ala Val Leu
            195                 200                 205

Val Gly Ser Thr Ile Leu Cys Val Pro Phe Val Lys Leu Ile Val Asn
        210                 215                 220

Gly Trp Val Arg Tyr Tyr Thr Gly Leu Val Leu Gln His Leu Ala
225                 230                 235                 240

Gln Thr Leu Tyr Leu Gly Ile Ala Val Arg Trp Thr Phe His Arg His
                245                 250                 255

Trp Pro Trp Val Gln Ser Gly Phe Met Thr Leu His Ala Leu Ser Met
            260                 265                 270

Leu Met Lys Ile His Ser Tyr Cys Ser Leu Asn Gly Glu Leu Ser Glu
        275                 280                 285

Arg Val Arg Gln Leu Glu Lys Asp Glu Arg Lys Leu His Glu Ala Val
        290                 295                 300

Glu Glu Leu Gly Gly Gln Asp Ala Leu Glu Arg Gly Arg Val Ala
305                 310                 315                 320

Trp Glu Lys Ala Cys Ala Glu Ala Ala Glu Gln Lys Ala Ala Glu Glu
                325                 330                 335

Ala Ala Gly Gly Arg Gly Lys Ala Ser Ala Ser Ser Leu Ala Pro Pro
            340                 345                 350

Pro Ala Thr Gly Pro Gln Pro Ser Ser Asp Glu Glu Ala Val Ser Thr
        355                 360                 365

Thr Leu Arg Gln Arg Pro Ser Ala Ala Arg Arg Ser Leu Ser Pro
        370                 375                 380

Ser Ala Ala Arg Thr His Val Thr Pro Pro Ser Arg Lys Ala Glu Pro
385                 390                 395                 400

His Asp Val Glu Thr Leu Thr Trp Ser Pro Asn Glu Arg Val Ser His
                405                 410                 415

Leu Ala Ile Ala Ile Cys Glu Ala Arg Glu Ala Leu Ser Ser Ser Gly
            420                 425                 430

Ala Ala Lys Val Ser Phe Pro Asp Asn Val Thr Val Leu Asn Phe Val
            435                 440                 445

Asp Tyr Leu Leu Val Pro Thr Leu Val Tyr Glu Leu Glu Tyr Pro Arg
        450                 455                 460

Thr Asp Ser Ile Arg Pro Leu Tyr Ile Leu Glu Lys Thr Leu Ala Thr
465                 470                 475                 480

Phe Gly Thr Phe Ser Val Leu Leu Leu Ile Val Glu His Phe Ile Tyr
                485                 490                 495

Pro Val Met Pro Gly Pro Asp Ser Ser Phe Ile Ser Ser Leu Leu Asp
            500                 505                 510

Leu Ala Leu Pro Phe Thr Ile Cys Tyr Leu Leu Ile Phe Tyr Ile Ile
        515                 520                 525
```

```
Phe Glu Cys Ile Cys Asn Ala Phe Ala Glu Ile Thr Arg Phe Ser Asp
        530                 535                 540

Arg Ala Phe Tyr Ser Asp Trp Trp Asn Ser Ile Ser Phe Asp Glu Phe
545                 550                 555                 560

Ser Arg Lys Trp Asn Arg Pro Val His Thr Phe Leu Leu Arg His Val
                565                 570                 575

Tyr Ala Thr Thr Ile Ser Thr Tyr Lys Leu Ser Lys Phe Ser Ala Ala
            580                 585                 590

Phe Val Thr Phe Leu Leu Ser Ala Leu Val His Glu Leu Val Met Val
        595                 600                 605

Val Val Thr His Lys Ile Arg Met Tyr Leu Phe Met Ala Gln Leu Pro
        610                 615                 620

Leu Ile Met Leu Gly Arg Ala Ser Ile Phe Lys Arg His Pro Ala Leu
625                 630                 635                 640

Gly Asn Leu Phe Phe Trp Phe Gly Leu Leu Ser Gly Phe Pro Leu Leu
                645                 650                 655

Ala Val Ala Tyr Leu Lys Phe
            660

<210> SEQ ID NO 64
<211> LENGTH: 1992
<212> TYPE: DNA
<213> ORGANISM: Rhodotorula graminis

<400> SEQUENCE: 64
```

| | | | | |
|---|---|---|---|---|
| atgagcaccg | ccgatcttcc | accaggtcct | gcccagctgc | tcgaagacgc | cctgcgccag | 60 |
| ccagacggcc | cccctctcct | gtcgacctcc | gccgccgatc | cctcctcccc | acttcaactc | 120 |
| gaccacgacc | accgccccgg | catggctgca | gacgccgcca | gctcagcttc | agacagctct | 180 |
| atcagcacgg | tgtccagtgt | cctgcgcggt | cagcaagcca | cgacaacggt | gacgaccaac | 240 |
| aggggagaag | gcgggcgaga | aacgaccgag | accttcaccc | acgtcggcgc | cgccaatgtc | 300 |
| gacgccgagt | actcgtcctc | gaccggccac | atcacgctcc | gacccgtcgt | ggcaaagggc | 360 |
| ggtgaccctc | gccggatccg | cctcgtccgc | tcgcgccgca | cccacttcga | gccgcgcatc | 420 |
| tcgcacttcg | accgccacaa | caagacgtcg | gccgaggaca | cgttccgcgg | cttcttctcg | 480 |
| ctcttctgga | tcgtcatcgc | cgtcggcggc | acgaggacca | tctacaaccg | cgtcgccgag | 540 |
| acgggcggtc | tcctcggcgg | gtggcagttt | cgggcgctca | tctccgagga | cgcatgggct | 600 |
| ctggcgctga | gcgatgcggt | cctcgtcggg | tcgacgatac | tctgcgtccc | gttcgtcaag | 660 |
| ctcatcgtca | acggctgggt | ccggtactac | tacacgggcc | tcgtcctcca | gcacctcgcc | 720 |
| cagacgctct | acctcggcat | cgccgtccga | tggacgttcc | accgtcactg | gccctgggtc | 780 |
| cagagcggct | tcatgacgct | gcacgccctg | agcatgctca | tgaagatcca | ctcgtactgc | 840 |
| tcgctcaacg | gcgagctgtc | cgagcgcgtg | cggcagctcg | agaaggacga | gcgcaagctg | 900 |
| cacgaggcgg | tcgaggagct | tggcggccag | gacgcgctcg | agcgcgaggg | gcgcgtggcg | 960 |
| tgggagaagg | cgtgcgccga | ggcggccgag | cagaaggcgg | ccgaggaggc | ggcaggcggt | 1020 |
| cgcggcaaag | cttcggcgtc | ctcgctcgcc | ccgccgccgg | cgacagggcc | gcagccctcg | 1080 |
| tccgacgagg | aggccgtctc | gacgacgctc | cgacagcgac | cgtcggccgc | tcgccgccgc | 1140 |
| tcgctctcgc | cgtcggccgc | acggacccac | gtcacgccgc | cgtcgcgcaa | ggccgagccg | 1200 |
| cacgacgtcg | agacgctcac | ctggtcgccc | aacgagcgcg | tgtcgcacct | cgccatcgcc | 1260 |
| atctgcgagg | cacgcgaggc | cctgtcgtcg | agcggcgccg | ccaaggtctc | gttcccggac | 1320 |

```
aacgtcacgg tcctcaactt tgtcgactac cttctcgtcc cgacgctcgt gtacgagctt   1380
gagtacccga ggaccgactc tatccgaccc ttgtacatcc tcgagaagac cctcgccacg   1440
ttcggcacat tctcggtcct cctcctcatc gtcgagcact tcatctaccc ggtcatgccc   1500
gggcccgaca gctcgttcat ctcgtccctc tcgacctcg ccctcccatt caccatctgc    1560
tacctcctca tcttctacat catcttcgag tgtatctgca acgccttcgc cgagatcacg   1620
cgcttctcgg accgggcctt ctacagcgac tggtggaact cgatctcgtt cgacgagttc   1680
tcgcgcaagt ggaaccggcc cgtgcacacg ttcctcctgc gccacgtgta cgcgacgacc   1740
atctcgacct acaagctcag caagttctcg gccgcctttg tcacgttcct cctgagcgcg   1800
ctcgtgcacg agctcgtcat ggtagtcgtg acgcacaaga tccgcatgta tctctttatg   1860
gcgcagctcc ccctcatcat gctcggccga gcaagcatct tcaagcgtca ccctgcgctc   1920
ggcaacctct tcttctggtt cggcctcttg agcggtttcc ctctgctagc tgtagcgtac   1980
ctcaagttct ag                                                       1992

<210> SEQ ID NO 65
<211> LENGTH: 597
<212> TYPE: PRT
<213> ORGANISM: Pichia guilliermondii

<400> SEQUENCE: 65

Met Ser Lys Glu Asn Leu Leu Lys Ile Ser Gln Tyr Asn Thr Glu Arg
1               5                   10                  15

Arg Pro Ser Leu Ala Thr Asp Val Asp Tyr Ser Ser Thr Asp Leu Ser
                20                  25                  30

Ser Arg Leu Asp Ser Ala Asn Thr Thr Asn Gly Thr Pro Thr Val Thr
            35                  40                  45

Leu His Lys Arg Gln Ser Ser Thr Glu Leu Leu Ser Glu Ser Pro Glu
        50                  55                  60

Gln Lys Arg Phe Leu Lys Thr Ile Asp Thr Leu Asn Arg Thr Asn
65                  70                  75              80

Ser Arg Leu Arg Gln Arg Leu Asn Arg Glu Gly Asp Lys His Lys Lys
                85                  90                  95

Glu His Lys Glu His Glu Lys His Lys Asp Asp His Ser Lys Tyr Lys
                100                 105                 110

Ser Arg Phe Gly Asp Ile His Phe Tyr Ser Asn Met Thr Thr Ile Phe
            115                 120                 125

Asp Ala Asp Tyr Phe Lys Glu Ser Gln Phe Gly Val Tyr Ile Leu
        130                 135                 140

Phe Trp Leu Gly Thr Ala Phe Leu Ile Leu Asn Asn Leu Val His Thr
145                 150                 155                 160

Phe Leu Glu Asn Gly Asp Asn Leu Leu Asp Gly Pro Val Val Arg Thr
                165                 170                 175

Phe Lys Lys Asp Leu Leu Lys Ile Ala Leu Thr Asp Leu Gly Met Tyr
            180                 185                 190

Leu Thr Met Tyr Val Ser Val Phe Ile Gln Leu Gly Ile Arg Lys Gly
        195                 200                 205

Trp Tyr Ser Trp Ser Ser Thr Gly Ala Thr Leu Gln Asn Ile Tyr Ser
    210                 215                 220

Phe Val Tyr Phe Phe Ala Trp Ser Tyr Phe Ala Ser Pro Lys Tyr Met
225                 230                 235                 240

Asp Tyr Pro Trp Ile Gly Lys Val Phe Leu Ala Leu His Ser Leu Val
                245                 250                 255
```

```
Phe Leu Met Lys Met His Ser Tyr Ala Thr Tyr Asn Gly Tyr Leu Trp
        260                 265                 270

Asn Ile Phe Asn Glu Leu Gln Val Ser Arg Lys Tyr Leu Lys Ile Leu
            275                 280                 285

Asp Glu Thr Asp Glu Ser Met Ile Gly Lys Ser Val Ser Asp Leu
290                 295                 300

Arg Lys Ala Leu Val Asp Ser Ile Gly Phe Cys Ser Tyr Glu Leu Glu
305                 310                 315                 320

Tyr Gln Ser Lys Ser Thr Ser Val Asn Thr Asp Val Glu Ile Thr Gly
                325                 330                 335

Asp Lys Asn Lys Leu Asn Thr Thr Lys Ser Thr Ser Ser Leu Asp Asp
                340                 345                 350

Asp Tyr Val Ser Phe Pro Asn Asn Ile Thr Phe Phe Asp Phe Phe Arg
                355                 360                 365

Tyr Ser Met Phe Pro Thr Val Val Tyr Ser Leu Lys Phe Pro Arg Thr
            370                 375                 380

Lys Arg Ile Arg Trp Gly Tyr Val Met Glu Lys Ser Phe Ala Val Phe
385                 390                 395                 400

Gly Ile Ile Phe Leu Met Ile Thr Val Ala Gln Asn Trp Met Tyr Pro
                405                 410                 415

Ile Val Val Arg Ala Gln Glu Ala Ser Lys Leu Pro Met Ser Arg Glu
            420                 425                 430

Lys Val Leu Gln Tyr Cys Leu Val Leu Leu Asp Met Ile Pro Pro Phe
            435                 440                 445

Leu Met Glu Tyr Leu Phe Thr Phe Phe Leu Ile Trp Asp Val Ile Leu
450                 455                 460

Asn Ala Ile Ala Glu Leu Ser Arg Phe Ala Asp Arg Asp Phe Tyr Gly
465                 470                 475                 480

Pro Trp Trp Ser Cys Thr Asp Trp Ser Glu Phe Ala Arg Ile Trp Asn
                485                 490                 495

Arg Pro Val His Lys Phe Leu Leu Arg His Val Tyr Gln Ser Thr Ile
                500                 505                 510

Ser Thr Phe Lys Leu Asn Lys Asn Gln Ala Ser Leu Val Thr Phe Ile
            515                 520                 525

Ile Leu Ser Phe Val His Glu Phe Val Met Phe Val Ile Phe Arg Lys
530                 535                 540

Val Arg Phe Tyr Met Leu Ala Leu Gln Met Ser Gln Leu Pro Leu Ile
545                 550                 555                 560

Met Ile Ser Arg Thr Lys Phe Met Arg Asp Lys Lys Val Leu Gly Asn
                565                 570                 575

Val Ile Cys Trp Val Gly Phe Ile Ser Gly Pro Ser Met Ile Cys Thr
                580                 585                 590

Leu Tyr Leu Val Phe
        595

<210> SEQ ID NO 66
<211> LENGTH: 1794
<212> TYPE: DNA
<213> ORGANISM: Pichia guilliermondii

<400> SEQUENCE: 66
atgtccaagg aaaacttact taagatcagc cagtataata ctgagagaag accgtcgttg      60
gccacagacg ttgactactc ttccaccgat ttatccagtc gtctggattc ggccaacacg     120
```

| | |
|---|---|
| acaaacggaa caccgaccgt aactcttcac aagaggcaat cgtctacaga gctcttgtct | 180 |
| gagtcacctg aacagaaaag gttcttgaaa acgatagaca ctttgaatcg aaccacaaat | 240 |
| tctagattac gccagaggtt aaaccgtgag ggcgataagc ataaaaagga acacaaagaa | 300 |
| catgaaaaac ataagatga ccattctaaa tacaagtctc ggtttggaga tatccatttc | 360 |
| tactcaaaca tgacaaccat cttcgatgct gattacttta aggaatcgca gttctttgga | 420 |
| gtttacattc tcttttggct cggaacggca ttcttaattc tcaacaactt ggtccataca | 480 |
| tttttggaga acgagacaa tcttctcgat ggaccagttg tcagaacgtt taaaaaggac | 540 |
| ttacttaaaa ttgctcttac agacttggga atgtacttga cgatgtacgt ctctgtcttt | 600 |
| attcaattgg gcatccgcaa aggatggtat agctggagct caacaggagc caccttgcaa | 660 |
| aacatatact cattcgtgta cttctttgcc tggagttact ttgcgtcgcc aaagtacatg | 720 |
| gactaccctt ggattggaaa ggtgtttctt gcacttcaca gcttggtgtt tctcatgaaa | 780 |
| atgcattctt atgccacata caacggctat cttgggaaca tcttcaacga gcttcaagtg | 840 |
| tcacgaaagt acttgaagat attggacgag accgatgaat ccatgattga gggtaagagt | 900 |
| gtttccgatt tgcgaaaggc tttggtagac agcattggtt tctgctcata cgagttggag | 960 |
| taccagtcca atcaacgag cgtgaacacg gatgtcgaaa tcaccggcga caagaacaaa | 1020 |
| ttgaacacaa ccaagtctac cagttcactc gatgacgact atgtgagttt ccccaataac | 1080 |
| attacgtttt tcgattttttt caggtattca atgtttccaa cagtggtgta ttctctcaag | 1140 |
| ttcccacgta caaagcgtat tagatggggt tacgtcatgg aaaagtcatt tgcagtgttt | 1200 |
| ggcatcatct tcttgatgat caccgtcgct caaaactgga tgtatcctat cgttgtacga | 1260 |
| gcacaagagg ctagcaaact cccaatgtca agagaaaagg tattgcagta ctgtttggtt | 1320 |
| ttactagaca tgattccacc atttctcatg gaatatcttt tcaccttttt cttgatttgg | 1380 |
| gacgtgatcc taaatgcgat agccgaattg agtaggtttg cagatcggga cttttatggt | 1440 |
| ccttggtggt cttgtaccga ttggtcggaa tttgcaagaa tttggaatcg tcctgttcac | 1500 |
| aaatttttgc ttcgtcatgt gtaccagtca actatcagta ctttcaaact caataaaaac | 1560 |
| caagcgtcgt tggtgacgtt tatcattctg agttttgttc atgagtttgt catgtttgtc | 1620 |
| attttttagaa aggtgagatt ctacatgttg gcgctccaga tgtctcagct tccattgata | 1680 |
| atgattagtc gaacaaaatt catgagagac aaaaaagtgt tgggaaatgt tatctgctgg | 1740 |
| gtaggattca tttctggacc atcgatgatc tgtactttgt atttagtatt ttaa | 1794 |

<210> SEQ ID NO 67
<211> LENGTH: 515
<212> TYPE: PRT
<213> ORGANISM: Arxula adeninivorans

<400> SEQUENCE: 67

Met Ala Thr Ala Thr Ala Ile Ala Thr Val Thr Glu Gly Leu Gly Leu
1               5                   10                  15

Asp Lys Val Leu Ser Lys Glu Gln Pro Gly Leu Ser Lys Leu Ala Pro
            20                  25                  30

Arg Ala Asn Thr Asn Val Gln Pro Thr Gln Leu Gln Ser Pro Ser Pro
        35                  40                  45

Pro Gln Ser Arg Ser Ser Ser Pro Ile Ser Ala Ser Ser Ser Ser Glu
    50                  55                  60

Ser Leu Glu Leu Lys Val Pro Lys Ala Lys Ser Pro Ser Ser Ser Lys
65                  70                  75                  80

```
His Lys Pro His Tyr Arg Pro Val His Val Arg Ser Thr Ala Ser Ile
                85                  90                  95

Leu Ser Arg Asp Pro Ala Ala Arg Thr Glu Pro Pro Ser Tyr Ser Gly
            100                 105                 110

Phe Arg Asn Leu Ala Met Ile Ala Leu Ala Val Ser Asn Met Arg Leu
            115                 120                 125

Leu Leu Glu Asp Tyr Gln Asn Tyr Gly Val Phe His Thr Leu Asn Ile
            130                 135                 140

Met Gly Leu Ser Ala His Asp Val Arg Leu Thr Leu Ala Leu Thr Ala
145                 150                 155                 160

Ser Val Pro Phe His Leu Phe Val Ala Leu Ala Ile Glu Arg Ile Ala
                165                 170                 175

Val Leu Thr Met Pro Ser Lys Ser Thr Ala His Asn His Arg Ser Lys
            180                 185                 190

His Leu Trp Gly Leu Phe Ala Val Leu His Ala Leu Asn Ala Ala Ala
            195                 200                 205

Val Leu Ala Ile Ser Ser Tyr Thr Val Tyr Ser Arg Met Trp Ser Pro
210                 215                 220

Ala Val Gly Thr Leu Cys Glu Cys His Ala Ile Val Val Cys Phe Lys
225                 230                 235                 240

Val Ala Ser Tyr Ala Leu Thr Asn Arg Asp Leu Arg Asp Ala Ala Ile
                245                 250                 255

Asp Gly Leu Glu Thr Thr Asp Pro Leu Ser Lys Leu Pro Tyr Pro
            260                 265                 270

Ser Asn Leu Thr Leu Ser Asn Leu Val Tyr Phe Trp Trp Ala Pro Thr
            275                 280                 285

Leu Val Tyr Gln Pro Ile Tyr Pro Arg Trp Pro Leu His Arg Arg Trp
            290                 295                 300

Gly Phe Ile Phe Ser Arg Leu Leu Glu Ile Met Gly Ser Met Val Leu
305                 310                 315                 320

Ile Trp Phe Ile Ser Thr Gln Tyr Ala Asn Pro Ile Leu Glu Ser Ser
                325                 330                 335

Leu Gly His Phe Glu Gln Phe Asn Val Val Lys Ile Ser Glu Cys Leu
            340                 345                 350

Leu Lys Leu Ala Ser Val Ser Met Ala Ile Trp Leu Leu Gly Phe Phe
            355                 360                 365

Cys Leu Phe Gln Ser Phe Leu Asn Leu Leu Ala Glu Leu Val Arg Phe
370                 375                 380

Gly Asp Arg Glu Phe Tyr Gln Asp Trp Trp Asn Ala Gly Ser Val Gly
385                 390                 395                 400

Thr Tyr Trp Arg Lys Trp Asn Arg Pro Val His Asn Tyr Phe Leu Arg
                405                 410                 415

His Phe Tyr Ile Pro Met Leu Lys Arg Gly Tyr Ser Gln Arg Thr Ala
            420                 425                 430

Ser Val Ile Val Phe Phe Leu Ser Ala Ile Leu His Glu Val Ala Val
            435                 440                 445

Gly Val Pro Thr Gln Ser Leu Ile Gly Val Ala Phe Val Gly Met Gly
450                 455                 460

Ala Gln Ile Pro Leu Val Leu Ala Thr Ser Pro Leu Glu Lys Met Gly
465                 470                 475                 480

Glu Thr Gly Ala Thr Ile Gly Asn Cys Ile Phe Trp Leu Ser Phe Phe
                485                 490                 495

Leu Gly Gln Pro Met Gly Val Leu Leu Tyr Tyr Phe Ala Trp Asn Met
```

Lys His Gln
     515

<210> SEQ ID NO 68
<211> LENGTH: 1548
<212> TYPE: DNA
<213> ORGANISM: Arxula adeninivorans

<400> SEQUENCE: 68

| | |
|---|---|
| atggccaccg ctactgctat cgctacggtc acggagggcc tgggactaga taaggtgcta | 60 |
| tccaaggagc agccaggctt gtcgaagcta gctcctcgag cgaatacaaa tgtacaaccg | 120 |
| acccagttgc agtccccgtc tccaccacaa tctcgatctt cgtctccaat tcggcctcc | 180 |
| tcatcatcag agtccctgga gctcaaggtg cccaaggcca atcgccatc atcttccaaa | 240 |
| cacaaaccac actaccgccc cgtgcatgtg cggtcaacag catccatcct gtccagagac | 300 |
| ccggccgcca gaaccgagcc tccctcttac tctgggttca ggaacctagc catgattgca | 360 |
| ttggcggttt ctaatatgcg cctccttctc gaggactatc aaaactatgg cgtgttccac | 420 |
| actctcaaca ttatgggctt gagcgcacac gacgttcgcc tcacactggc attgacagct | 480 |
| tcggttccgt ccatctgtt tgtggccctg ccattgagc gcatcgcagt cctcactatg | 540 |
| ccctccaaat ctacagcaca caaccaccgc tcaaagcatc tctggggctt gtttgcagtt | 600 |
| ctgcatgctc tcaacgccgc tgctgtgcta gcaatcagct catacaccgt atacagtcgc | 660 |
| atgtggagtc ctgctgtggg aacattgtgc gaatgccacg caatcgtggt atgctttaag | 720 |
| gtggcatcgt atgcgcttac caaccgagac ttacgagatg ctgccattga tgggctagag | 780 |
| acaactgacc ctctgttgtc caagttgccc tacccatcca accttacctt gtcaaatctc | 840 |
| gtgtatttct ggtgggcccc aaccctagtg tatcagccaa tttaccctcg atggcccctg | 900 |
| catcgacgat ggggcttcat ctttctcgc ctgctcgaga ttatgggatc tatggtacta | 960 |
| atctggttca tttccaccca atacgccaac cccatttggg aatcatcctt ggggcacttt | 1020 |
| gaacagttta cgtggttaa atctcagaa tgtctcctca aattagcatc ggtctccatg | 1080 |
| gccatctggc ttttgggttt cttttgtctc tttcaatcgt ttttgaactt gctggcagaa | 1140 |
| ttggttcgtt ttggcgaccg cgagttctac caagactggt ggaacgccgg ctcagtaggt | 1200 |
| acctactggc gcaaatggaa ccgaccagtg cacaactatt tcttgcgcca tttctacatc | 1260 |
| ccaatgctca agcgaggtta ttcacagcgc actgcctcgg tcattgtatt ctttttatct | 1320 |
| gccattctcc atgaagttgc tgttggcgtg cctactcagt ccttgattgg agttgcgttt | 1380 |
| gtaggcatgg gtgcccagat tcctctagtg ctggccacta gtcctttgga aaagatgggc | 1440 |
| gaaactggcg caactattgg caactgcatc ttttggctct ctttcttcct gggccagcca | 1500 |
| atgggggtac tgctttacta ctttgcgtgg aatatgaagc accagtag | 1548 |

<210> SEQ ID NO 69
<211> LENGTH: 564
<212> TYPE: PRT
<213> ORGANISM: Phaeodactylum tricornutum

<400> SEQUENCE: 69

Met Asp Glu Thr Glu Ile Thr Pro Leu Leu Arg Phe Ser Thr Pro Ser
1               5                   10                  15

Arg Ala Glu His Ser Ser Trp Ile Lys Leu Ala Ser Glu Ser Cys Ala
            20                  25                  30

```
Tyr Ser Glu Thr Asp Glu Phe Leu Ala Asp Glu Ala Ala Arg Ala Thr
            35                  40                  45

Gln Arg Ala Leu Gln His Gln Glu Ala Leu Gln Met Ala Gln Ala Met
 50                  55                  60

Pro Gly Ala Lys Pro Gly Thr Leu Pro Pro Leu Tyr Phe Ala Pro Thr
 65                  70                  75                  80

Ile Lys Arg Ser Arg Ser Phe Ala Lys Leu Gln Glu His His Gly Asp
                 85                  90                  95

Gly Met Pro Arg Val Asn Met Arg Arg Thr Lys Ser Arg Asp Phe Asn
            100                 105                 110

Ala Asp Lys Leu Asp Ala Arg Ser Thr Lys Gly Tyr Pro Pro Ser Lys
            115                 120                 125

Pro Met His Arg Ala Ala Glu Pro Ser Tyr Leu Ser Ala Asp Ala Pro
    130                 135                 140

Ile Gln Asn Tyr Arg Gly Phe Leu Asn Leu Gly Val Ile Ile Leu Ile
145                 150                 155                 160

Val Ser Asn Phe Arg Leu Ile Leu Gly Thr Ile Arg Ser Asn Gly Phe
                165                 170                 175

Val Leu Thr Thr Ala Val Lys His Tyr Lys Asn Leu Asn His Leu Lys
            180                 185                 190

Glu Asp Pro Trp Gln Glu Phe Pro Phe Val Ser Gly Phe Leu Leu Gln
            195                 200                 205

Leu Val Phe Val Ser Ile Ala Phe Gly Ile Glu Trp Met Leu Cys Arg
    210                 215                 220

Lys Tyr Phe Asn Glu Asn Phe Gly Met Ile Leu His His Phe Asn Ala
225                 230                 235                 240

His Ser Ala Leu Leu Ile Pro Leu Gly Ile Val Trp Asn Leu Ile Asp
                245                 250                 255

Arg Pro Ala Val Gly Ala Ile Leu Leu Leu His Ala Thr Ile Thr Trp
            260                 265                 270

Met Lys Leu Ile Ser Tyr Met Leu Ala Asn Glu Asp Tyr Arg Leu Ser
            275                 280                 285

Ser Arg Arg Val Gly Gly Asn Pro His Leu Ala Thr Leu Ala Leu Val
    290                 295                 300

Glu Asn Leu Asp Ser Asp Glu Ala Asn Ile Asn Tyr Pro Gln Asn Val
305                 310                 315                 320

Thr Leu Arg Asn Ile Phe Tyr Phe Trp Cys Ala Pro Thr Leu Thr Tyr
                325                 330                 335

Gln Ile Ala Phe Pro Lys Ser Pro Arg Val Arg Tyr Trp Lys Ile Ala
            340                 345                 350

Asp Ile Leu Met Arg Met Thr Val Ser Ile Ala Leu Phe Thr Phe Leu
            355                 360                 365

Leu Ala Gln Ile Val Gln Pro Ala Leu Glu Glu Leu Val Ser Asp Leu
    370                 375                 380

Asp Glu Thr Asn Gly Ser Tyr Thr Ala Ala Ile Phe Ala Glu Tyr Trp
385                 390                 395                 400

Leu Lys Leu Ser Ile Ala Asn Thr Tyr Leu Trp Leu Leu Met Phe Tyr
                405                 410                 415

Thr Tyr Phe His Leu Tyr Leu Asn Leu Phe Ala Glu Leu Leu Arg Phe
            420                 425                 430

Gly Asp Arg Val Phe Tyr Lys Asp Trp Trp Asn Ser Ser Glu Val Ser
    435                 440                 445

Ala Tyr Trp Arg Leu Trp Asn Met Pro Val His Tyr Trp Leu Ile Arg
```

His Val Tyr Phe Pro Cys Val Arg Leu Lys Met Pro Lys Val Ala Ala
465                 470                 475                 480

Thr Phe Val Val Phe Phe Leu Ser Ala Val Met His Glu Val Leu Val
            485                 490                 495

Ser Val Pro Phe His Ile Ile Arg Pro Trp Ser Phe Ile Gly Met Met
        500                 505                 510

Met Gln Ile Pro Leu Val Ala Phe Thr Lys Tyr Leu Tyr Arg Lys Phe
    515                 520                 525

Pro Gly Gly Ser Ile Gly Asn Val Leu Phe Trp Met Thr Phe Cys Val
530                 535                 540

Ile Gly Gln Pro Met Ala Ile Leu Leu Tyr Tyr His Asp Ile Met Asn
545                 550                 555                 560

Arg Lys Gly Asn

<210> SEQ ID NO 70
<211> LENGTH: 1695
<212> TYPE: DNA
<213> ORGANISM: Phaeodactylum tricornutum

<400> SEQUENCE: 70

```
atggatgaga ccgaaattac acctttgttg cgttttttcga caccttcccg agccgaacac      60
tcgtcctgga taaagcttgc ctcggaatcc tgtgcttaca gcgaaacgga cgagtttctc     120
gctgacgagg ccgctcgcgc aacccagcgt gctttgcaac atcaagaagc gctgcaaatg     180
gcccaagcca tgcctggggc aaagccagga acgctgccgc cactctactt cgcgcctacc     240
ataaagcgtt cgcgttcctt tgctaagcta caagaacatc atggagatgg gatgcctcgg     300
gtaaatatgc gtcggaccaa atcgcgagat tttaacgcgg ataagttgga tgcgcgaagt     360
accaagggct atccccttc caagccgatg catcgtgcgg cagagccctc ataccctcagc     420
gcggatgctc ccattcaaaa ctaccgagga tttctgaatt taggcgttat tattttgatt     480
gtttctaact ttcggctgat cttgggcaca atccgtagca acggatttgt cttgacgact     540
gcagtgaagc actacaagaa cctaaatcac ctcaaggaag atccctggca ggaatttcct     600
tttgtatcag gatttcttct ccagctcgtc tttgtttcga ttgcgtttgg gatcgaatgg     660
atgttgtgcc ggaaatactt caacgaaaac ttcggcatga tccttcatca cttcaatgcc     720
cactcagcct tgctgatacc tttaggtatt gtttggaatc tcatcgatag acctgcggtt     780
ggtgcaattt tgcttttaca cgctacgata acatggatga aactcatttc ttacatgttg     840
gcgaacgaag attaccggct atcatcgcgt cgcgttgggg gcaacccaca cctagctacg     900
ctcgcattag tcgaaaatct agattcgat gaggcgaaca ttaactaccc ccaaaatgtt     960
actctccgca acattttta tttttggtgt gctccgacgt tgacttacca gattgccttc    1020
ccgaagtccc cgcgagttcg ctattggaaa atcgcggata tcctgatgcg catgacggtg    1080
tccatcgcac tattcacctt tttgctggca caaattgttc agcctgcatt ggaagagcta    1140
gtgagcgacc tggacgagac caatggatcc tacaccgcag caatatttgc cgagtactgg    1200
ctgaaacttt cgattgctaa cacatatttta tggcttctta tgttctatac atatttccat    1260
ttgtatctga acctctttgc tgagcttctg cgatttggag atcgtgtgtt ctacaaagat    1320
tggtggaatt cgtcggaagt atctgcatat tggaggcttt ggaatatgcc tgttcactat    1380
tggttgatcc gacatgtgta tttccccctgc gtgcgactga agatgccgaa ggtcgctgca    1440
acctttgtcg tttttttcct ctccgccgtt atgcacgagg tgcttgtcag cgtacccttt    1500
```

```
catattattc gtccgtggtc ttttatcggg atgatgatgc agattccttt ggttgcgttc   1560
acaaagtatc tctatcgcaa attcccgggc ggctcgattg gtaatgtcct gttctggatg   1620
acattttgcg tcattggcca gccaatggcg attctcttgt actatcatga tattatgaat   1680
cgaaaaggaa attga                                                    1695
```

```

<210> SEQ ID NO 71
<211> LENGTH: 503
<212> TYPE: PRT
<213> ORGANISM: Metarhizium acridum

<400> SEQUENCE: 71

Met Ser Thr Ala Thr Thr Thr Ser Val Ser Pro Ala Asn Gly Thr Val
1               5                   10                  15

Ser Lys Arg Asn Ala Thr Lys Arg Arg Asn Gly Asn Ala Ser Pro Gly
            20                  25                  30

Pro Val Glu Glu Glu Ser Glu Asp Ala Ala Ala Ala Glu Lys Pro Arg
        35                  40                  45

Ala Ser Val Ala Gln Lys Asn Tyr Arg His Val Ala Ala Val His Ser
    50                  55                  60

Lys Ser Arg Pro Ser Cys Leu Ser His Asp Ser Asp Ala Thr Pro Ser
65                  70                  75                  80

Phe Ile Gly Phe Arg Asn Leu Met Val Ile Val Leu Asp Val Leu Ile
                85                  90                  95

Gly Gly Leu Leu Tyr Phe Leu Ile Pro Cys His Leu Leu Val Ala Tyr
            100                 105                 110

Leu Ile Glu Leu Ala Ala Ala Lys Gln Ala Arg Gly Ser Arg Lys Arg
        115                 120                 125

Leu Lys Pro Gly Ser Thr Val Pro Ser Glu Gln Asp Asn Ser Lys Phe
    130                 135                 140

His Ser Thr Trp Val Leu Val Ala Trp Ala His Gly Ile Asn Met Thr
145                 150                 155                 160

Leu Ala Leu Ala Leu Thr Thr Phe Met Val Tyr Phe Tyr Ile His His
                165                 170                 175

Pro Leu Val Gly Thr Leu Thr Glu Met His Ala Val Ile Val Ser Leu
            180                 185                 190

Lys Thr Ala Ser Tyr Ala Phe Thr Asn Arg Asp Leu Arg His Ala Tyr
        195                 200                 205

Leu His Pro Val Lys Gly Glu Phe Ile Pro Glu Leu Tyr Ser Lys Cys
    210                 215                 220

Pro Tyr Pro Asn Asn Ile Thr Phe Gly Asn Leu Ala Tyr Phe Trp Trp
225                 230                 235                 240

Ala Pro Thr Leu Val Tyr Gln Pro Val Tyr Pro Arg Thr Asp Lys Ile
                245                 250                 255

Arg Trp Val Phe Val Phe Lys Arg Leu Gly Glu Val Cys Cys Leu Ser
            260                 265                 270

Ala Phe Ile Trp Phe Ala Ser Phe Gln Tyr Ala Ala Pro Val Leu Gln
        275                 280                 285

Asn Ser Leu Asp Lys Ile Ala Ser Leu Asp Leu Leu Met Ile Leu Glu
    290                 295                 300

Arg Leu Leu Lys Leu Ser Thr Ile Ser Leu Val Ile Trp Leu Ala Gly
305                 310                 315                 320

Phe Phe Ala Leu Phe Gln Ser Phe Leu Asn Ala Leu Ala Glu Val Leu
                325                 330                 335
```

```
Arg Phe Gly Asp Arg Ser Phe Tyr Asp Asp Trp Trp Asn Ser Glu Ser
            340                 345                 350

Leu Gly Ala Tyr Trp Arg Thr Trp Asn Arg Pro Val Tyr Thr Tyr Phe
        355                 360                 365

Lys Arg His Val Tyr Val Pro Met Ile Gly Arg Gly Trp Ser Pro Trp
    370                 375                 380

Ala Ala Ser Cys Ala Val Phe Phe Val Ser Ala Val Leu His Glu Val
385                 390                 395                 400

Leu Val Gly Val Pro Thr His Asn Ile Ile Gly Thr Leu Ser Ser Val
                405                 410                 415

Leu Ser Ile Val Leu Thr Leu Val Pro Asn Leu Tyr Ser Gly Val Ala
            420                 425                 430

Phe Leu Gly Met Phe Leu Gln Leu Pro Leu Ile Ala Ile Thr Ala Pro
        435                 440                 445

Leu Glu Lys Met Lys Trp Gly His Thr Gly Arg Val Met Gly Asn Val
    450                 455                 460

Ile Phe Trp Val Ser Phe Thr Ile Phe Gly Gln Pro Phe Ala Ala Leu
465                 470                 475                 480

Met Tyr Phe Tyr Ala Trp Gln Ala Lys Tyr Gly Ser Val Ser Lys Glu
                485                 490                 495

Pro Ile Leu Ala Leu Gln Thr
            500

<210> SEQ ID NO 72
<211> LENGTH: 1512
<212> TYPE: DNA
<213> ORGANISM: Metarhizium acridum

<400> SEQUENCE: 72
atgagcacgg ccaccaccac cagtgtcagc ccagcgaatg gcaccgtgag caagagaaat     60
gccaccaagc gtcgcaacgg caatgcatct cccggcccgg tggaagaaga atccgaagac    120
gcagccgcag ccgagaagcc cagagcctct gtcgcccaga agaactatcg ccacgtagca    180
gcagtgcatt ccaagagccg cccgtcgtgc ctaagccacg actccgatgc cacgccaagc    240
tttatcgggt ttcgaaatct catggtcatt gttttggatg tcctcatcgg cggacttctc    300
tactttctca ttccctgcca tctgttggtt gcctacttga tcgaattggc cgccgcaaaa    360
caggctcgag gatcccgaaa gcgcctcaaa ccaggctcta ctgtaccgtc ggaacaagac    420
aattccaagt tccattcaac atgggttctg gtggcctggg ctcatggtat caatatgacg    480
cttgctttag ccctcacaac ctttatggtt tacttttaca tccaccaccc gctcgttggg    540
accctgaccg agatgcatgc cgtcattgtg tcgttgaaga cagcctcgta cgcattcacc    600
aaccgagatc ttcgccacgc ttacctgcac cccgttaaag gagagtttat tcctgaactc    660
tactcgaaat gcccgtaccc gaataacatc acctttggca acctcgccta cttctggtgg    720
gcgccgacgc tggtctatca gcccgtatac ccgcgcaccg acaagatcag atgggtcttt    780
gtttttaaga ggctgggcga agtatgctgt ttgagcgcat tcatctggtt cgccagcttc    840
caatacgccg cgccggttct gcagaattcg ctcgacaaga ttgcttcgtt ggacttactc    900
atgatcctag agcggctgct gaagctgtca accatttctc tggttatttg gctggcagga    960
ttctttgccc tattccagtc cttcttaaac gcacttgccg aagtgctgcg gttcggcgac   1020
cgatcatttt acgacgactg gtggaacagc gagagtctcg gagcctactg gagaacgtgg   1080
aacaggcccg tatatacgta ctttaagcgc catgtgtatg tacccatgat tgggcgtgga   1140
```

```
tggagcccat gggctgcaag ttgcgccgtc ttttttgtgt ctgccgtgtt acacgaggtt    1200
cttgttggtg ttcccaccca caacattatc ggtacgctat cctccgtctt atccatcgtc    1260
ttgaccctcg ttcctaacct atattcaggc gttgcttttc taggcatgtt cttgcagctt    1320
cctctcatcg ccatcacggc ccctctagag aaaatgaaat gggggcatac cggcagagta    1380
atgggaaacg taatcttttg ggtgtccttt accatcttcg gtcagccatt tgcggcattg    1440
atgtactttt acgcatggca ggccaagtac ggtagcgtca gtaaagaacc gattcttgcg    1500
ttgcagacat ga                                                         1512
```

<210> SEQ ID NO 73
<211> LENGTH: 516
<212> TYPE: PRT
<213> ORGANISM: Ophiocordyceps sinensis

<400> SEQUENCE: 73

Met Ala Ala Thr Gly Thr Ser Val Glu Pro Ser Thr Gly Thr Ala Thr
1               5                   10                  15

Gln Arg His Ser Gly Lys Asp Gln Thr Gly Val Glu Pro Arg Thr Gly
            20                  25                  30

Thr Val Lys Thr Ser Gln Lys Lys Tyr Arg His Val Val Val His
        35                  40                  45

Ser Gln Val Arg Pro Ser Cys Leu Ser His Asp Ser Asp Ala Ala Pro
    50                  55                  60

Ser Phe Ile Gly Phe Arg Asn Leu Met Val Ile Val Leu Val Val Gly
65                  70                  75                  80

Asn Leu Arg Leu Met Ile Glu Asn Ile Gln Lys Ala Arg Ser Tyr Leu
                85                  90                  95

Ser Phe Ile Pro Gly Gln Cys Ala Pro Gly Tyr Gly Val Leu Ile Cys
            100                 105                 110

Ile Arg Cys His Ala Tyr Ser Arg Gln Asp Ile Leu Val Gly Gly Leu
        115                 120                 125

Leu Tyr Ile Leu Ile Pro Cys His Leu Leu Ala Ala Tyr Leu Ile Glu
    130                 135                 140

Leu Ala Ala Ala Gln Gln Ala Leu Gly Ser Arg Lys Arg Leu Lys Asp
145                 150                 155                 160

Gly Ala Ala Ser Pro Glu Glu Asp Arg Asn Ser Asn Lys Phe His
                165                 170                 175

Ala Thr Trp Leu Ile Val Ala Trp Val His Ala Val Asn Ile Thr Leu
            180                 185                 190

Ala Leu Val Val Thr Ser Ala Val Val Tyr Phe Tyr Ile His His Pro
        195                 200                 205

Leu Ile Gly Thr Leu Thr Glu Met His Ala Ile Ile Val Trp Leu Lys
    210                 215                 220

Thr Ala Ser Tyr Ala Phe Thr Asn Arg Asp Leu Arg His Ala Tyr Leu
225                 230                 235                 240

His Pro Val Glu Gly Glu Leu Val Pro Asp Met Tyr Ala Lys Cys Pro
                245                 250                 255

Tyr Pro Gln Asn Ile Thr Phe Gly Asn Leu Val Tyr Phe Trp Trp Ala
            260                 265                 270

Pro Thr Leu Val Tyr Gln Pro Val Tyr Pro Arg Thr Asp Lys Ile Arg
        275                 280                 285

Trp Leu Phe Val Ala Lys Arg Leu Gly Glu Val Phe Cys Leu Ser Ala
    290                 295                 300

```
Phe Ile Trp Phe Ala Ser Phe Gln Tyr Ala Ala Pro Val Leu Arg Asn
305                 310                 315                 320

Ser Leu Asp Lys Ile Ala Ser Leu Asp Phe Ala Ser Ile Phe Glu Arg
            325                 330                 335

Leu Val Lys Leu Ser Thr Ile Ser Leu Val Ile Trp Leu Ala Gly Phe
        340                 345                 350

Phe Ala Leu Phe Gln Ser Phe Leu Asn Ala Leu Ala Glu Val Leu Arg
    355                 360                 365

Phe Gly Asp Arg Ala Phe Tyr Asp Asp Trp Trp Asn Ser Glu Ser Leu
370                 375                 380

Gly Ala Tyr Trp Arg Thr Trp Asn Lys Pro Val Tyr Thr Tyr Phe Lys
385                 390                 395                 400

Arg His Val Tyr Met Pro Met Ile Gly Arg Gly Trp Ser Pro Arg Val
                405                 410                 415

Ala Ser Leu Val Val Phe Phe Ile Ser Ala Val Leu His Glu Ile Leu
            420                 425                 430

Val Gly Leu Pro Thr His Asn Val Ile Gly Val Ala Phe Leu Gly Met
        435                 440                 445

Phe Leu Gln Leu Pro Leu Ile Ala Ile Thr Ala Pro Met Glu Lys Met
    450                 455                 460

Arg Leu Gly Lys Gly Gly Lys Leu Val Gly Asn Val Ile Phe Trp Val
465                 470                 475                 480

Ser Phe Thr Ile Phe Gly Gln Pro Phe Ala Thr Leu Met Tyr Phe Tyr
                485                 490                 495

Ala Trp Gln Ala Lys Tyr Gly Ser Val Ser Arg Glu Met Gln Gln Ala
            500                 505                 510

Ala Ser Ile Lys
        515

<210> SEQ ID NO 74
<211> LENGTH: 1551
<212> TYPE: DNA
<213> ORGANISM: Ophiocordyceps sinensis

<400> SEQUENCE: 74
atggcggcta cggggaccag cgtcgagccc tcgactggta ccgcgacaca acgccactcc    60
ggcaaggatc agactggggt cgagccacgc accggcacgg tcaagacatc ccagaaaaag   120
tatcgccatg tcgttgtcgt ccactcccag gtccggccct cgtgcctcag ccacgattca   180
gatgccgccc ccagcttcat tggcttccgc aatctcatgg ttattgtcct ggtcgtcggc   240
aacttgcgat tgatgattga aacatccaa aaggctcgtt catacctgtc gttcataccT   300
ggccaatgcg cccccggcta cggagtcttg atctgcatcc gctgccacgc ctacagccgc   360
caagacattc tcgtcggcgg gctgctgtac atcctcattc cctgccatct cctggccgcc   420
tatctcatcg agctcgccgc cgcccagcag gcactgggt cgagaaagcg cctcaaggat   480
ggcgccgcca gcccggagga ggaggaccgc aacagcaaca agttcacgc gacatggctc   540 atcgtcgcct gggtccatgc cgtcaacatc accctggccc tggtcgtgac ctcggccgtc   600
gtctactttt acatccacca cccactcatc ggcaccctca ccgaaatgca cgccatcatc   660
gtctggctca agacggcctc gtacgccttt actaaccgcg acctgcgcca cgcgtacctg   720
caccccgtcg agggcgagct cgtcccggac atgtacgcca agtgcccgta tccgcaaaac   780
atcacctttg caacctcgt ctacttctgg tgggcccccga cgctcgtcta ccagcccgtc   840
```

```
tatccccgga ccgacaagat caggtggctc tttgtcgcca agcggctggg agaggtcttt    900
tgcttgagcg ccttcatctg gttcgccagc ttccagtatg ccgcgcccgt cctgcgcaac    960
tctctcgaca aaattgcttc gctcgacttt gcctccatct ttgagcggct ggtgaagctg   1020
tccaccatct ccctcgtcat ctggctcgcc ggcttcttcg ccctcttcca gtcctttctc   1080
aacgccctcg ccgaggtgct tcggttcggc gaccgggctt ctacgatga ctggtggaac    1140
agcgagagcc taggcgccta ctggcggacc tggaacaagc ccgtctacac ctacttcaag   1200
cgccacgtgt acatgcccat gatcgggcgt ggctggagtc ccagggtggc cagtctggtc   1260
gtcttcttca tctcagccgt cctccacgag atccttgtcg gctaccac tcacaacgtc    1320
atcggcgtcg cctttctcgg catgtttctc cagctgcctc tcatcgccat cacggcgccc   1380
atggagaaga tgaggctcgg caaaggcggc aagctcgtag caacgtcat cttctgggtg    1440
tcgtttacca tctttggcca gcccttttgcg acattgatgt acttttatgc cttggcaggcc  1500
aaatacggga gcgtgagcag ggagatgcag caagcggcaa gcatcaagta a            1551
```

<210> SEQ ID NO 75
<211> LENGTH: 510
<212> TYPE: PRT
<213> ORGANISM: Trichoderma virens

<400> SEQUENCE: 75

Met Ala Pro Pro Ala Glu Ser Ser Thr Thr Thr Ser Val Glu Ala Ser
1               5                   10                  15

Thr Gly Ser Val Ser Arg Arg His Ala Ser Gln Ser Glu Ala Asp Leu
            20                  25                  30

Thr Ser Val Glu Pro Val Asn Gly Thr Thr Lys Asn Arg Leu Ser Lys
        35                  40                  45

Thr Pro Pro Lys Lys Tyr Arg His Val Ala Ala Val His Ser Gln Thr
    50                  55                  60

Arg Pro Ser Cys Leu Ser His Asp Ser Pro Ala Ala Pro Ser Phe Leu
65                  70                  75                  80

Gly Phe Arg Asn Leu Met Val Ile Val Leu Val Val Gly Asn Leu Arg
                85                  90                  95

Leu Met Ile Glu Asn Ile Gln Lys Tyr Gly Val Leu Ile Cys Ile Arg
            100                 105                 110

Cys His Asp Tyr Arg Arg Gln Asp Val Leu Leu Gly Leu Leu Leu Tyr
        115                 120                 125

Phe Leu Ile Pro Cys His Leu Phe Ala Ala Tyr Leu Ile Glu Leu Val
    130                 135                 140

Ala Ala Lys Gln Ala Glu Gly Ser Arg Lys Arg Ile Lys Asp Asn Asn
145                 150                 155                 160

Ser Gly Pro Ser Glu Ala Glu Arg Lys Lys Phe His Ser Ile Trp Val
                165                 170                 175

Leu Ala Ala Leu Ala His Gly Ile Asn Ile Thr Leu Ala Leu Ala Ile
            180                 185                 190

Thr Thr Val Val Val Tyr Phe Tyr Val Tyr His Pro Leu Ile Gly Thr
        195                 200                 205

Leu Thr Glu Met His Ala Ile Ile Val Trp Leu Lys Thr Ala Ser Tyr
    210                 215                 220

Ala Phe Thr Asn Arg Asp Leu Arg His Ala Tyr Leu His Pro Val Glu
225                 230                 235                 240

Gly Glu Glu Val Pro Asp Leu Tyr Lys Ser Cys Pro Tyr Pro Gln Asn
                245                 250                 255

Val Thr Met Lys Asn Leu Val Tyr Phe Trp Trp Ala Pro Thr Leu Val
            260                 265                 270

Tyr Gln Pro Val Tyr Pro Arg Thr Asp Lys Ile Arg Trp Val Phe Val
        275                 280                 285

Phe Lys Arg Leu Gly Glu Ile Phe Cys Leu Ala Val Phe Ile Trp Val
    290                 295                 300

Ala Ser Ala Gln Tyr Ala Thr Pro Val Leu Arg Asn Ser Leu Asp Lys
305                 310                 315                 320

Ile Ala Ser Leu Asp Leu Pro Asn Ile Leu Glu Arg Leu Met Lys Leu
                325                 330                 335

Ser Thr Ile Ser Leu Val Ile Trp Leu Ala Gly Phe Phe Ala Leu Phe
            340                 345                 350

Gln Ser Phe Leu Asn Ala Leu Ala Glu Ile Met Arg Phe Gly Asp Arg
        355                 360                 365

Ser Phe Tyr Asp Asp Trp Trp Asn Ser Glu Ser Leu Gly Ala Tyr Trp
    370                 375                 380

Arg Thr Trp Asn Lys Pro Val Tyr Thr Tyr Phe Lys Arg His Val Tyr
385                 390                 395                 400

Met Pro Met Ile Gly Arg Gly Trp Ser Pro Ala Ala Ser Phe Ala
                405                 410                 415

Val Phe Phe Val Ser Ala Val Leu His Glu Ile Leu Val Gly Val Pro
            420                 425                 430

Thr His Asn Ile Ile Gly Val Ala Phe Phe Gly Met Phe Leu Gln Leu
        435                 440                 445

Pro Leu Ile Ala Ile Thr Thr Pro Leu Glu Lys Met Lys Leu Gly His
    450                 455                 460

Gly Gly Arg Ile Leu Gly Asn Val Ile Phe Trp Val Ser Phe Thr Ile
465                 470                 475                 480

Phe Gly Gln Pro Phe Ala Ala Leu Met Tyr Phe Tyr Ala Trp Gln Ala
                485                 490                 495

Lys Tyr Gly Ser Val Ser Arg Leu Pro Gln Met Val His His
            500                 505                 510

<210> SEQ ID NO 76
<211> LENGTH: 1533
<212> TYPE: DNA
<213> ORGANISM: Trichoderma virens

<400> SEQUENCE: 76
atggcgcctc ctgcagagtc ctccacgacg acaagcgtcg aggcctctac cggctccgtg      60
tctcgccgcc acgcctcaca aagtgaagca gatctaacgt cggtggagcc cgtcaacggc     120
acgaccaaga accggctctc caagacaccg ccgaagaaat atcgccatgt cgctgcggtg     180
cattcccaga cgcggccgtc gtgcctgagc catgattccc ctgcggctcc cagctttctc     240
ggattccgca atctcatggt cattgtgctg gttgttggca atctccgatt gatgattgag     300
aatattcaaa gtacggcgt cttaatttgc atcaggtgtc acgactacag acgtcaagat      360
gtgctcttgg tgtcttttgct ttattttctt atccccctgcc atttgtttgc agcatacctg    420
atagagctgg tcgctgccaa gcaggctgag ggatccagga agcgaatcaa ggacaacaac      480
tctggcccgt cagaggcaga gcgcaagaag ttccactcaa tctgggttct tgcggctttg      540
gcccatggaa tcaacatcac tcttgcccctt gcaattacca ccgttgtggt ctacttttac      600
gtctatcatc cgctgattgg cactttgacc gagatgcatg ccatcattgt gtggctcaag      660

-continued

```
acggcatcat atgcattcac caaccgagat cttcgtcacg cctatctgca tccagttgag    720
ggagaggaag tgcctgattt gtacaaatcc tgccctatc cacaaaacgt gacgatgaag    780
aacttggtat acttctggtg ggctccgact ctggtgtacc aacctgttta tccgcggacc    840
gacaagattc gatgggtgtt cgtgtttaag cgactaggag agatcttttg ccttgctgtg    900
ttcatttggg ttgccagtgc ccaatatgcc accccgtttt gcgcaactc tctcgacaag    960
attgcctctc ttgatttgcc caacatcttg gagcggctta tgaaactctc gacaatctct   1020
ttggtcatct ggctggccgg cttctttgcg ctcttccaat cttcttaaa cgcccttgcc   1080
gagataatga ggtttggcga taggtcattc tacgacgact ggtggaacag tgagagcttg   1140
ggcgcctact ggaggacgtg gaacaagcct gtttatactt acttcaagcg ccatgtctat   1200
atgcccatga tcggacgagg ctggagcccg gccgctgcca gtttcgcagt cttttttgtt   1260
tctgccgttc ttcatgaaat tcttgttggt gttccaacac ataacattat cggcgtcgct   1320
ttcttcggca tgttccttca gcttcctctc atcgccatta ctactccgct ggagaagatg   1380
aaactcggtc atggtggccg cattcttgga atgtcatat tttgggtttc gtttacaatc   1440
tttggacagc cattcgcggc cctgatgtat ttctacgctt ggcaggccaa gtatggcagc   1500
gtgagtaggt tacctcagat ggtgcaccac taa                               1533
```

<210> SEQ ID NO 77
<211> LENGTH: 579
<212> TYPE: PRT
<213> ORGANISM: Arxula adeninivorans

<400> SEQUENCE: 77

```
Met Ile Arg Ala Ala Tyr Gly Ser Val Ser Arg Ala Arg Asp Ser Leu
 1               5                  10                  15

Thr Leu Arg Ala Pro Ser Phe Pro Thr Thr Ala Val Glu Val Arg Asp
             20                  25                  30

Lys Ile Leu Trp Ile Leu Tyr Ala Trp Ile Glu Met Phe Thr Asp Val
         35                  40                  45

Phe Ser Phe Trp Thr Glu Lys Val Trp Gly Tyr Val Ser Thr Pro Thr
     50                  55                  60

Lys Glu Ser Ile Leu Arg Lys Gln Leu Asp Glu Ala Lys Ser Tyr His
 65                  70                  75                  80

Glu Trp Glu Glu Leu Ser Tyr Lys Leu Asp Ser Ile Leu Gly Asn Asp
                 85                  90                  95

Ile Trp Arg Gln Asn Pro Val Ser Arg Lys Tyr Asp Tyr Arg Leu Ile
            100                 105                 110

Ser Thr Arg Leu Lys Glu Leu Val Ala Ala Arg Asp Asn Arg Asn Ile
        115                 120                 125

Glu Leu Leu Met Asp Arg Leu Arg Ser Gly Leu Leu Arg Asn Ile Gly
    130                 135                 140

Ser Ile Ala Ser Thr His Leu Tyr Asn Arg Ala Tyr Ser Gly Thr Lys
145                 150                 155                 160

Leu Leu Ile Glu Asp Tyr Ile Asn Val Val Ile Gln Cys Leu Glu Tyr
                165                 170                 175

Val Glu Arg Gly Gly Arg Pro Leu Thr Ala Ser Ala Ser Lys Ile Pro
            180                 185                 190

Asn Gly Gly Glu Pro Pro Ser Pro Arg Thr Tyr His Lys Pro Met Ile
        195                 200                 205

Thr Arg Gln Arg Lys Leu Asn Phe Phe Asn Asp Thr Arg Gln Ser Phe
    210                 215                 220
```

```
Gly Ser Thr Ala Val Val Leu His Gly Gly Ser Leu Phe Gly Leu Cys
225                 230                 235                 240

His Ile Gly Met Ile Lys Thr Leu Phe Asn Gln Gly Leu Leu Pro Arg
            245                 250                 255

Ile Val Cys Gly Ser Thr Val Gly Ala Leu Val Ala Ser Leu Val Cys
        260                 265                 270

Ser Cys Val Asp Glu Glu Val Tyr Glu Thr Leu Asp Asn Val Ser Ser
    275                 280                 285

Glu Met Ser Pro Leu Arg Gln Gly Tyr Thr Asp Ile Lys Tyr His Ser
290                 295                 300

Val Ala Glu Gly Val Ile Ser Ser Met Cys Pro Pro Glu Ile Leu Ile
305                 310                 315                 320

Phe Glu Gln Tyr Ile Arg Glu Lys Leu Gly Asp Leu Thr Phe Glu Glu
                325                 330                 335

Ala Tyr Gln Arg Thr Gly Arg Ile Leu Asn Ile Pro Val Thr Pro Lys
            340                 345                 350

Ala Lys Pro Gly Gln Val Ala Pro Val Pro Thr Leu Leu Asn Tyr
        355                 360                 365

Leu Ser Ser Pro Asn Val Val Trp Ser Ala Ala Gln Cys Ser Ile
370                 375                 380

Gly Thr Gly Ile Ile His Lys Lys Val Glu Leu Leu Val Lys Gly Leu
385                 390                 395                 400

Asp Gly Gln Leu Lys Pro Tyr Leu Asp Ala Asp Ile Glu Tyr Thr
                405                 410                 415

Pro Ala Asn Gln Ala Val Tyr Ala Ala Asp Arg Glu Ser Pro Tyr Thr
            420                 425                 430

Arg Leu Ser Glu Leu Phe Asn Val Asn Asn Tyr Ile Val Ser Val Ala
            435                 440                 445

Arg Pro Tyr Phe Ala Pro Ile Leu Leu Ser Asp Phe Lys Tyr Arg Ala
450                 455                 460

Ala Lys Ser Phe Lys Thr Arg Phe Leu Lys Leu Thr Arg Leu Glu Leu
465                 470                 475                 480

Gln Tyr Arg Leu Asn Gln Leu Ser Gln Leu Gly Leu Val Pro Pro Met
                485                 490                 495

Ile Gln Gln Trp Phe Val Asp Gly Asn Ile Pro Ala Gly Phe Gln Val
            500                 505                 510

Thr Val Pro Glu Leu Pro Ser Leu Ile Arg Asp Ile Gly Lys Val
        515                 520                 525

Phe Asp Ser Asp Asn Ile Lys Glu Lys Val Asp Tyr Trp Ile Lys Ile
530                 535                 540

Gly Glu Arg Ser Val Trp Pro Val Leu Asn Ile Ile Trp Ala Arg Cys
545                 550                 555                 560

Ala Ile Glu Phe Val Leu Asp Asp Leu Tyr His Ser Arg Arg Lys Asp
                565                 570                 575

Glu Leu Asp

<210> SEQ ID NO 78
<211> LENGTH: 1740
<212> TYPE: DNA
<213> ORGANISM: Arxula adeninivorans

<400> SEQUENCE: 78
atgattaggg ctgcctacgg gtcagtgtcc agggcccgag attctttaac gttgagggct    60
```

```
ccatctttc  ctaccactgc  tgtggaggtc  cgtgacaaga  ttctatggat  tctgtatgcc   120
tggattgaaa  tgttcacgga  cgtctttagc  ttctggacgg  agaaggtgtg  gggttatgtt   180
tctactccta  ctaaagaaag  cattcttaga  aagcaactcg  acgaggcaaa  atcataccat   240
gaatgggagg  agctcagcta  caaactagac  tcaattttag  gaacgatat  ttggcgacag   300 aaccctgtta  gccgaaagta  tgactatcgc  ctgatttcta  cccgcctcaa  ggaattggtt   360
gctgctaggg  ataatcgcaa  cattgaattg  ctaatggatc  ggctaaggtc  aggcctgctt   420
cgtaatattg  gatcgattgc  aagtactcat  ctctacaacc  gagcgtattc  gggcacaaaa   480
ctgttaattg  aggattacat  taatgtagtg  attcaatgcc  tggagtatgt  tgaacggggc   540
ggcaggccat  tgactgcttc  agcatccaag  attcccaatg  gcggtgaacc  ccttctcca    600 cgaacctacc  ataagcccat  gattaccaga  cagcgcaagc  tcaacttctt  caatgataca   660
cgccagtcgt  ttggaagtac  agctgtggta  cttcacggcg  ggtccttgtt  tggactttgc   720
catattggca  tgattaaaac  attgttcaac  cagggtctac  ttcctcgcat  agtctgtggc   780
tccacagtgg  gagcactagt  agcgagtcta  gtatgctcct  gtgtggatga  agaggtgtat   840
gagactttgg  ataatgtgtc  ttcggaaatg  tctcctctcc  gccaaggata  cactgatata   900
aagtaccatt  cggtagccga  aggggtcatt  tcatcaatgt  gtccgccaga  gattttgatt   960
tttgaacagt  acatccgaga  aaaactcgga  gacctgacat  tgaagaagc  atatcaacgc  1020 accggccgca  ttcttaatat  cccagtgaca  ccaaaggcaa  aaccaggtca  ggtagcacca  1080
ccagtcccga  cgctcctgaa  ttatttgtcg  agcccgaatg  ttgtagtatg  gtcagcagcg  1140
caatgcagca  ttggaacggg  gattattcac  aagaaggttg  aactttagt  aaaaggtctg  1200 gatggtcaat  taaaacctta  tttggatgcg  gatgatattg  aatacactcc  tgcaaatcaa  1260
gctgtatacg  ctgctgatcg  cgagagtccc  tatacaagat  tgtctgagct  gttcaatgtg  1320
aacaattaca  ttgtatcagt  agctcgcccc  tactttgccc  caattctgct  ttcggatttc  1380
aagtaccgtg  cagctaaaag  cttcaagacc  cggttcctca  aactaacccg  tctggagtta  1440
cagtatcgtc  tcaatcagct  gtctcaattg  gggctggttc  cgcccatgat  tcaacaatgg  1500
tttgtggacg  gtaacattcc  cgccgggttc  caagttaccg  tggtgcctga  attaccctca  1560
cttattagag  acatcggcaa  ggtttttcgat  tcggataata  taaggagaa  ggtcgactac  1620 tggattaaga  tcggtgagcg  cagtgtgtgg  ccagtgctga  atattatctg  ggcaaggtgc  1680
gcaattgagt  ttgtgctcga  cgatctatat  cacagccgac  gtaaagacga  actcgactag  1740
```

<210> SEQ ID NO 79
<211> LENGTH: 633
<212> TYPE: PRT
<213> ORGANISM: Arxula adeninivorans

<400> SEQUENCE: 79

```
Met Asn Pro Phe Asp Val Asp Tyr Thr Asn Arg Asp His Leu Val Asp
1               5                   10                  15

Phe Glu Arg Ala Leu His Glu Asp Glu Ala Ser His Ile Ile Ser Val
            20                  25                  30

Asn Asp Trp Ala Pro Val His Ala Pro Leu Lys Arg Arg Leu Arg Arg
        35                  40                  45

Lys Pro Thr Asp Ser Asp Pro Gly Thr Gly Leu Gly Tyr Thr Leu Leu
    50                  55                  60

Arg Trp Pro Ile Leu Val Ala Ile Ala Leu Trp Leu Ala Leu Leu Ala
65                  70                  75                  80
```

```
Phe Val Tyr Ala Ile Val Arg Phe Trp Val Ala Leu Phe Glu Tyr Phe
                 85                  90                  95

Val Thr Trp Arg Gly Pro Arg Arg Asn Leu Arg Glu Lys Leu Arg Ser
            100                 105                 110

Ala Arg Ser Tyr Glu Glu Trp Ile Ser Ala Ala Lys Val Leu Asp Asp
        115                 120                 125

His Leu Gly Asn Thr Ser Trp Lys His Asn Pro Lys Phe Ser Arg Tyr
    130                 135                 140

Asp Tyr Arg Thr Ile Asp Arg Ile Thr Asn Ser Leu Arg Gln Leu Arg
145                 150                 155                 160

Asn Gln Asn Lys Ala Glu Glu Val Gly Ser Ile Leu Gln Gly Cys Val
            165                 170                 175

Lys His Asn Phe Ala Gly Thr Gln Gly Gln Pro Leu Tyr Ser Gln Cys
            180                 185                 190

Tyr Tyr Gly Thr Lys Asp Leu Val Glu Glu Phe Asn Ser Glu Ile Val
        195                 200                 205

Lys Ser Leu Asp Tyr Leu Ala Thr His Pro Asp Leu Ser Pro Gln Ser
    210                 215                 220

Arg Arg Leu Leu Phe Lys Met Phe Ser Lys Asn Phe Gly Lys Thr Ala
225                 230                 235                 240

Leu Cys Leu Ser Gly Gly Ala Thr Phe Ala Tyr Arg His Phe Gly Val
            245                 250                 255

Val Lys Ala Leu Leu Glu Gln Gly Leu Leu Pro Asn Ile Ile Ser Gly
            260                 265                 270

Thr Ser Gly Gly Gly Leu Val Ala Ala Leu Val Gly Thr Arg Thr Asn
        275                 280                 285

Ser Glu Leu Arg Glu Leu Leu Thr Pro Gln Leu Ala Asp Lys Ile Thr
    290                 295                 300

Ala Cys Trp Glu Lys Phe Pro Lys Trp Val Tyr Arg Phe Tyr Ser Thr
305                 310                 315                 320

Gly Ala Arg Phe Asp Ala Val Asp Trp Ala Glu Arg Ser Cys Trp Phe
            325                 330                 335

Thr Leu Gly Ser Leu Thr Phe Arg Glu Ala Tyr Asp Arg Thr Gly Lys
        340                 345                 350

Ile Leu Asn Ile Ser Thr Val Pro Ala Asp Pro Asn Ser Pro Ser Ile
    355                 360                 365

Leu Cys Asn Tyr Ile Thr Ser Pro Asp Cys Val Ile Trp Ser Ala Leu
    370                 375                 380

Leu Ala Ser Ala Ala Val Pro Gly Ile Leu Asn Pro Val Val Leu Met
385                 390                 395                 400

Met Lys Thr Lys Lys Gly Asn Leu Val Pro Tyr Ser Phe Gly Asn Lys
            405                 410                 415

Trp Lys Asp Gly Ser Leu Arg Thr Asp Ile Pro Val His Ala Leu Asn
            420                 425                 430

Val Tyr Phe Asn Val Asn Phe Thr Ile Val Ser Gln Val Asn Pro His
        435                 440                 445

Ile Ser Leu Phe Met Tyr Ala Pro Arg Gly Thr Val Gly Arg Pro Val
    450                 455                 460

Ser His Arg Gln Gly Lys Gly Trp Arg Gly Phe Leu Gly Ser Ala
465                 470                 475                 480

Leu Glu Asp Met Leu Lys Leu Glu Ile Arg Lys Trp Leu Lys Leu Met
            485                 490                 495

Lys Asn Leu Ser Leu Met Pro Arg Phe Phe Asn Gln Asp Trp Ser Ser
```

```
                    500             505             510
Val Trp Leu Gln Thr Phe Glu Gly Ser Val Thr Leu Trp Pro Arg Ile
            515                 520                 525

Arg Leu Lys Asp Phe Tyr Tyr Ile Leu Ser Asp Pro Thr Arg Glu Gln
        530                 535                 540

Met Glu Thr Met Ile Ile Ser Gly Gln Arg Cys Thr Phe Pro Lys Leu
545                 550                 555                 560

Leu Phe Ile Lys His Gln Val Asn Ile Glu Arg Ala Ile Asp Arg Gly
                565                 570                 575

Arg Lys His Asn Ala Lys Ala Arg Glu Glu Asn Gly Pro Gln Leu Arg
            580                 585                 590

Arg Val Asn Pro Phe Leu His Asp Leu Asp Asp Arg Val Tyr His Ser
        595                 600                 605

Ser Ser Ser Val Asp Pro Arg Glu Phe Gln Asp His Asp Asp Glu
            610                 615                 620

Asp Asp Asp Ser Thr Asp Ser Ser Met
625                 630

<210> SEQ ID NO 80
<211> LENGTH: 1902
<212> TYPE: DNA
<213> ORGANISM: Arxula adeninivorans

<400> SEQUENCE: 80
atgaacccgt tgatgtaga ttacacaaac agggaccatc tggtcgactt tgaacgagct      60
ttgcacgaag atgaggcttc ccatattata tcggtaaacg actgggctcc agtgcatgct    120
cctctcaagc gacggttgag acgcaagccg acagattcgg atcctgggac aggattagga    180
tacactttgc ttagatggcc tattctggtg caattgcgc tgtggctggc cctgttagca     240
tttgtgtacg ccatagtgag gttttgggtc gctctgtttg agtactttgt tacctggcga    300
ggaccccggc gcaatcttcg tgaaaagcta cgcagcgctc gtagttacga ggaatggatt    360
agtgctgcca agttcttga tgaccatcta ggaaatactt cttggaagca aacccaaag     420 ttctctcgat acgactaccg tactattgat cgcatcacta actcactgcg gcaactgcga    480
aaccagaaca aggccgagga ggttggctct attctacaag gatgcgtcaa gcacaacttt    540
gctggaactc agggccaacc tttgtactct cagtgctact atggcacaaa ggacctggta    600
gaggagttca attctgaaat tgtgaaatcg ctcgattacc tggcaaccca tccagacctg    660
agtcctcaat ctagacgtct tttgttcaaa atgttttcca agaatttttgg aaagacggca    720 ttgtgcctct ctggaggggc aacatttgcc tatagacatt tcggagttgt taaagcgctc    780
ttggaacagg gcttgctgcc taatattatt tctggtactt ctggcggagg attggtagct    840
gcgctagttg gtaccagaac aaatagtgaa ctccgtgagc ttctcactcc tcaactggcc    900
gacaagatca ccgcctgctg gaaaagttc ccaaaatggg tttatagatt ctacagcacc     960
ggcgctcgat tcgatgccgt cgactgggct gaacggtctt gctggtttac actaggaagc   1020
ctgactttta gagaggccta cgatcgaact ggaaagatcc tcaacatttc cactgttcct   1080
gctgacccta ttcccttc aatcctctgc aattacatta cttctcccga ctgtgtcatc     1140
tggtcggctt tacttgcttc tgctgcagta ccgggaattc tgaacccagt ggtgctcatg   1200
atgaagacga aaaagggcaa tctggtacct tacagctttg gtaacaagtg aaggatggt    1260 tctctccgaa ctgatattcc tgtccacgca ctcaacgtgt actttaacgt caacttcacc   1320
atcgtgtccc aggtcaaccc tcacatttct ctgttcatgt atgccccgcg gggaactgtg   1380
```

```
ggtaggccag tatctcaccg tcagggtaaa ggctggcgag gtgggttcct aggctcagct   1440
ttggaagaca tgctgaagct ggaaattcgt aaatggctca aactcatgaa aaaccttagt   1500
cttatgccac ggttttcaa tcaagattgg tcttcagtat ggcttcaaac gttcgaggga    1560
tccgtcacct tgtggccaag gatcaggcta aaggactttt attatattct gtctgatccc   1620
actcgggaac aaatggaaac catgatcatt agtggacagc gatgcacatt cccaaagctc   1680
ttgttcatca agcaccaagt caacatagag cgggcaattg accgtggaag aaagcacaat   1740
gcaaaagcca gggaggaaaa tggtccccag cttagacggg taaacccatt cctgcacgac   1800
ttggatgacc gtgtatacca ttccagctct agcgtggacc ctcgcgagtt tcaggatgat   1860
cacgatgatg aagacgacga cagcactgat tctagcatgt aa                      1902
```

<210> SEQ ID NO 81
<211> LENGTH: 662
<212> TYPE: PRT
<213> ORGANISM: Arxula adeninivorans

<400> SEQUENCE: 81

```
Met Gln Ser Leu Asp Leu Leu Asp Asp Arg Ser Trp Val Pro Asn Tyr
1               5                   10                  15

Ala Arg Val Gly Leu Lys Ser Leu Lys Glu Tyr Leu Val Ser His Arg
            20                  25                  30

Tyr Gln Ser Glu Glu Ala Arg Lys His Ala Glu Ala Leu Glu Arg Trp
        35                  40                  45

Thr Lys Ser Gln Ala Gln Ala Glu Thr Tyr Glu Gln Trp Leu Phe Ala
    50                  55                  60

Ser Glu Gln Leu Asp Lys Leu Ser Gly Asn Asp Lys Trp Lys Glu Asp
65                  70                  75                  80

Pro Val Ser Pro Tyr Tyr Asp Ser Val Leu Val Gln Gln Arg Leu Gln
                85                  90                  95

Gln Leu Arg Asp Ala Arg Val Asn Ser Asn Met Asp Glu Leu Leu Tyr
            100                 105                 110

Leu Val Arg Thr Ser Leu Gln Arg Asn Leu Gly Asn Met Gly Asp Pro
        115                 120                 125

Arg Leu Tyr Val Arg Thr His Thr Gly Ser Lys Thr Leu Ile Glu Gln
    130                 135                 140

Tyr Ile Ala Glu Val Glu Leu Ala Leu Asp Thr Leu Leu Ser Cys Gly
145                 150                 155                 160

Pro Gly Thr Phe Ser Pro Lys Val Leu Leu Ser Asn Leu Ile Gln Thr
                165                 170                 175

Arg Lys Ala Phe Gly Arg Thr Ala Leu Val Leu Ser Gly Gly Ser Thr
            180                 185                 190

Phe Gly Ile Leu His Ile Gly Val Met Arg Glu Leu His Arg Ala His
        195                 200                 205

Leu Leu Pro Gln Val Ile Ser Gly Ser Ser Ala Gly Ser Ile Phe Ala
    210                 215                 220

Ser Met Leu Cys Ile His Leu Glu Asp Glu Ile Glu Glu Leu Leu Gln
225                 230                 235                 240

Leu Pro Leu His Lys Glu Ser Phe Glu Ile Phe Glu Pro Ala Gly Glu
                245                 250                 255

Arg Glu Gly Leu Met Val Arg Leu Ala Arg Phe Leu Lys His Gly Thr
            260                 265                 270

Trp Phe Asp Asn Lys Tyr Leu Ser Thr Thr Met Arg Glu Leu Leu Gly
```

```
                    275                 280                 285
Asp Leu Thr Phe Gln Glu Ala Tyr Tyr Arg Thr Gln Arg Ile Leu Asn
            290                 295                 300

Val Thr Val Ser Pro Ser Ser Met His Glu Met Pro Lys Ile Leu Asn
305                 310                 315                 320

Tyr Leu Thr Ala Pro Asn Val Leu Ile Trp Ser Ala Val Cys Ala Ser
                325                 330                 335

Cys Ser Val Pro Phe Val Phe Asp Ser His Asp Ile Leu Ala Lys Asn
            340                 345                 350

Pro Arg Thr Gly Glu Phe Tyr Ser Trp Asn Ala Ser Thr Phe Ile Asp
        355                 360                 365

Gly Ser Val Tyr Asn Asp Leu Pro Leu Ser Arg Leu Ala Glu Met Phe
        370                 375                 380

Asn Val Asn His Phe Ile Ala Cys Gln Val Asn Pro His Val Val Pro
385                 390                 395                 400

Phe Val Lys Phe Ala Glu Thr Met Ser Leu Val Glu Ala Arg Pro Thr
                405                 410                 415

Thr Thr Glu Pro Gly Ser Leu Thr Lys Leu Trp His Ser Thr Gln Leu
            420                 425                 430

Ala Leu Ser Ser Glu Ile Ser His Tyr Leu Asp Leu Ala Ala Glu Met
        435                 440                 445

Gly Leu Phe Lys Asn Ile Ser Ser Lys Leu Arg Ser Val Leu Asp Gln
        450                 455                 460

Gln Tyr Ser Gly Asp Ile Thr Ile Leu Pro Glu Leu Tyr Leu Ser Glu
465                 470                 475                 480

Phe Gly Gln Ile Phe Lys Asn Pro Ser Lys Glu Phe Phe Gln Lys Ala
                485                 490                 495

Glu Leu Arg Ala Ala Arg Ala Thr Trp Pro Lys Met Ser His Ile His
            500                 505                 510

Asn Arg Val Ala Ile Glu Leu Ala Leu Val Lys Ala Ile His Lys Leu
        515                 520                 525

Arg Ala Arg Ile Val Ser Gln Ser Val His Glu Pro Gly Ser Ser Leu
        530                 535                 540

Gln Val His Ala Ala Asn Asp Glu Gly Thr Leu Ala Pro Ile Arg Arg
545                 550                 555                 560

Arg His Ser Ser Thr Lys Leu His His Arg Gln Arg Ser Asp Gly
                565                 570                 575

Met Ala Val Lys Tyr Leu Val Arg Arg His Ser Leu Gln Tyr Phe Gly
            580                 585                 590

Thr Glu Gly Pro Gly Pro Ala Ala Leu Ser Arg Lys Lys Ser Ser Ala
        595                 600                 605

Gly Leu Thr Gln Ala His Thr Pro Thr Pro Ser Leu Thr Asn Ser Val
        610                 615                 620

Ser Val Gly Gly Ser Pro Arg His Arg Arg Phe Thr Thr Ser Ser Arg
625                 630                 635                 640

Gln Ser Ser Gly Asp His Leu Glu Met Phe Ser Gln Asn His Pro Leu
                645                 650                 655

Glu Arg Ile Ser Thr Gly
            660

<210> SEQ ID NO 82
<211> LENGTH: 1989
<212> TYPE: DNA
<213> ORGANISM: Arxula adeninivorans
```

<400> SEQUENCE: 82

```
atgcaatccc tggacctatt agacgacagg tcctgggtcc ccaattatgc gcgtgtgggc    60
ctgaaatcgc taaaagaata cttggttagc catagatatc agtctgaaga agctcgaaag   120
catgccgaag cgttagaaag atggacaaag tctcaggctc aggcggagac atacgaacag   180
tggctatttg cttcggagca gctcgacaag ctgtctggga acgacaagtg gaaagaggac   240
ccggtgtccc catattatga cagtgtgcta gtacaacagc ggttacagca gctccgagat   300
gctagggtga atagtaacat ggacgagctg ctgtatttgg tccgcactag cttgcaaaga   360
aacttgggta acatgggtga tcctcgacta tacgtgagga cccatactgg ctctaagacg   420
ctcattgaac aatatattgc tgaggtagaa ctggcattag acactctgct gagctgcgga   480
ccggggacgt tttcacccaa agttctgtta tccaatctta ttcagacaag aaaggcgttt   540
ggacgaacag ccctggtgct ttctggaggt agtacgtttg aattttaca tattggtgta    600
atgcgagagc ttcaccgagc ccatctgtta ccgcaggtca tttctggatc gtcggccgga   660
tccatctttg cgtccatgct atgtattcac ttagaagacg agattgaaga actactgcaa   720
ctgcctctac acaaggaaag cttgaaatc ttcgaacctg ctggagaacg agaaggacta    780
atggttcggc tggcacggtt cctcaaacat ggcacttggt tcgacaacaa gtatcttagc   840
acaactatgc gagagcttct aggagacctc actttccagg aggcctacta ccgaacgcag   900
cgaattctaa atgtcactgt gtctccttcg agtatgcacg aaatgccgaa gattctcaac   960
tatctgaccg ctcctaacgt gctcatttgg tcggcagtgt gtgcatcgtg ctcagtacca  1020
tttgtgtttg attctcacga cattctggca aaaaaccctc gaactgggga gttttattca  1080
tggaacgctt ctactttcat cgacgggagt gtgtataatg atctgccatt gtctcgacta  1140
gcggaaatgt ttaacgtgaa ccattttatt gcgtgccagg taaacccgca tgtggttcca  1200
ttcgtcaaat ttgccgagac aatgtcattg gtggaagctc gtcccactac tactgaaccg  1260
ggatcgttga caaagctatg gcacagtact cagctcgcgc tttctagtga gatctcacac  1320
tatctggatt tggctgctga aatgggcttg ttcaagaaca ttagttccaa gctgcgatcg  1380
gtgctagatc aacaatattc cggcgacatt actattcttc ccgaattata cctgtctgag  1440
tttggtcaga ttttcaaaaa cccatcaaag gagttcttcc agaaggcaga gcttcgagct  1500
gccagagcga catgggccaa gatgtccac attcacaacc gtgtggccat cgagttggct   1560
ttagtaaagg caattcacaa gcttcgtgcc cgtattgtat ctcagagcgt ccatgagcct  1620
ggcagttctc tacaagtaca tgctgctaat gacgaaggca ccctagcacc tattcgccgt  1680
cgccattctt cgaccaagct tcaccataga cgacaacggt ccgatggaat ggccgtgaaa  1740
tacttggtcc gcagacattc gctacagtac tttggcactg agggccctgg tcccgctgcg  1800
ctatctcgta aaaagagttc ggccgggctt acccaggctc atactcctac gccttcactg  1860
accaacagcg ttagtgtagg gggcagtcca aggcaccgtc gcttcactac tagctctaga  1920
cagtcctcag gagaccattt ggaaatgttc tctcaaaatc atccgctaga acgtatctct  1980
accggctga                                                          1989
```

<210> SEQ ID NO 83
<211> LENGTH: 332
<212> TYPE: PRT
<213> ORGANISM: Ricinus communis

<400> SEQUENCE: 83

-continued

```
Met Glu Val Ser Gly Leu Gly Cys Phe Ser Ser Ala Ala Thr Pro Ser
1               5                   10                  15

Leu Cys Gly Ala Val Asp Ser Gly Gly Val Ser Ser Leu Arg Pro Arg
            20                  25                  30

Lys Ala Phe His Arg Val Ser Asp Ser Cys Leu Gly Phe Arg Asp Asn
        35                  40                  45

Gly His Leu Gln Tyr Tyr Cys Gln Gly Gly Phe Val Arg Cys Gly Gly
    50                  55                  60

Gly Asn Lys Lys Ser Ile Lys Lys Lys Leu Lys Leu Val Lys Ser Leu
65                  70                  75                  80

Ser Glu Asp Phe Ser Met Phe Pro His Asn Asn Ala Leu Leu His Gln
                85                  90                  95

Pro Gln Ser Ile Ser Leu Gln Glu Ala Ala Gln Gly Leu Met Lys Gln
            100                 105                 110

Leu Gln Glu Leu Arg Ala Lys Glu Lys Glu Leu Lys Arg Gln Lys Lys
        115                 120                 125

Gln Glu Lys Lys Ala Lys Leu Lys Ser Glu Ser Ser Ser Ser Ser Ser
    130                 135                 140

Ser Glu Ser Ser Ser Asp Ser Glu Arg Gly Glu Val Ile His Met Ser
145                 150                 155                 160

Arg Phe Arg Asp Glu Thr Ile Pro Ala Ala Leu Pro Gln Leu His Pro
                165                 170                 175

Leu Thr His His His Pro Thr Ser Thr Leu Pro Val Ser Pro Thr Gln
            180                 185                 190

Glu Cys Asn Pro Met Asp Tyr Thr Ser Thr His His Glu Lys Arg Cys
        195                 200                 205

Cys Val Gly Pro Ser Thr Gly Ala Asp Asn Ala Val Gly Asp Cys Cys
    210                 215                 220

Asn Asp Arg Asn Ser Ser Met Thr Glu Glu Leu Ser Ala Asn Arg Ile
225                 230                 235                 240

Glu Val Cys Met Gly Asn Lys Cys Lys Lys Ser Gly Gly Ala Ala Leu
                245                 250                 255

Leu Glu Glu Phe Gln Arg Val Leu Gly Val Glu Ala Ala Val Val Gly
            260                 265                 270

Cys Lys Cys Met Gly Asn Cys Arg Asp Gly Pro Asn Val Arg Val Arg
        275                 280                 285

Asn Ser Val Gln Asp Arg Asn Thr Asp Asp Ser Val Arg Thr Pro Ser
    290                 295                 300

Asn Pro Leu Cys Ile Gly Val Gly Leu Glu Asp Val Asp Val Ile Val
305                 310                 315                 320

Ala Asn Phe Phe Gly Leu Gly Leu Ala Pro Ala Ser
                325                 330
```

<210> SEQ ID NO 84
<211> LENGTH: 999
<212> TYPE: DNA
<213> ORGANISM: Ricinus communis

<400> SEQUENCE: 84

```
atggaagtct caggcctggg ctgcttctcc tcggctgcaa cgccatcttt gtgtggggcg      60
gtggattcag gcggagtatc ctctttgaga ccgaggaagg cattccatag ggtttctgat     120
tcttgtttag ggtttagaga taatggacat ctgcagtatt attgtcaagg aggatttgtc     180
aggtgcggag gagggaacaa gaaatctatc aagaaaaagt tgaaattagt gaagtccttg     240
```

```
tctgaggact tttccatgtt tcctcataac aatgctttgc tccatcaacc tcaatccatc    300
tccctccagg aagctgcaca aggattaatg aaacagctcc aagaattgcg agcaaaggag    360
aaggaattaa agaggcagaa gaaacaagag aaaaaagcca agctaaaatc tgaatcatcc    420
tcatcctcat cctctgaatc cagtagtgat agcgaacgtg gggaggttat tcacatgagc    480
cgcttcagag atgaaactat tcctgccgca ctacctcaat gcacccact tactcatcac    540 cacccaactt ccaccctacc agtctcccca acccaagaat gcaacccgat ggattacact    600
tcaacacatc atgaaaaacg atgctgcgtt ggaccaagca ccggtgccga taacgcagtc    660
ggtgactgtt gcaatgatag gaatagctcg atgacagagg aattgtcagc aaacagaatt    720
gaggtgtgca tgggtaataa gtgcaagaag tcgggaggtg cagcgttatt ggaggaattt    780
cagagggttt tgggtgtaga ggctgcagtt gttgggtgca agtgcatggg gaactgcagg    840
gacggtccta atgtaagggt caggaattct gtccaagaca gaaacacaga tgactctgtt    900 cgaacccccct ccaatcctct ctgcattggt gttggtttgg aggatgtgga tgttattgtg    960
gccaatttct ttgggttggg tctggcccct gcatcttaa                          999
```

<210> SEQ ID NO 85
<211> LENGTH: 345
<212> TYPE: PRT
<213> ORGANISM: Arachis hypogaea

<400> SEQUENCE: 85

Met Glu Val Ser Gly Ala Val Leu Arg Asn Val Thr Cys Pro Ser Phe
1               5                   10                  15

Ser Val His Val Ser Ser Arg Arg Gly Gly Asp Ser Cys Val Thr
            20                  25                  30

Val Pro Val Arg Met Arg Lys Lys Ala Val Val Arg Cys Cys Gly
        35                  40                  45

Phe Ser Asp Ser Gly His Val Gln Tyr Tyr Gly Asp Glu Lys Lys
    50                  55                  60

Glu Asn Gly Thr Ala Met Leu Ser Thr Lys Lys Leu Lys Met Leu
65              70                  75                  80

Lys Lys Arg Val Leu Phe Asp Asp Leu Gln Gly Asn Leu Thr Trp Asp
                85                  90                  95

Ala Ala Met Val Leu Met Lys Gln Leu Glu Gln Val Arg Ala Glu Glu
            100                 105                 110

Lys Glu Leu Lys Lys Lys Arg Lys Gln Glu Lys Glu Ala Lys Leu
        115                 120                 125

Lys Ala Ser Lys Met Asn Thr Asn Pro Asp Cys Glu Ser Ser Ser
    130                 135                 140

Ser Ser Ser Ser Glu Ser Glu Ser Glu Ser Glu Ser Glu Cys Asp
145                 150                 155                 160

Asn Glu Val Val Asp Met Lys Lys Asn Ile Lys Val Gly Val Ala Val
                165                 170                 175

Ala Val Ala Asp Ser Pro Arg Lys Ala Glu Thr Met Ile Leu Tyr Thr
            180                 185                 190

Ser Leu Val Ala Arg Asp Val Ser Ala Asn His His His Asn Ala
    195                 200                 205

Val Glu Leu Phe Ser Arg Asn Asn Asp Ile Ser Val Gly Ser Ile Asn
        210                 215                 220

Gly Gly Leu Lys Asn Glu Asn Thr Ala Val Ile Thr Thr Glu Ala Ile
225                 230                 235                 240

```
Pro Gln Lys Arg Ile Glu Val Cys Met Gly Asn Lys Cys Lys Lys Ser
            245                 250                 255

Gly Ser Ile Ala Leu Leu Gln Glu Phe Glu Arg Val Val Gly Ala Glu
            260                 265                 270

Gly Gly Ala Ala Ala Val Val Gly Cys Lys Cys Met Gly Lys Cys
        275                 280                 285

Lys Ser Ala Pro Asn Val Arg Ile Gln Asn Ser Thr Ala Asp Lys Ile
            290                 295                 300

Ala Glu Gly Phe Asn Asp Ser Val Lys Val Pro Ala Asn Pro Leu Cys
305                 310                 315                 320

Ile Gly Val Ala Trp Arg Met Leu Lys Pro Leu Trp Leu Arg Phe Leu
                325                 330                 335

Gly Glu Asn Gln Glu Ser Thr Asn Glu
            340                 345

<210> SEQ ID NO 86
<211> LENGTH: 1038
<212> TYPE: DNA
<213> ORGANISM: Arachis hypogaea

<400> SEQUENCE: 86
```

| | | | | | |
|---|---|---|---|---|---|
| atggaggttt | caggcgccgt | tctaaggaat | gtcacgtgcc | cttcctttc | tgtgcacgtg | 60 |
| agttcccgtc | gtcgtggtgg | tgatagttgt | gttacagtgc | cggtgaggat | gagaaaaag | 120 |
| gcggtggtgc | gttgttgctg | cgggttcagt | gattcggggc | atgtgcagta | ttacggggac | 180 |
| gagaagaaga | aggagaatgg | aaccgctatg | ttgagcacca | agaagaagct | caagatgctg | 240 |
| aagaaacgtg | tccttttcga | tgatcttcaa | ggaaacctga | cttgggatgc | tgctatggtt | 300 |
| ttgatgaagc | agctagagca | agtaagggca | gaggagaagg | aattgaagaa | aaaaggaag | 360 |
| caagagaaga | aggaggcaaa | actcaaagcc | tctaagatga | acaccaatcc | tgattgcgaa | 420 |
| tcgtcatcgt | catcgtcatc | atctgaatct | gaatctgaat | caagtgagag | tgaatgtgac | 480 |
| aatgaggtgg | ttgacatgaa | gaagaacatt | aaggttggtg | ttgccgttgc | tgttgccgat | 540 |
| tccccacgaa | aggcggaaac | catgattcta | tacacctccc | ttgttgcccg | agatgttagt | 600 |
| gctaatcatc | atcatcataa | tgccgtggaa | ttattctcta | gaaacaatga | catatcagtt | 660 |
| ggaagcatta | atggtggcct | taagaatgag | aatactgcgg | ttattaccac | tgaagctatt | 720 |
| cctcagaaga | ggattgaggt | atgcatggga | aacaagtgca | agaaatccgg | atctattgca | 780 |
| ttgttgcaag | aatttgagag | agtggttggt | gctgaaggag | gtgctgctgc | tgcagttgtt | 840 |
| ggatgcaagt | gcatggggaa | gtgcaagagt | gcacctaatg | tgaggattca | gaactctact | 900 |
| gcagataaaa | tagctgaggg | gttcaatgat | tcagttaagg | ttccagctaa | ccctctttgc | 960 |
| attggggttg | catggaggat | gttgaaacca | ttgtggctta | gattcttggg | cgagaatcag | 1020 |
| gaaagtacta | atgaataa | | | | | 1038 |

```
<210> SEQ ID NO 87
<211> LENGTH: 816
<212> TYPE: PRT
<213> ORGANISM: Yarrowia lipolytica

<400> SEQUENCE: 87

Met Phe Thr Ser Arg Val Ser Glu Ala Ser Thr Thr Asn Phe Ile Arg
1               5                   10                  15

Pro Thr Ala Arg Ser His Ile His Phe Phe Ala Phe Ile Ala Ala
            20                  25                  30
```

```
Thr Val His Gln Leu Leu Met Leu Tyr Gln Leu Gly Asp Gly
         35                  40                  45

Tyr Leu Lys Ser Phe Val Asp Thr Gly Ile Thr Leu Ala Gln Gln Ser
 50                  55                  60

Gly Leu Ser Gly Ile Val Asn Ala Leu Thr Ser Glu Ala Lys Leu Arg
 65                  70                  75                  80

Ile Asp Lys Arg Ser Ile Ile Lys Lys Leu Leu Glu Asp Gln Glu Asn
                 85                  90                  95

Ala Glu Ser Tyr Phe Asp Trp Leu Lys Ala Ser Ser Glu Leu Asp Tyr
             100                 105                 110

Leu Leu Gly Asn Gln Glu Trp Lys Glu Arg Asp Glu Cys Pro Ala Tyr
             115                 120                 125

Asp Tyr Glu Tyr Val Arg Leu Arg Leu Asp Glu Leu Arg His Ala Arg
130                 135                 140

Thr Asn Asn Asp Thr Thr Arg Leu Leu Tyr Leu Val Arg Thr Thr Trp
145                 150                 155                 160

Ser Arg Asn Leu Gly Asn Leu Gly Asp Val Lys Leu Tyr His Asn Ser
                 165                 170                 175

Phe Thr Gly Thr Lys Arg Leu Ile Glu Asp Tyr Ile Leu Glu Cys Glu
             180                 185                 190

Leu Ala Leu Asn Ala Leu Leu Ala Ala Gly Asn Asp Lys Ile Pro Asp
             195                 200                 205

Gln Glu Leu Leu Thr Glu Leu Leu Asn Thr Arg Lys Ala Phe Gly Arg
             210                 215                 220

Thr Ala Leu Leu Leu Ser Gly Gly Cys Leu Gly Leu Leu His Thr
225                 230                 235                 240

Gly Val Leu Gln Ala Leu Ser Asp Thr Ser Leu Leu Pro His Val Ile
                 245                 250                 255

Ser Gly Ser Ser Ala Gly Ser Ile Met Ala Ala Gly Leu Cys Ile His
             260                 265                 270

Lys Asp Glu Glu His Glu Ala Phe Ile Thr Glu Leu Met Glu Arg Asp
             275                 280                 285

Phe Asp Ile Phe Glu Glu Ser Gly Asn Glu Asp Thr Val Leu Glu Arg
             290                 295                 300

Val Ser Arg Met Leu Lys His Gly Ser Leu Leu Asp Asn Arg Tyr Met
305                 310                 315                 320

Gln Asp Thr Met Arg Glu Leu Phe Gly Asp Met Thr Phe Leu Glu Ala
                 325                 330                 335

Tyr Asn Arg Thr Arg Arg Ile Leu Asn Val Thr Val Ser Ser Ala Gly
             340                 345                 350

Ile Tyr Glu Met Pro Arg Leu Leu Asn Tyr Leu Thr Ala Pro Asn Val
             355                 360                 365

Leu Ile Trp Ser Ala Val Cys Ala Ser Cys Ser Val Pro Leu Ile Phe
             370                 375                 380

Asn Ala Tyr Thr Leu Leu Glu Lys Glu Pro Lys Thr Gly Ala Ile Gln
385                 390                 395                 400

Thr Trp Asn Ala Ser Ser Leu Arg Phe Ile Asp Gly Ser Val Tyr Ala
                 405                 410                 415

Asp Val Pro Ile Ala Arg Leu Ser Glu Met Phe Asn Val Asn His Phe
             420                 425                 430

Ile Val Ser Gln Val Asn Pro His Val Ala Pro Phe Leu Lys Leu Thr
             435                 440                 445

Glu Asp Lys Ala Asn Pro Asp Ser Val Asp Glu Ile Tyr Thr Leu Lys
```

```
             450              455              460
Leu Trp His Asn Phe Lys Thr Leu Val Thr Asp Glu Val Met His Gln
465                 470                 475                 480

Leu Gln Val Leu Tyr Glu Phe Gly Ile Phe Lys Asn Leu Cys Ser Lys
                485                 490                 495

Met Gly Gly Val Leu Ser Gln Arg Tyr Lys Gly Asp Ile Thr Ile Leu
                500                 505                 510

Pro Gln Val His Leu Ser Glu Leu Pro Gly Ile Leu Thr Asn Pro Thr
            515                 520                 525

Ala Ala Tyr Met Lys Asp Thr Asn Arg Arg Gly Ala Gln Ala Thr Tyr
        530                 535                 540

Arg Lys Ile Ser Leu Ile Arg Asn His Cys Ala Ile Glu Leu Ala Leu
545                 550                 555                 560

Asp Arg Ala Ile His Glu Leu Lys Ala Arg Met Leu Pro Ser Lys Leu
                565                 570                 575

Gly Ser Gly Arg Thr Ser Pro Gln Gly Thr Phe Lys His Ser Gln Ser
                580                 585                 590

Ser Asn Gln Ile Ser Ala Leu Lys Pro Pro Ser Arg His Met Ser Ala
            595                 600                 605

Ser Ser Ala Thr Thr Ala His Thr Arg Leu Arg Asn Arg Lys Ser Phe
        610                 615                 620

Ser His Ala Arg Ile Lys Ser Asp Ala Ala Val Phe Asp Lys Glu
625                 630                 635                 640

Pro Ile His Glu Thr Pro Lys Ser Ser Pro Gln Ser Ser Tyr Val Asn
                645                 650                 655

Leu His Arg Ser Ala Ser Glu Arg Ser Arg Arg Pro Lys Ser Ala Phe
                660                 665                 670

Asn Leu Gly Ser Leu Pro Thr Ser Pro Leu Tyr His Pro His Leu Thr
            675                 680                 685

His Ser Met Ser Met Gly Gly Ala Asn Gln Ala Pro Leu Tyr Asn Pro
        690                 695                 700

Gly Arg Gly Ser Val Ser Gln Asn Thr Ser Pro Gly Thr Lys Ile Pro
705                 710                 715                 720

Gly Asn Ala Asp Pro Ser Tyr Phe Asp Gly Pro Asn Asn Val Arg Phe
                725                 730                 735

His Trp Asp Ser Asp Asp Asp Val Arg Glu Thr Glu Phe Leu Asn
                740                 745                 750

Asn Met Ser Ser Ser Ser Arg Arg Val Ser Pro Val Gln Ser Arg
            755                 760                 765

Arg Ala Ser Val Asp Gly Leu Arg Asn Ser Val Ser Thr Ala Thr
        770                 775                 780

Ser Val Thr Asp Gly Ser Val Ser Ser Arg Pro Ser Arg Ala Trp Glu
785                 790                 795                 800

Ser Ile Ser Gln Leu Phe Glu Gly Asp Glu Asn Cys Ser Asp Ser Cys
                805                 810                 815
```

<210> SEQ ID NO 88
<211> LENGTH: 2451
<212> TYPE: DNA
<213> ORGANISM: Yarrowia lipolytica

<400> SEQUENCE: 88
atgttcacct ccagagtttc cgaagcaagc accaccaact ttatccggcc gacggcacgg    60
tctcacatcc actttttttt cgccttcatc gccgcaaccg tccaccaact gctgctcatg   120

-continued

```
ctctaccaac tgcttggaga cggctacctc aagtcgtttg tcgacacagg tatcacgctg      180
gcccaacagt cggggctttc gggtatcgtc aacgccttga cttcagaggc caaactgcgg      240
atcgataaac ggtccatcat caaaaagctg ctagaggacc aggaaaacgc cgagtcgtac      300
tttgactggc tcaaggcgtc cagcgaactc gactatctgc tcggcaacca ggaatggaag      360
gaaagagacg agtgtccagc ttacgattac gaatacgtcc gactccgatt ggacgaactg      420
agacacgccc gaaccaataa cgacaccacc cgactgcttt acctcgtgcg aacaacgtgg      480
agtagaaacc tcggcaacct cggagacgtc aagctctacc acaactcctt taccggaacc      540
aaacgactca tcgaagacta cattctggaa tgcgaactgg ctctcaacgc gctcctggca      600
gccggaaacg acaagatccc ggaccaggag ctgctcacgg agctgctcaa caccagaaag      660
gcatttggac gaactgccct tctgctgtcc ggcggaggat gtctcggtct gctccacacc      720
ggtgttctcc aggccctctc agacacatcg ctcttgcccc acgtcatatc gggttcgtcg      780
gcaggctcaa tcatggccgc gggactgtgc attcacaaag acgaagaaca cgaggctttc      840
atcaccgagc tcatggagcg agactttgac attttcgaag agtccggaaa cgaagacacg      900
gtgctcgaac gagtgtctcg aatgctcaaa catggatcgc tactcgacaa cagatatatg      960
caggacacta tgcgagaatt atttggcgac atgacctttc tggaggccta caaccggact     1020
cgccgtattc tcaacgttac ggtatcgtct gctggcatct acgaaatgcc tcgtttgctc     1080
aactacctga cggcccccaa cgtactcatt tggtcggctg tctgcgcctc ctgctcggtg     1140
cctctcattt tcaatgccta cactctgctt gaaaaggagc ccaaaacagg agctattcag     1200
acctggaacg cttcttcgct gcggttcatt gacggatccg tctatgccga cgtgcccatt     1260
gcgcgtctct cagaaatgtt caatgtaaat catttcattg tctcgcaggt aaaccctcac     1320
gttgctcctt tcctcaagct cacagaagac aaggccaacc cggactcggt cgacgaaatc     1380
tacacgctca gctttggca caacttcaag acgctggtca ccgacgaggt catgcaccag     1440
ttgcaggtgc tgtacgagtt tggcatcttc aagaacctgt gttcgaaaat gggaggcgta     1500
ctgtcccagc gatacaaggg agacatcaca atcctgcccc aggtccatct ctcagagctc     1560
ccgggaattc ttactaaccc cactgccgca tacatgaagg acaccaaccg acgaggtgcc     1620
caggccactt atcgaaagat ctcgctcatt cgaaaccact gtgccattga gttggcgctg     1680
gatcgagcta tccacgaact caaggcccgt atgctcccct ccaagcttgg atcaggacgt     1740
acatccccgc aaggtacttt taagcattcg cagtcgtcca accagatttc tgcgctcaaa     1800
cctccttctc gtcacatgtc tgcttcatcg gcaaccacag cacatacgcg tcttcggaac     1860
cgaaagtcgt tttctcatgc acgtatcaag agtgatgcgg ccgctgtgtt cgacaaggag     1920
cctattcacg agacgcccaa gtcgtcgcct cagagctcgt atgtcaactt gcaccgatct     1980
gcaagtgagc ggtcgagacg acccaagtct gcattcaatc tgggctctct gccgacctct     2040
cctctttatc atccgcatct gacccactcc atgtctatgg gggagccaa tcaggcgcct     2100 ctgtacaatc ctgggcgcgg ttctgtgtct cagaacacct cccctgggac caaaatcccc     2160
ggaaacgctg atccgtcgta ctttgatgga cccaacaatg tgcgtttcca ctgggacagc     2220
gacgacgacg atgtgcgaga dacggagttc ctcaacaaca tgtcttcgtc gtcttcacga     2280
agagtttctc ctgtccagag tcgtcgagcc agtgttgatg gactgcgaaa ctctgtcgta     2340
tccaccgcca ccagtgtcac cgacggtccc gtgtccagca gaccgtcccg agcgtgggag     2400
agcatttccc agctgtttga aggggacgag aactgttctg actcgtgcta a             2451
```

US 10,443,047 B2

INCREASING CELLULAR LIPID PRODUCTION BY INCREASING THE ACTIVITY OF DIACYLGLYCEROL ACYLTRANSFERASE AND DECREASING THE ACTIVITY OF TRIACYLGLYCEROL LIPASE

RELATED APPLICATIONS

This application is a § 371 national stage application based on PCT/US2015/028760, filed May 1, 2015, which claims the benefit of priority to U.S. Provisional Patent Application No. 61/987,098, filed May 1, 2014; and U.S. Provisional Patent Application No. 62/090,169, filed Dec. 10, 2014.

SEQUENCE LISTING

The instant application contains a Sequence Listing which has been submitted via EFS-Web and is hereby incorporated by reference in its entirety. Said ASCII copy is named NGX-030.01.txt and is 247 kilobytes in size.

BACKGROUND

Lipids have multiple industrial applications, including in the cosmetic and food industries, as well as serving as precursors for biodiesel and biochemical production. Microbial lipids are produced by many oleaginous organisms, including the well-characterized yeast *Yarrowia lipolytica*. Lipid yield in oleaginous organisms can be increased by up-regulation or down-regulation or deletion of genes implicated in the lipid pathway. For example, it was reported that up-regulation of native *Y. lipolytica* DGA1 significantly increased lipid yield and productivity (Metabolic Engineering 15:1-9 (2013)).

*Y. lipolytica* DGA1 is a type 2 diacylglycerol acyltransferase encoded by the *Y. lipolytica* diacylglycerol acyltransferase gene DGAT2. DGA1 is one of the key enzymes in the lipid pathway, and it is involved in the final step of triacylglycerol (TAG) synthesis. Triacylglycerols are the major form of storage lipids in *Y. lipolytica*. Recent data suggests that DGA1 efficiency may be a significant factor for high levels of lipid accumulation in oleaginous organisms (Metabolic Engineering 15:1-9 (2013)). Additionally, DGA1 genes from other species can be introduced into the host genome and have a significant effect on lipid production and composition. For example, other oleaginous yeast, such as *Rhodosporidium toruloides* and *Lipomyces starkeyi*, are able to accumulate significantly more lipids compared to wild type *Y. lipolytica* strains. It was demonstrated that overexpression in *Y. lipolytica* of DGA1 from organisms with higher native lipid production levels had a greater effect on *Y. lipolytica* lipid production than overexpression of native *Y. lipolytica* DGA1 (U.S. Ser. No. 61/943,664; incorporated by reference). Despite efforts to increase lipid yield in *Y. lipolytica* by overexpression of DGA1 from *Mortierella alpine*, no significant effect on lipid production levels has been reported (U.S. Pat. No. 7,198,937; incorporated by reference).

The deletion of genes involved in the breakdown of lipids or in pathways that draw flux away from lipid biosynthesis has also been studied. Dulermo et al. demonstrated that the deletion of the triacylglycerol lipase gene TGL3 nearly doubled the total lipid content accumulated by *Y. lipolytica* (Biochimica Biophysica Acta 1831:1486-95 (2013)). The TGL3 protein is one of two intracellular lipases responsible for the first step of triacylglyccrol degradation in *Y. lipolytica*.

SUMMARY

In some embodiments, the invention provides a transformed oleaginous cell comprising a first genetic modification, wherein said first genetic modification increases the activity of a native diacylglycerol acyltransferase or encodes at least one copy of a diacylglycerol acyltransferase gene native to the oleaginous cell or from a different species, and a second genetic modification, wherein said second genetic modification decreases the activity of a triacylglycerol lipase in the oleaginous cell.

In some aspects, the invention provides a method of increasing the lipid content of a cell comprising transforming a parent cell with a first nucleic acid and a second nucleic acid, wherein said first nucleic acid increases the activity of a native diacylglycerol acyltransferase or comprises a diacylglycerol acyltransferase gene and said second nucleic acid decreases the activity of a triacylglycerol lipase. Alternatively, the same nucleic acid could embody both elements described above. Thus, the invention also provides a method of increasing the lipid content of a cell comprising transforming a parent cell with a nucleic acid, wherein said nucleic acid decreases the activity of a triacylglycerol lipase in the cell, and said nucleic acid comprises a diacylglycerol acyltransferase gene or increases the activity of a native diacylglycerol acyltransferase.

Further, in some aspects, the invention provides a method of increasing the triacylglycerol content of a cell comprising: (a) providing a cell, comprising (i) a first genetic modification, wherein said first genetic modification increases the activity of a native diacylglycerol acyltransferase, or encodes at least one copy of a diacylglycerol acyltransferase gene native to the oleaginous cell or from a different species; and (ii) a second genetic modification that decreases the activity of a triacylglycerol lipase in the cell; (b) growing said cell under conditions whereby the first genetic modification is expressed, thereby producing a triacylglyccrol; and (c) optionally recovering the triacylglycerol.

One skilled in the art will readily appreciate that the present invention is well adapted to carry out the objects and obtain the ends and advantages mentioned, as well as those inherent therein. The embodiments described herein are not intended as limitations on the scope of the invention. These and other features, aspects, and advantages of the present invention will become better understood with reference to the following description, drawings, and claims.

DETAILED DESCRIPTION

Overview

Figure 1:
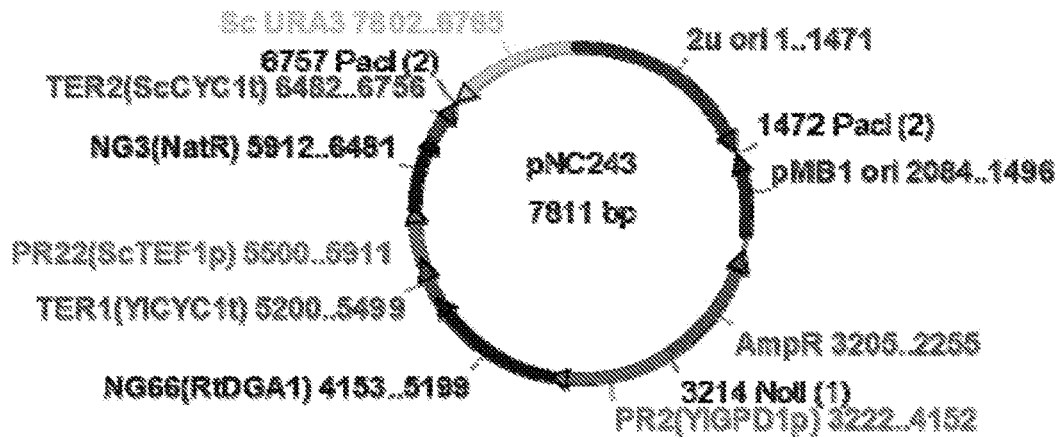
FIG. 1 shows a map of the pNC243 construct used to overexpress the diacylglycerol acyltransferase DGA1 gene NG66 in *Y. lipolytica* strain NS18 (obtained from ARS Culture Collection, NRRL#YB 392). Vector pNC243 was linearized by PacI/NotI restriction digest before transformation. "2u ori" denotes the *S. cerevisiae* origin of replication from the 2 μm circle plasmid; "pMB1 ori" denotes the *E. coli* pMB1 origin of replication from the pBR322 plasmid; "AmpR" denotes the bla gene used as a marker for selection with ampicillin; "PR2" denotes the *Y. lipolytica* GPD1 promoter-931 to -1; "NG66" denotes the native *Rhodosporidium toruloides* DGA1 cDNA synthesized by GenScript; "TER1" denotes the *Y. lipolytica* CYC1 terminator 300 base pairs after stop; "PR22" denotes the *S. cerevisiae* TEF1 promoter-412 to -1; "NG3" denotes the *Streptomyces noursei* Nat1 gene used as a marker for selection with nourseothricin; "TER2" denotes the *S. cerevisiae* CYC1 terminator 275 base pairs after stop; and "Sc URA3" denotes the *S. cerevisiae* URA3 auxotrophic marker for selection in yeast.

Disclosed are methods and compositions for creating transformed oleaginous cells with increased triacylglyccrol content. Disrupting the yeast triacylglycerol lipase gene TGL3 eliminates a pathway that depletes triacylglyccrol content. Additionally, overexpressing the diacylglycerol acyltransferase DGA1 increases the amount of protein that can synthesize triacylglyccrol. Therefore, combining DGA1 overexpression with a TGL3 deletion could be an attractive approach to further increase a cell's triacylglycerol content; however, the manipulation of proteins that affect a metabolic pathway is unpredictable at best. Cells that suppress the effects of a genetic modification frequently possess a selective advantage over those that acquire the desired trait. Thus, cells that display a desired phenotype are often difficult to engineer.

Disclosed is the successful combination of TGL3 deletion and DGA1 overexpression to increase a cell's triacylglycerol content. TGL3 deletion and the concomitant expression of the *R. toruloides* DGA1 diacylglycerol acyltransferase in *Y. lipolytica* strains resulted in a higher triacylglycerol content than strains carrying a single genetic modification.

Definitions

The articles "a" and "an" are used herein to refer to one or to more than one (i.e., to at least one) of the grammatical object of the article. By way of example, "an element" means one element or more than one element.

The term "activity," refers to the total capacity of a cell to perform a function. For example, a genetic modification that decreases the activity of a triacylglycerol lipase in a cell may reduce the amount of triacylglycerol lipase in a cell or reduce the efficiency of triacylglycerol lipase. A triacylglycerol lipase knockout reduces the amount of triacylglycerol lipase in the cell. Alternatively, a mutation to a triacylglycerol lipase gene may reduce the efficiency of its triacylglycerol lipase protein product with little effect on the amount of cellular triacylglycerol lipase. Mutations that reduce the efficiency of triacylglycerol lipase may affect the active site, for example, by changing one or more active site residues; they may impair the enzyme's kinetics, for example, by sterically blocking substrates or products; they may affect protein folding or dynamics, for example, by reducing the proportion of properly-folded enzymes; they may affect protein localization, for example, by preventing the lipase from localizing to lipid particles; or they may affect protein degradation, for example, by adding one or more protein cleavage sites or by adding one or more residues or amino acid sequences that target the protein for proteolysis. These mutations affect coding regions. Mutations that decrease triacylglycerol lipase activity may instead affect the transcription or translation of the gene. For example, mutation to a triacylglycerol lipase enhancer or promoter can reduce triacylglyccrol lipase activity by reducing its expression. Mutating or deleting the non-coding portions of a triacylglycerol lipase gene, such as its introns, may also reduce transcription or translation. Additionally, mutations to the upstream regulators of a triacylglycerol lipase may affect triacylglycerol lipase activity; for example, the over-expression of one or more repressors may decrease triacylglycerol lipase activity, and a knockout or mutation of one or more activators may similarly decrease triacylglycerol lipase activity. A genetic modification that increases the activity of a diacylglycerol acyltransferase in a cell may increase the amount of triacylglycerol acyltransferase in a cell or increase the efficiency of diacylglycerol acyltransferase. For example, the genetic modification may simply insert an additional copy of diacylglycerol acyltransferase into the cell such that the additional copy is transcribed and translated into additional functional diacylglycerol acyltransferase. The added diacylglycerol acyltransferase gene can be native to the host organism or from a different organism. Alternatively, mutating or deleting the non-coding portions of a native diacylglycerol acyltransferase gene, such as its introns, may also increase translation. A native diacylglycerol acyltransferase gene can be altered by adding a new promoter that causes more transcription. Similarly, enhancers may be added to the diacylglycerol acyltransferase gene that increase transcription, or silencers may be mutated or deleted from the diacylglycerol acyltransferase gene to increase transcription. Mutations to a native gene's coding region might also increase diacylglycerol acyltransferase activity, for example, by producing a protein variant that does not interact with inhibitory proteins or molecules. The over-expression of one or more activators may increase diacylglycerol acyltransferase activity by increasing the expression of a diacylglycerol acyltransferase protein, and a knockout or mutation of one or more repressors may similarly increase diacylglycerol acyltransferase activity.

The term "biologically-active portion" refers to an amino acid sequence that is less than a full-length amino acid sequence, but exhibits at least one activity of the full length sequence. For example, a biologically-active portion of a diacylglycerol acyltransferase may refer to one or more domains of DGA1 or DGA2 having biological activity for converting acyl-CoA and diacylglycerol to triacylglycerol. Biologically-active portions of a DGA1 include peptides or polypeptides comprising amino acid sequences sufficiently identical to or derived from the amino acid sequence of the DGA1 protein, e.g., the amino acid sequence as set forth in SEQ ID NOs: 1, 3, 5, 7, 9, 11, 13, 15, 17, 41, 43, 45, 47, 49, 51, 53, 55, 57, 59, or 61 which include fewer amino acids than the full length DGA1, and exhibit at least one activity of a DGA1 protein. Similarly, biologically-active portions of a DGA2 protein include peptides or polypeptides comprising amino acid sequences sufficiently identical to or derived from the amino acid sequence of the DGA2 protein, e.g., the amino acid sequence as set forth in SEQ ID NOs: 29, 31, 33, 35, 37, 39, 63, 65, 67, 69, 71, 73, or 75, which include fewer amino acids than the full length DGA2, and exhibit at least one activity of a DGA2 protein. Biologically-active portions of a DGA3 protein include peptides or polypeptides comprising amino acid sequences sufficiently identical to or derived from the amino acid sequence of the DGA3 protein, e.g., the amino acid sequence as set forth in SEQ ID NOs: 83 or 85, which include fewer amino acids than the full length DGA3, and exhibit at least one activity of a DGA3 protein. A biologically-active portion of a diacylglycerol acyltransferase may comprise, for example, 100, 101, 112, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, or 696 amino acids. Typically, biologically active portions comprise a domain or motif having the catalytic activity of converting acyl-CoA and diacylglycerol to triacylglycerol. A biologically active portion of a DGA1 protein can be a polypeptide which is, for example, 278 amino acids in length.

The term "DGAT1" refers to a gene that encodes a type 1 diacylglycerol acyltransferase protein, such as a gene that encodes a DGA2 protein.

The term "DGAT2" refers to a gene that encodes a type 2 diacylglycerol acyltransferase protein, such as a gene that encodes a DGA1 protein.

The term "DGAT3" refers to a gene that encodes a type 2 diacylglycerol acyltransferase protein, such as a gene that encodes a DGA3 protein.

"Diacylglyceride," "diacylglycerol," and "diglyceride," are esters comprised of glycerol and two fatty acids.

The terms "diacylglycerol acyltransferase" and "DGA" refer to any protein that catalyzes the formation of triacylglycerides from diacylglycerol. Diacylglycerol acyltransferases include type 1 diacylglycerol acyltransferases (DGA2), type 2 diacylglycerol acyltransferases (DGA1), and all homologs that catalyze the above-mentioned reaction.

The terms "diacylglycerol acyltransferase type 1" and "type 1 diacylglycerol acyltransferases" refer to DGA2 and DGA2 orthologs.

The terms "diacylglycerol acyltransferase, type 2" and "type 2 diacylglycerol acyltransferases" refer to DGA1 and DGA1 orthologs.

The terms "diacylglycerol acyltransferase, type 3" and "type 3 diacylglycerol acyltransferases" refer to DGA3 and DGA3 orthologs.

The term "domain" refers to a part of the amino acid sequence of a protein that is able to fold into a stable three-dimensional structure independent of the rest of the protein.

The term "drug" refers to any molecule that inhibits cell growth or proliferation, thereby providing a selective advantage to cells that contain a gene that confers resistance to the drug. Drugs include antibiotics, antimicrobials, toxins, and pesticides.

"Dry weight" and "dry cell weight" mean weight determined in the relative absence of water. For example, reference to oleaginous cells as comprising a specified percentage of a particular component by dry weight means that the percentage is calculated based on the weight of the cell after substantially all water has been removed.

The term "encode" refers to nucleic acids that comprise a coding region, portion of a coding region, or compliments thereof. Both DNA and RNA may encode a gene. Both DNA and RNA may encode a protein.

The term "exogenous" refers to anything that is introduced into a cell. An "exogenous nucleic acid" is a nucleic acid that entered a cell through the cell membrane. An exogenous nucleic acid may contain a nucleotide sequence that exists in the native genome of a cell and/or nucleotide sequences that did not previously exist in the cell's genome. Exogenous nucleic acids include exogenous genes. An "exogenous gene" is a nucleic acid that codes for the expression of an RNA and/or protein that has been introduced into a cell (e.g., by transformation/transfection), and is also referred to as a "transgene." A cell comprising an exogenous gene may be referred to as a recombinant cell, into which additional exogenous gene(s) may be introduced. The exogenous gene may be from the same or different species relative to the cell being transformed. Thus, an exogenous gene can include a native gene that occupies a different location in the genome of the cell or is under different control, relative to the endogenous copy of the gene. An exogenous gene may be present in more than one copy in the cell. An exogenous gene may be maintained in a cell as an insertion into the genome (nuclear or plastid) or as an episomal molecule.

The term "expression" refers to the amount of a nucleic acid or amino acid sequence (e.g., peptide, polypeptide, or protein) in a cell. The increased expression of a gene refers to the increased transcription of that gene. The increased expression of an amino acid sequence, peptide, polypeptide, or protein refers to the increased translation of a nucleic acid encoding the amino acid sequence, peptide, polypeptide, or protein.

The term "gene," as used herein, may encompass genomic sequences that contain exons, particularly polynucleotide sequences encoding polypeptide sequences involved in a specific activity. The term further encompasses synthetic nucleic acids that did not derive from genomic sequence. In certain embodiments, the genes lack introns, as they are synthesized based on the known DNA sequence of cDNA and protein sequence. In other embodiments, the genes are synthesized, non-native cDNA wherein the codons have been optimized for expression in *Y. lipolytica* based on codon usage. The term can further include nucleic acid molecules comprising upstream, downstream, and/or intron nucleotide sequences.

The term "genetic modification" refers to the result of a transformation. Every transformation causes a genetic modification by definition.

The term "homolog", as used herein, refers to (a) peptides, oligopeptides, polypeptides, proteins, and enzymes having amino acid substitutions, deletions and/or insertions relative to the unmodified protein in question and having similar biological and functional activity as the unmodified protein from which they are derived, and (b) nucleic acids which encode peptides, oligopeptides, polypeptides, proteins, and enzymes with the same characteristics described in (a).

"Inducible promoter" is a promoter that mediates the transcription of an operably linked gene in response to a particular stimulus.

The term "integrated" refers to a nucleic acid that is maintained in a cell as an insertion into the cell's genome, such as insertion into a chromosome, including insertions into a plastid genome.

"In operable linkage" refers to a functional linkage between two nucleic acid sequences, such a control sequence (typically a promoter) and the linked sequence (typically a sequence that encodes a protein, also called a coding sequence). A promoter is in operable linkage with a gene if it can mediate transcription of the gene.

The term "knockout mutation" or "knockout" refers to a genetic modification that prevents a native gene from being transcribed and translated into a functional protein.

The term "native" refers to the composition of a cell or parent cell prior to a transformation event. A "native gene" refers to a nucleotide sequence that encodes a protein that has not been introduced into a cell by a transformation event. A "native protein" refers to an amino acid sequence that is encoded by a native gene.

The terms "nucleic acid" refers to a polymeric form of nucleotides of any length, either deoxyribonucleotides or ribonucleotides, or analogs thereof. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. In all nucleic acid sequences provided herein, U nucleotides are interchangeable with T nucleotides.

The term "parent cell" refers to every cell from which a cell descended. The genome of a cell is comprised of the parent cell's genome and any subsequent genetic modifications to the parent cell's genome.

As used herein, the term "plasmid" refers to a circular DNA molecule that is physically separate from an organism's genomic DNA. Plasmids may be linearized before being introduced into a host cell (referred to herein as a linearized plasmid). Linearized plasmids may not be self-replicating, but may integrate into and be replicated with the genomic DNA of an organism.

The term "portion" refers to peptides, oligopeptides, polypeptides, protein domains, and proteins. A nucleotide sequence encoding a "portion of a protein" includes both nucleotide sequences that can be transcribed and/or translated and nucleotide sequences that must undergo one or more recombination events to be transcribed and/or translated. For example, a nucleic acid may comprise a nucleotide sequence encoding one or more amino acids of a selectable marker protein. This nucleic acid can be engineered to recombine with one or more different nucleotide sequences that encode the remaining portion of the protein. Such nucleic acids are useful for generating knockout mutations because only recombination with the target sequence is likely to reconstitute the full-length selectable marker gene whereas random-integration events are unlikely to result in a nucleotide sequence that can produce a functional marker protein. A "biologically-active portion" of a polypeptide is any amino acid sequence found in the polypeptide's amino acid sequence that is less than the full amino acid sequence but can perform the same function as the full-length polypeptide. A biologically-active portion of a diacylglycerol acyltransferase includes any amino acid sequence found in a full-length diacylglycerol acyltransferase that can catalyze the formation of triacylglycerol from diacylglycerol and acyl-CoA. A biologically-active portion of a polypeptide includes portions of the polypeptide that have the same activity as the full-length peptide and every portion that has more activity than background. For example, a biologically-active portion of a diacylglycerol acyltransferase may have 0.1, 0.5, 1, 2, 3, 4, 5, 10, 25, 30, 35, 40, 45, 50, 55, 60, 65, 70, 75, 80, 85, 86, 87, 88, 89, 90, 91, 92, 93, 94, 95, 96, 97, 98, 99, 99.5, 99.6, 99.7, 99.8, 99.9, 100, 100.1, 100.2, 100.3, 100.4, 100.5, 100.6, 100.7, 100.8, 100.9, 101, 105, 110, 115, 120, 125, 130, 135, 140, 145, 150, 160, 170, 180, 190, 200, 220, 240, 260, 280, 300, 320, 340, 360, 380, 400 percent activity relative to the full-length polypeptide or higher. A biologically-active portion of a polypeptide may include portions of a peptide that lack a domain that targets the polypeptide to a cellular compartment.

A "promoter" is a nucleic acid control sequence that directs the transcription of a nucleic acid. As used herein, a promoter includes the necessary nucleic acid sequences near the start site of transcription. A promoter also optionally includes distal enhancer or repressor elements, which can be located as much as several thousand base pairs from the start site of transcription.

"Recombinant" refers to a cell, nucleic acid, protein, or vector, which has been modified due to the introduction of an exogenous nucleic acid or the alteration of a native nucleic acid. Thus, e.g., recombinant cells can express genes that are not found within the native (non-recombinant) form of the cell or express native genes differently than those genes are expressed by a non-recombinant cell. Recombinant cells can, without limitation, include recombinant nucleic acids that encode for a gene product or for suppression elements such as mutations, knockouts, antisense, interfering RNA (RNAi), or dsRNA that reduce the levels of active gene product in a cell. A "recombinant nucleic acid" is a nucleic acid originally formed in vitro, in general, by the manipulation of nucleic acid, e.g., using polymerases, ligases, exonucleases, and endonucleases, or otherwise is in a form not normally found in nature. Recombinant nucleic acids may be produced, for example, to place two or more nucleic acids in operable linkage. Thus, an isolated nucleic acid or an expression vector formed in vitro by ligating DNA molecules that are not normally joined in nature, are both considered recombinant for the purposes of this invention. Once a recombinant nucleic acid is made and introduced into a host cell or organism, it may replicate using the in vivo cellular machinery of the host cell; however, such nucleic acids, once produced recombinantly, although subsequently replicated intracellularly, are still considered recombinant for purposes of this invention. Similarly, a "recombinant protein" is a protein made using recombinant techniques, i.e., through the expression of a recombinant nucleic acid. The term "regulatory region" refers to nucleotide sequences that affect the transcription or translation of a gene but do not encode an amino acid sequence. Regulatory regions include promoters, operators, enhancers, and silencers.

"Transformation" refers to the transfer of a nucleic acid into a host organism or the genome of a host organism, resulting in genetically stable inheritance. Host organisms containing the transformed nucleic acid fragments are referred to as "recombinant", "transgenic" or "transformed" organisms. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. Typically, expression vectors include, for example, one or more cloned genes under the transcriptional control of 5' and 3' regulatory sequences and a selectable marker. Such vectors also can contain a promoter regulatory region (e.g., a regulatory region controlling inducible or constitutive, environmentally- or developmentally-regulated, or location-specific expression), a transcription initiation start site, a ribosome binding site, a transcription termination site, and/or a polyadenylation signal.

The term "transformed cell" refers to a cell that has undergone a transformation. Thus, a transformed cell comprises the parent's genome and an inheritable genetic modification.

The terms "triacylglyceride" "triacylglycerol," "triglyceride," and "TAG" are esters comprised of glycerol and three fatty acids.

The term "triacylglycerol lipase" refers to any protein that can catalyze the removal of a fatty acid chain from a triacylglycerol. Triacylglycerol lipases include TGL3, TLG3/4, and TGL4.

The term "vector" refers to the means by which a nucleic acid can be propagated and/or transferred between organisms, cells, or cellular components. Vectors include plasmids, linear DNA fragments, viruses, bacteriophage, proviruses, phagemids, transposons, and artificial chromosomes, and the like, that may or may not be able to replicate autonomously or integrate into a chromosome of a host cell.

Microbe Engineering

A. Overview

In certain embodiments of the invention, a microorganism is genetically modified to increase its triacylglycerol content.

Genes and gene products may be introduced into microbial host cells. Suitable host cells for expression of the genes and nucleic acid molecules are microbial hosts that can be found broadly within the fungal or bacterial families. Examples of suitable host strains include but are not limited to fungal or yeast species, such as *Arxula, Aspergillus, Aurantiochytrium, Candida, Claviceps, Cryptococcus, Cunninghamella, Hansenula, Kluyveromyces, Leucosporidiella, Lipomyces, Mortierella, Ogataea, Pichia, Prototheca, Rhizopus, Rhodosporidium, Rhodotorula, Saccharomyces, Schizosaccharomyces, Tremella, Trichosporon, Yarrowia*, or bacterial species, such as members of proteobacteria and actinomycetes, as well as the genera *Acinetobacter, Arthrobacter, Brevibacterium, Acidovorax, Bacillus, Clostridia, Streptomyces, Escherichia, Salmonella, Pseudomonas*, and *Cornyebacterium. Yarrowia lipolytica* and *Arxula adeninivorans* are suited for use as a host microorganism because they can accumulate a large percentage of their weight as triacylglycerols.

Microbial expression systems and expression vectors containing regulatory sequences that direct high level expression of foreign proteins are known to those skilled in the art. Any of these could be used to construct chimeric genes to produce any one of the gene products of the instant sequences. These chimeric genes could then be introduced into appropriate microorganisms via transformation techniques to provide high-level expression of the enzymes.

For example, a gene encoding an enzyme can be cloned in a suitable plasmid, and an aforementioned starting parent strain as a host can be transformed with the resulting plasmid. This approach can increase the copy number of each of the genes encoding the enzymes and, as a result, the activities of the enzymes can be increased. The plasmid is not particularly limited so long as it renders a desired genetic modification inheritable to the microorganism's progeny.

Vectors or cassettes useful for the transformation of suitable host cells are well known in the art. Typically the vector or cassette contains sequences that direct the transcription and translation of the relevant gene, a selectable marker, and sequences that allow autonomous replication or chromosomal integration. Suitable vectors comprise a region 5' of the gene harboring transcriptional initiation controls and a region 3' of the DNA fragment which controls transcriptional termination. It is preferred when both control regions are derived from genes homologous to the transformed host cell, although it is to be understood that such control regions need not be derived from the genes native to the specific species chosen as a production host.

Promoters, cDNAs, and 3'UTRs, as well as other elements of the vectors, can be generated through cloning techniques using fragments isolated from native sources (Green & Sambrook, *Molecular Cloning: A Laboratory Manual*, (4th ed., 2012); U.S. Pat. No. 4,683,202; incorporated by reference). Alternatively, elements can be generated synthetically using known methods (Gene 164:49-53 (1995)).

B. Homologous Recombination

Homologous recombination is the ability of complementary DNA sequences to align and exchange regions of homology. Transgenic DNA ("donor") containing sequences homologous to the genomic sequences being targeted ("template") is introduced into the organism and then undergoes recombination into the genome at the site of the corresponding homologous genomic sequences.

The ability to carry out homologous recombination in a host organism has many practical implications for what can be carried out at the molecular genetic level and is useful in the generation of a microbe that can produce a desired product. By its nature, homologous recombination is a precise gene targeting event and, hence, most transgenic lines generated with the same targeting sequence will be essentially identical in terms of phenotype, necessitating the screening of far fewer transformation events. Homologous recombination also targets gene insertion events into the host chromosome, potentially resulting in excellent genetic stability, even in the absence of genetic selection. Because different chromosomal loci will likely impact gene expression, even from exogenous promoters/UTRs, homologous recombination can be a method of querying loci in an unfamiliar genome environment and to assess the impact of these environments on gene expression.

A particularly useful genetic engineering approach using homologous recombination is to co-opt specific host regulatory elements such as promoters/UTRs to drive heterologous gene expression in a highly specific fashion.

Because homologous recombination is a precise gene targeting event, it can be used to precisely modify any nucleotide(s) within a gene or region of interest, so long as sufficient flanking regions have been identified. Therefore, homologous recombination can be used as a means to modify regulatory sequences impacting gene expression of RNA and/or proteins. It can also be used to modify protein coding regions in an effort to modify enzyme activities such as substrate specificity, affinities and Km, thereby affecting a desired change in the metabolism of the host cell. Homologous recombination provides a powerful means to manipulate the host genome resulting in gene targeting, gene conversion, gene deletion, gene duplication, gene inversion and exchanging gene expression regulatory elements such as promoters, enhancers and 3'UTRs.

Homologous recombination can be achieved by using targeting constructs containing pieces of endogenous sequences to "target" the gene or region of interest within the endogenous host cell genome. Such targeting sequences can either be located 5' of the gene or region of interest, 3' of the gene/region of interest or even flank the gene/region of interest. Such targeting constructs can be transformed into the host cell either as a supercoiled plasmid DNA with additional vector backbone, a PCR product with no vector backbone, or as a linearized molecule. In some cases, it may be advantageous to first expose the homologous sequences within the transgenic DNA (donor DNA) by cutting the transgenic DNA with a restriction enzyme. This step can increase the recombination efficiency and decrease the occurrence of undesired events. Other methods of increasing recombination efficiency include using PCR to generate transforming transgenic DNA containing linear ends homologous to the genomic sequences being targeted.

C. Vectors and Vector Components

Vectors for transforming microorganisms in accordance with the present invention can be prepared by known techniques familiar to those skilled in the art in view of the disclosure herein. A vector typically contains one or more genes, in which each gene codes for the expression of a desired product (the gene product) and is operably linked to one or more control sequences that regulate gene expression or target the gene product to a particular location in the recombinant cell.

1. Control Sequences

Control sequences are nucleic acids that regulate the expression of a coding sequence or direct a gene product to a particular location in or outside a cell. Control sequences that regulate expression include, for example, promoters that regulate transcription of a coding sequence and terminators that terminate transcription of a coding sequence. Another control sequence is a 3' untranslated sequence located at the end of a coding sequence that encodes a polyadenylation signal. Control sequences that direct gene products to particular locations include those that encode signal peptides, which direct the protein to which they are attached to a particular location inside or outside the cell.

Thus, an exemplary vector design for expression of a gene in a microbe contains a coding sequence for a desired gene product (for example, a selectable marker, or an enzyme) in operable linkage with a promoter active in yeast. Alternatively, if the vector does not contain a promoter in operable linkage with the coding sequence of interest, the coding sequence can be transformed into the cells such that it becomes operably linked to an endogenous promoter at the point of vector integration.

The promoter used to express a gene can be the promoter naturally linked to that gene or a different promoter.

A promoter can generally be characterized as constitutive or inducible. Constitutive promoters are generally active or function to drive expression at all times (or at certain times in the cell life cycle) at the same level. Inducible promoters, conversely, are active (or rendered inactive) or are significantly up- or down-regulated only in response to a stimulus. Both types of promoters find application in the methods of the invention. Inducible promoters useful in the invention include those that mediate transcription of an operably linked gene in response to a stimulus, such as an exogenously provided small molecule, temperature (heat or cold), lack of nitrogen in culture media, etc. Suitable promoters can activate transcription of an essentially silent gene or upregulate, preferably substantially, transcription of an operably linked gene that is transcribed at a low level.

Inclusion of termination region control sequence is optional, and if employed, then the choice is primarily one of convenience, as the termination region is relatively interchangeable. The termination region may be native to the transcriptional initiation region (the promoter), may be native to the DNA sequence of interest, or may be obtainable from another source (See, e.g., Chen & Orozco, Nucleic Acids Research 16:8411 (1988)).

2. Genes and Codon Optimization

Typically, a gene includes a promoter, a coding sequence, and termination control sequences. When assembled by recombinant DNA technology, a gene may be termed an expression cassette and may be flanked by restriction sites for convenient insertion into a vector that is used to introduce the recombinant gene into a host cell. The expression cassette can be flanked by DNA sequences from the genome or other nucleic acid target to facilitate stable integration of the expression cassette into the genome by homologous recombination. Alternatively, the vector and its expression cassette may remain unintegrated (e.g., an episome), in which case, the vector typically includes an origin of replication, which is capable of providing for replication of the vector DNA.

A common gene present on a vector is a gene that codes for a protein, the expression of which allows the recombinant cell containing the protein to be differentiated from cells that do not express the protein. Such a gene, and its corresponding gene product, is called a selectable marker or selection marker. Any of a wide variety of selectable markers can be employed in a transgene construct useful for transforming the organisms of the invention.

For optimal expression of a recombinant protein, it is beneficial to employ coding sequences that produce mRNA with codons optimally used by the host cell to be transformed. Thus, proper expression of transgenes can require that the codon usage of the transgene matches the specific codon bias of the organism in which the transgene is being expressed. The precise mechanisms underlying this effect are many, but include the proper balancing of available aminoacylated tRNA pools with proteins being synthesized in the cell, coupled with more efficient translation of the transgenic messenger RNA (mRNA) when this need is met. When codon usage in the transgene is not optimized, available tRNA pools are not sufficient to allow for efficient translation of the transgenic mRNA resulting in ribosomal stalling and termination and possible instability of the transgenic mRNA.

D. Transformation

Cells can be transformed by any suitable technique including, e.g., biolistics, electroporation, glass bead transformation, and silicon carbide whisker transformation. Any convenient technique for introducing a transgene into a microorganism can be employed in the present invention. Transformation can be achieved by, for example, the method of D. M. Morrison (Methods in Enzymology 68:326 (1979)), the method by increasing permeability of recipient cells for DNA with calcium chloride (Mandel & Higa, J. Molecular Biology, 53:159 (1970)), or the like.

Examples of expression of transgenes in oleaginous yeast (e.g., *Yarrowia lipolytica*) can be found in the literature (Bordes et al., J. Microbiological Methods, 70:493 (2007); Chen et al., Applied Microbiology & Biotechnology 48:232 (1997)). Examples of expression of exogenous genes in bacteria such as *E. coli* are well known (Green & Sambrook, *Molecular Cloning: A Laboratory Manual*, (4th ed., 2012)).

Vectors for transformation of microorganisms in accordance with the present invention can be prepared by known techniques familiar to those skilled in the art. In one embodiment, an exemplary vector design for expression of a gene in a microorganism contains a gene encoding an enzyme in operable linkage with a promoter active in the microorganism. Alternatively, if the vector does not contain a promoter in operable linkage with the gene of interest, the gene can be transformed into the cells such that it becomes operably linked to a native promoter at the point of vector integration. The vector can also contain a second gene that encodes a protein. Optionally, one or both gene(s) is/are followed by a 3' untranslated sequence containing a polyadenylation signal. Expression cassettes encoding the two genes can be physically linked in the vector or on separate vectors. Co-transformation of microbes can also be used, in which distinct vector molecules are simultaneously used to transform cells (Protist 155:381-93 (2004)). The transformed cells can be optionally selected based upon the ability to grow in the presence of the antibiotic or other selectable marker under conditions in which cells lacking the resistance cassette would not grow.

Exemplary Nucleic Acids, Cells, and Methods

A. Diacylglycerol Acyltransferase Nucleic Acid Molecules and Vectors

The diacylglycerol acyltransferase may be a type 1 diacylglycerol acyltransferase, type 2 diacylglycerol acyltransferase, type 3 diacylglycerol acyltransferase, or any other protein that catalyzes the conversion of diacylglycerol into a triacylglyceride. In some embodiments, the diacylglycerol acyltransferase is DGA1. For example, the diacylglycerol acyltransferase may be a DGA1 protein encoded by a DGAT2 gene selected from the group consisting of *Arxula adeninivorans, Aspergillus terreus, Aurantiochytrium limacinum, Claviceps purpurea, Gloeophyllum trabeum, Lipomyces starkeyi, Microbotryum violaceum, Pichia guilliermondii, Phaeodactylum tricornutum, Puccinia graminis, Rhodosporidium diobovatum, Rhodosporidium toruloides, Rhodotorula graminis*, and *Yarrowia lipolytica*.

The DGAT72 gene may have a nucleotide sequence set forth in SEQ ID NO: 2, 4, 6, 8, 10, 12, 14, 16, 18, 42, 44, 46, 48, 50, 52, 54, 56, 58, 60, or 62. In other embodiments, the DGAT12 gene is substantially identical to SEQ ID NO: 2, 4, 6, 8, 10, 12, 14, 16, 18, 42, 44, 46, 48, 50, 52, 54, 56, 58, 60, or 62, and the nucleotide sequence encodes a protein that retains the functional activity of a protein encoded by SEQ ID NO: 2, 4, 6, 8, 10, 12, 14, 16, 18, 42, 44, 46, 48, 50, 52, 54, 56, 58, 60, or 62, yet differs in nucleotide sequence due to natural allelic variation or mutagenesis. In another embodiment, the DGAT2 gene comprises an nucleotide sequence at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97/%, 98%99%, 99.1%, 99.2%, 99.3%, 99.4%, 99.5%, 99.6%, 99.7%, 99.8%, 99.9% or more identical to SEQ ID NO: 2, 4, 6, 8, 10, 12, 14, 16, 18, 42, 44, 46, 48, 50, 52, 54, 56, 58, 60, or 62.

The DGA1 may have an amino acid sequence set forth in SEQ ID NO: 1, 3, 5, 7, 9, 11, 13, 15, 17, 41, 43, 45, 47, 49, 51, 53, 55, 57, 59, or 61. In other embodiments, the DGA1 is substantially identical to SEQ ID NO: 1, 3, 5, 7, 9, 11, 13, 15, 17, 41, 43, 45, 47, 49, 51, 53, 55, 57, 59, or 61, and retains the functional activity of the protein of SEQ ID NO: 1, 3, 5, 7, 9, 11, 13, 15, 17, 41, 43, 45, 47, 49, 51, 53, 55, 57, 59, or 61, yet differs in amino acid sequence due to natural allelic variation or mutagenesis. In another embodiment, the DGA1 protein comprises an amino acid sequence at least about 80%, 81%, 82%, 83%, 84%, 85%, 86%, 87%, 88%, 89%, 90%, 91%, 92%, 93%, 94%, 95%, 96%, 97%, 98%, 99% 99.1%, 99.2%, 99.3%, 99.4%, 99.5%, 99.6%, 99.7%, 99.8% 99.9% or more identical to SEQ ID NO: 1, 3, 5, 7, 9, 11, 13, 15, 17, 41, 43, 45, 47, 49, 51, 53, 55, 57, 59, or 61.

In some embodiments, the diacylglycerol acyltransferase is DGA2. For example, the diacylglycerol acyltransferase may be a DGA2 protein encoded by a DGAT1 gene found in an organism selected from the group consisting of *Arxula adeninivorans, Aspergillus terreus, Chaetomium globosum, Claviceps purpurea, Lipomyces starkeyi, Metarhizium acridum, Ophiocordyceps sinensis, Phaeodactylum tricornutum, Pichia guilliermondii, Rhodosporidium toruloides, Rhodotorula graminis, Trichoderma virens,* and *Yarrowia lipolytica.*

The DGAT1 gene may have a nucleotide sequence set forth in SEQ ID NO: 30, 32, 34, 36, 38, 40, 64, 66, 68, 70, 72, 74, or 76. In other embodiments, the DGAT1 gene is substantially identical to SEQ ID NO: 30, 32, 34, 36, 38, 40, 64, 66, 68, 70, 72, 74, or 76, and the nucleotide sequence encodes a protein that retains the functional activity of a protein encoded by SEQ ID NO: 30, 32, 34, 36, 38, 40, 64, 66, 68, 70, 72, 74, or 76, yet differs in nucleotide sequence due to natural allelic variation or mutagenesis. In another embodiment, the DGAT1 gene comprises an nucleotide sequence at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to SEQ ID NO: 30, 32, 34, 36, 38, 40, 64, 66, 68, 70, 72, 74, or 76.

The DGA2 may have an amino acid sequence set forth in SEQ ID NO: 29, 31, 33, 35, 37, 39, 63, 65, 67, 69, 71, 73, or 75. In other embodiments, the DGA2 is substantially identical to SEQ ID NO: 29, 31, 33, 35, 37, 39, 63, 65, 67, 69, 71, 73, or 75, and retains the functional activity of the protein of SEQ ID NO: 29, 31, 33, 35, 37, 39, 63, 65, 67, 69, 71, 73, or 75, yet differs in amino acid sequence due to natural allelic variation or mutagenesis. In another embodiment, the DGA2 protein comprises an amino acid sequence at least about 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to SEQ ID NO: 29, 31, 33, 35, 37, 39, 63, 65, 67, 69, 71, 73, or 75.

In some embodiments, the diacylglycerol acyltransferase is DGA3. For example, the diacylglycerol acyltransferase may be a DGA3 protein encoded by a DGA3 gene found in an organism selected from the group consisting of *Ricinus communis* and *Arachis hypogaea.*

The DGAT3 gene may have a nucleotide sequence set forth in SEQ ID NO: 84 or 86. In other embodiments, the DGAT3 gene is substantially identical to SEQ ID NO: 84 or 86, and the nucleotide sequence encodes a protein that retains the functional activity of a protein encoded by SEQ ID NO: 84 or 86, yet differs in nucleotide sequence due to natural allelic variation or mutagenesis. In another embodiment, the DGAT3 gene comprises an nucleotide sequence at least about 70%, 71%, 72%, 73%, 74%, 75%, 76%, 77%, 78%, 79%, 80%, 81%, 82%, 83%, 84%, 850% 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to SEQ ID NO: 84 or 86.

The DGA3 may have an amino acid sequence set forth in SEQ ID NO: 83 or 85. In other embodiments, the DGA3 is substantially identical to SEQ ID NO: 83 or 85, and retains the functional activity of the protein of SEQ ID NO: 83 or 85, yet differs in amino acid sequence due to natural allelic variation or mutagenesis. In another embodiment, the DGA3 protein comprises an amino acid sequence at least about 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to SEQ ID NO: 83 or 85.

The DGAT1, DGAT2, and DGAT3 genes may comprise conservative substitutions, deletions, and/or insertions while still encoding a protein that has functional diacylglycerol acyltransferase activity. For example, the DGAT1, DGAT2, or DGAT3 codons may be optimized for a particular host cell, different codons may be substituted for convenience, such as to introduce a restriction site or to create optimal PCR primers, or codons may be substituted for another purpose. Similarly, the nucleotide sequence may be altered to create conservative amino acid substitutions, deletions, and/or insertions.

The DGA1, DGA2, and DGA3 polypeptides may comprise conservative substitutions, deletions, and/or insertions while still maintaining functional diacylglycerol acyltransferase activity. Conservative substitution tables are well known in the art (Creighton, *Proteins* (2d. ed., 1992)).

Amino acid substitutions, deletions and/or insertions may readily be made using recombinant DNA manipulation techniques. Methods for the manipulation of DNA sequences to produce substitution, insertion or deletion variants of a protein are well known in the art. These methods include M13 mutagenesis, T7-Gen in vitro mutagenesis (USB, Cleveland, Ohio), Quick Change Site Directed mutagenesis (Stratagene, San Diego, Calif.), PCR-mediated site-directed mutagenesis, and other site-directed mutagenesis protocols.

To determine the percent identity of two amino acid sequences or of two nucleic acid sequences, the sequences can be aligned for optimal comparison purposes (e.g., gaps can be introduced in one or both of a first and a second amino acid or nucleic acid sequence for optimal alignment and non-identical sequences can be disregarded for comparison purposes). The length of a reference sequence aligned for comparison purposes can be at least 95% of the length of the reference sequence. The amino acid residues or nucleotides at corresponding amino acid positions or nucleotide positions can then be compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In one embodiment, the percent identity between two amino acid sequences can be determined using the Needleman and Wunsch (J. Molecular Biology 48:444-453 (1970)) algorithm which has been incorporated into the GAP program in the GCG software package (available at http://www.gcg.com), using either a Blosum 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences can be determined using the algorithm of E. Meyers and W. Miller (Computer Applications in the Biosciences 4:11-17 (1988)) which has been incorporated into the ALIGN program (version 2.0 or 2.0 U), using a PAM120 weight residue table, a gap length penalty of 12 and a gap penalty of 4.

Exemplary computer programs which can be used to determine identity between two sequences include, but are not limited to, the suite of BLAST programs, e.g., BLASTN, MEGABLAST, BLASTX, TBLASTN. TBLASTX, and BLASTP, and Clustal programs. e.g., ClustalW, ClustalX, and Clustal Omega.

Sequence searches are typically carried out using the BLASTN program, when evaluating a given nucleic acid sequence relative to nucleic acid sequences in the GenBank DNA Sequences and other public databases. The BLASTX program is effective for searching nucleic acid sequences that have been translated in all reading frames against amino acid sequences in the GenBank Protein Sequences and other public databases.

An alignment of selected sequences in order to determine "% identity" between two or more sequences is performed using for example, the CLUSTAL-W program.

A "coding sequence" or "coding region" refers to a nucleic acid molecule having sequence information necessary to produce a protein product, such as an amino acid or polypeptide, when the sequence is expressed. The coding sequence may comprise and/or consist of untranslated sequences (including introns or 5' or 3' untranslated regions) within translated regions, or may lack such intervening untranslated sequences (e.g., as in cDNA).

The abbreviation used throughout the specification to refer to nucleic acids comprising and/or consisting of nucleotide sequences are the conventional one-letter abbreviations. Thus when included in a nucleic acid, the naturally occurring encoding nucleotides are abbreviated as follows: adenine (A), guanine (G), cytosine (C), thymine (T) and uracil (U). Also, unless otherwise specified, the nucleic acid sequences presented herein is the 5'→3' direction.

As used herein, the term "complementary" and derivatives thereof are used in reference to pairing of nucleic acids by the well-known rules that A pairs with T or U and C pairs with G. Complement can be "partial" or "complete". In partial complement, only some of the nucleic acid bases are matched according to the base pairing rules; while in complete or total complement, all the bases are matched according to the pairing rule. The degree of complement between the nucleic acid strands may have significant effects on the efficiency and strength of hybridization between nucleic acid strands as well known in the art. The efficiency and strength of said hybridization depends upon the detection method.

As used herein, "DGA1" means a diacylglycerol acyltransferase type 2 (DGAT2). DGA1 is an integral membrane protein that catalyzes the final enzymatic step in oil biosynthesis and the production of triacylglycerols in plants, fungi, and mammals. The DGA1 may play a key role in altering the quantity of long-chain polyunsaturated fatty acids produced in oils of oleaginous organisms. DGA1 is related to the acyl-coenzyme A:cholesterol acyltransferase ("ACAT"). This enzyme is responsible for transferring an acyl group from acyl-coenzyme-A to the sn-3 position of 1,2-diacylglycerol ("DAG") to form triacylglyccrol ("TAG") (thereby involved in the terminal step of TAG biosynthesis). DGA1 is associated with membrane and lipid body fractions in plants and fungi, particularly, in oilseeds where it contributes to the storage of carbon used as energy reserves. TAG is believed to be an important chemical for storage of energy in cells. DGA1 is known to regulate TAG structure and direct TAG synthesis.

The DGA1 polynucleotide and polypeptide sequences may be derived from highly oleaginous organisms having very high, native levels of lipid accumulation. (Bioresource Technology 144:360-69 (2013); Progress Lipid Research 52:395-408 (2013); Applied Microbiology & Biotechnology 90:1219-27 (2011); European Journal Lipid Science & Technology 113:1031-51 (2011); Food Technology & Biotechnology 47:215-20 (2009); Advances Applied Microbiology 51:1-51 (2002); Lipids 11:837-44 (1976)). A list of organisms with a reported lipid content of about 50% and higher is shown in Table 1. *R. toruloides* and *L. starkeyi* have the highest lipid content. Among the organisms in Table 1, five have publicly accessible sequence for DGA1, *R. toruloides, L. starkeyi, A. limacinum, A. terreus*, and *C. purpurea* (bolded in Table 1).

TABLE 1

List of oleaginous fungi with reported lipid contents of about 50% and above. Organisms with publicly accessible sequences for a DGA1 gene are in bold.
Fungi with reported high lipid content

Aspergillus terrus
Aurantiochytrium limacinum
Claviceps purpurea
Cryptococcus albidus
Cryptococcus curvatus
Cryptococcus ramirezgomezianus
Cryptococcus terreus
Cryptococcus wieringae
Cunninghamella echinulata
Cunninghamella japonica
Leucosporidiella creatinivora
Lipomyces lipofer
Lipomyces starkeyi
Lipomyces tetrasporus
Mortierella isabellina
Prototheca zopfii
Rhizopus arrhizus
Rhodosporidium babjevae
Rhodosporidium paludigenum
Rhodosporidium toruloides
Rhodotorula glutinis
Rhodotorula mucilaginosa
Tremella enchepala
Trichosporon cutaneum
Trichosporon fermentans Nucleic acid constructs for overexpressing the DGA1 gene were described in U.S. Ser. No. 61/943,664 (hereby incorporated by reference). FIG. 1 shows expression construct pNC243 used for overexpression of the *R. toruloides* DGA1 gene NG66 (SEQ ID No. 6) in *Y. lipolytica*. DGA1 expression constructs were linearized before transformation by PacI/NotI restriction digest (FIG. 1). The linear expression constructs each included expression cassette for DGA1 gene and for NatI gene, used as marker for selection with nourseothricin (NAT).

Nucleic acid constructs for overexpressing the DGA2 gene and/or other diacylglycerol acyltransferases may be created using the methods described above and/or other methods known in the art.

B. Triacylglycerol Lipase Nucleic Acid Molecules and Vectors

Triacylglycerol lipase depletes a cell's triacylglycerol by removing one or more fatty acid chains. Thus, decreasing the net triacylglycerol lipase activity of a cell may increase the cell's triacylglycerol. This decrease may be accomplished by reducing the efficiency of the enzyme, e.g., by mutating amino acids in its active site, or by reducing the expression of the enzyme. For example, a TGL3 knockout mutation will decrease the activity of a triacylglycerol lipase because it prevents the cell from transcribing TGL3.

In some embodiments, the triacylglycerol lipase is TGL3, TGL3/4, or TGL4.

The TGL3 gene in *Y. lipolytica* encodes the triacylglycerol lipase protein TGL3 (SEQ ID No. 19). SEQ ID No. 20 contains the TGL3 nucleotide sequence, 100 upstream nucleotides, and 100 downstream. Thus, the SEQ ID No. 20 nucleotide sequence may be used to design a nucleic acid capable of recombining with a nucleic acid sequence in the native *Y. lipolytica* triacylglycerol lipase gene.

Knockout cassettes SEQ ID Nos. 27 and 28 are capable of recombining with the native TGL3 gene in *Y. lipolytica*. Thus, in some embodiments, the nucleic acids encoded by SEQ ID Nos. 27 and 28 may be used to generate a triacylglycerol lipase knockout mutation in *Y. lipolytica*. SEQ ID Nos. 27 and 28 each contain portions of a hygromycin resistance gene hph. Neither isolated sequence encodes a functional protein, but the two sequences are capable of encoding a functional kinase that confers hygromycin resistance upon successful recombination. Further, neither SEQ ID No. 27 nor SEQ ID No. 28 contains a promoter or terminator, and thus, they rely on homologous recombination with the *Y. lipolytica* TGL3 gene in order for the hph gene to be transcribed and translated. In this way, successfully transformed oleaginous cells may be selected by growing the cells on medium containing hygromycin.

Knockout cassette SEQ ID NO. 27 may be prepared by amplifying a hygromycin resistance gene hph (SEQ ID NO. 22) with primer NP1798 (SEQ ID NO. 23) and primer NP656 (SEQ ID NO. 24). Knockout cassette SEQ ID NO. 28 may be prepared by amplifying a hygromycin resistance gene hph (SEQ ID NO. 22) with primer NP655 (SEQ ID NO. 25) and primer NP1799 (SEQ ID NO. 26).

Different approaches may be used to design nucleic acids that knockout the TGL3 gene in *Y. lipolytica* (Biochimica Biophysica Acta 1831:1486-95 (2013)). The methods disclosed herein and other methods known in the art may be used to knockout triacylglycerol different lipase genes in other species. For example, these methods may be used to reduce the activity of the TGL3 gene of *Arxula adeninivorans* (SEQ ID NO:78), the TGL3/4 gene of *Arxula adeninivorans* (SEQ ID NO:80), and/or the TGL4 gene of *Arxula adeninivorans* (SEQ ID NO:82). Similarly, these methods may be used to reduce the activity of the TGL4 gene in *Y. lipolytica* (SEQ ID NO:88).

C. Transformed Oleaginous Cell

In some embodiments, the transformed oleaginous cell is a prokaryotic cell, such as a bacterial cell. In some embodiments, the cell is a eukaryotic cell, such as a mammalian cell, a yeast cell, a filamentous fungi cell, a protist cell, an algae cell, an avian cell, a plant cell, or an insect cell.

The cell may be selected from the group consisting of *Arxula, Aspergillus, Aurantiochytrium, Candida, Claviceps, Cryptococcus, Cunninghamella, Geotrichum, Hansenula, Kluyveromyces, Kodamaea, Leucosporidiella, Lipomyces, Mortierella, Ogataea, Pichia, Prototheca, Rhizopus, Rhodosporidium, Rhodotorula, Saccharomyes, Schizosaccharomyces, Tremella, Trichosporon, Wickerhamomyces*, and *Yarrowia*.

In some embodiments, the cell is selected from the group of consisting of *Arxula adeninivorans, Aspergillus niger, Aspergillus orzyae, Aspergillus terreus, Aurantiochytrium limacinum, Candida utilis, Claviceps purpurea, Cryptococcus albidus, Cryptococcus curvatus, Cryptococcus ramirezgomezianus, Cryptococcus terreus, Cryptococcus wieringae, Cunninghamella echinulata, Cunninghamella japonica, Geotrichum fermentans, Hansenula polymorpha, Kluyveromyces lactis, Kluyveromyces marxianus, Kodamaea ohmeri, Leucosporidiella creatinivora, Lipomyces lipofer, Lipomyces starkeyi, Lipomyces tetrasporus, Mortierella isabellina, Mortierella alpina, Ogataea polymorpha, Pichia ciferrii, Pichia guilliermondii, Pichia pastoris, Pichia slipites, Prototheca zopfii, Rhizopus arrhizus, Rhodosporidium babjevae, Rhodosporidium toruloides, Rhodosporidium paludigenum, Rhodotorula glutinis, Rhodotorula mucilaginosa, Saccharomyces cerevisiae, Schizosaccharomyces pombe, Tremella enchepala, Trichosporon cutaneum, Trichosporon fermentans, Wickerhamomyces ciferrii*, and *Yarrowia lipolytica*.

In certain embodiments, the transformed oleaginous cell is a high-temperature tolerant yeast cell. In some embodiments the transformed oleaginous cell is *Kluyveromyces marxianus*.

In certain embodiments, the cell is *Yarrowia lipolytica* or *Arxula adeninivorans*.

D. Increasing Diacylglycerol Acyltransferase in a Cell

A protein's activity may be increased by overexpressing the protein. Proteins may be overexpressed in a cell using a variety of genetic modifications. In some embodiments, the genetic modification increases the expression of a native diacylglycerol acyltransferase. A native diacylglycerol acyltransferase may be overexpressed by modifying the upstream transcription regulators of a native diacylglycerol acyltransferase gene, for example, by increasing the expression of a transcription activator or decreasing the expression of a transcription repressor. Alternatively, the promoter of a native diacylglycerol acyltransferase gene may be substituted with a constitutively active or inducible promoter by recombination with an exogenous nucleic acid.

In some embodiments, the genetic modification encodes at least one copy of a diacylglycerol acyltransferase gene. The diacylglycerol acyltransferase gene may be a gene native to the cell or from a different species. In certain embodiments, the diacylglycerol acyltransferase gene is the type II diacylglycerol acyltransferase gene from *Arxula adeninivorans, Aspergillus terreus, Aurantiochytrium limacinum, Claviceps purpurea, Gloeophyllum trabeum, Lipomyces starkeyi, Microbotryum violaceum, Pichia guilliermondii, Phaeodactylum tricornutum, Puccinia graminis, Rhodosporidium diobovatum, Rhodosporidium toruloides, Rhodotorula graminis*, or *Yarrowia lipolytica*. In certain embodiments, the diacylglycerol acyltransferase gene is the type I diacylglycerol acyltransferase gene from *Arxula adeninivorans, Aspergillus terreus, Chaetomium globosum, Claviceps purpurea, Lipomyces starkeyi, Metarhizium acridum, Ophiocordyceps sinensis, Phaeodactylum tricornutum, Pichia guilliermondii, Rhodosporidium toruloides, Rhodotorula graminis, Trichoderma virens*, or *Yarrowia lipolytica*. In certain embodiments, the diacylglycerol acyltransferase gene is the type III diacylglycerol acyltransferase gene from *Ricinus communis* or *Arachis hypogaea*. In certain embodiments, diacylglycerol acyltransferase is overexpressed by transforming a cell with a gene encoding a diacylglycerol acyltransferase gene. The genetic modification may encode one or more than one copy of a diacylglycerol acyltransferase gene. In certain embodiments, the genetic modification encodes at least one copy of the DGA1 protein from *R. toruloides*. In some embodiments, the genetic modification encodes at least one copy of the DGA1 protein from *R. toruloides* and the transformed oleaginous cell is *Y. lipolytica*.

In certain embodiments, the diacylglycerol acyltransferase gene is inheritable to the progeny of a transformed oleaginous cell. In some embodiments, the diacylglycerol acyltransferase gene is inheritable because it resides on a plasmid. In certain embodiments, the diacylglycerol acyltransferase gene is inheritable because it is integrated into the genome of the transformed oleaginous cell.

E. Decreasing Triacylglycerol Lipase Activity in a Cell

In some embodiments, the transformed oleaginous cell comprises a genetic modification that decreases the activity of a native triacylglyccrol lipase. Such genetic modifications may affect a protein that regulates the transcription of a triacylglycerol lipase gene, including modifications that decrease the expression of a transcription activator and/or increase the expression of a transcription repressor. Modifications that affect a regulator protein may both decrease the expression of triacylglycerol lipase and alter other gene expression profiles that shift the cellular equilibrium toward increased triacylglycerol accumulation. Alternatively, the genetic modification may be the introduction of a small interfering RNA, or a nucleic acid that encodes a small interfering RNA. In other embodiments, the genetic modification consists of the homologous recombination of a nucleic acid and the regulatory region of a native triacylglycerol lipase gene, including an operator, promoter, sequences upstream from the promoter, enhancers, and sequences downstream of the gene.

In some embodiments the transformed oleaginous cell comprises a genetic modification consisting of a homologous recombination event. In certain embodiments, the transformed oleaginous cell comprises a genetic modification consisting of a homologous recombination event between a native triacylglycerol lipase gene and a nucleic acid. Thus, the genetic modification deletes the triacylglycerol lipase gene, prevents its transcription, or prevents the transcription of a gene that can be transcribed into a fully-active protein. A homologous recombination event may mutate or delete a portion of a native triacylglycerol lipase gene. For example, the homologous recombination event may mutate one or more residues in the active site of a native triacylglycerol lipase, thereby reducing the efficiency of the lipase or rendering it inactive. Alternatively, the homologous recombination event may affect post-translational modification, folding, stability, or localization within the cell. In certain embodiments, the genetic modification is a triacylglycerol lipase knockout mutation. Knockout mutations are preferable because they eliminate a pathway that depletes a cell's triacylglycerol content, thereby increasing the triacylglycerol content of a cell.

A knockout mutation may delete the triacylglycerol lipase gene. Additionally, the knockout mutation may substitute the triacylglycerol lipase gene with a gene that encodes a different protein. The gene may be operably linked to an exogenous promoter. In certain embodiments, the gene is not linked to an exogenous promoter, and instead, the gene is configured to recombine with the triacylglycerol lipase gene such that the triacylglycerol lipase gene's promoter drives transcription of the gene. Thus, the gene is less likely to be expressed if it randomly integrates into the cell's genome. Methods for creating knockouts are well-known in the art (See, e.g., Fickers et al., J. Microbiological Methods 55:727 (2003)).

In certain embodiments, the genetic modification comprises two homologous recombination events. In the first event, a nucleic acid encoding a portion of a gene recombines with the triacylglycerol lipase gene, and in the second event, a nucleic acid encoding the remaining portion of the gene recombines with the triacylglycerol lipase gene. The two portions of the gene are designed such that neither portion is functional unless they recombine with each other. These two events further reduce the likelihood that the gene can be expressed following random integration events.

In certain embodiments, the gene encodes a dominant selectable marker. Thus, knockout cells may be selected by screening for the marker. In some embodiments, the dominant selectable marker is a drug resistance marker. A drug resistance marker is a dominant selectable marker that, when expressed by a cell, allows the cell to grow and/or survive in the presence of a drug that would normally inhibit cellular growth and/or survival. Cells expressing a drug resistance marker can be selected by growing the cells in the presence of the drug. In some embodiments, the drug resistance marker is an antibiotic resistance marker. In some embodiments, the drug resistance marker confers resistance to a drug selected from the group consisting of Amphotericin B, Candicidin, Filipin, Hamycin, Natamycin, Nystatin, Rimocidin, Bifonazole, Butoconazole. Clotrimazole, Econazole, Fenticonazole, Isoconazole, Ketoconazole, Luliconazole, Miconazole, Omoconazole, Oxiconazole, Sertaconazole, Sulconazole, Tioconazole, Albaconazole, Fluconazole, Isavuconazole, Itraconazole, Posaconazole, Ravuconazole, Terconazole. Voriconazole, Abafungin, Amorolfin, Butenafine, Naftifine, Terbinafine, Anidulafungin, Caspofungin, Micafungin, Benzoic acid, Ciclopirox, Flucytosine, 5-fluorocytosine, Criseofulvin, Haloprogin Polygodial, Tolnaftate, Crystal violet, Amikacin, Gentamicin, Kanamycin, Neomycin, Netilmicin, Tobramycin, Paromomycin, Spectinomycin, Geldanamycin, Herbimycin, Rifaximin, Streptomycin, Loracarbef, Ertapenem, Doripenem, Imipenem, Meropenem, Cefadroxil, Cefazolin, Cefalotin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxinme, Cefriaxone, Cefepime, Ceftaroline fosamil, Ceftobiprole, Teicoplanin, Vancomycin, Telavancin, Clindamycin, Lincomycin, Daptomycin, Azithromycin, Clarithromycin, Dirithromycin, Erythromycin, Roxithromycin, Troleandomycin, Telithromycin, Spiramycin, Aztreonam, Furazolidone, Nitrofurantoin, Linezolid, Posizolid, Radezolid, Torezolid, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Penicillin G, Temocillin, Ticarcillin, clavulanate, sulbactam, tazobactam, clavulanate, Bacitracin, Colistin, Polymyxin B, Ciprofloxacin, Enoxacin, Gatifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin, Mafenide, Sulfacetamide, Sulfadiazine, Silver sulfadiazine, Sulfadimethoxine, Sulfamethizole, Sulfamethoxazole, Sulfanilimide, Sulfasalazine, Sulfisoxazole, Trimethoprim-Sulfamethoxazole, Co-trimoxazole, Sulfonamidochrysoidine, Demeclocycline, Doxycycline, Minocycline, Oxytetracycline, Tetracycline, Clofazimine, Dapsone, Capreomycin, Cycloserine, Ethambutol, Ethionamide, Isoniazid, Pyrazinamide, Rifampicin, Rifabutin, Rifapentine, Streptomycin, Arsphenamine, Chloramphenicol, Fosfomycin, Fusidic acid, Metronidazole, Mupirocin, Platensimycin, Quinupristin, Dalfopristin, Thiamphenicol, Tigecycline, Tinidazole, Trimethoprim, Geneticin, Nourseothricin, Hygromycin, Bleomycin, and Puromycin.

In some embodiments, the dominant selectable marker is a nutritional marker. A nutritional marker is a dominant selectable marker that, when expressed by the cell, enables the cell to grow or survive using one or more particular nutrient sources. Cells expressing a nutritional marker can be selected by growing the cells under limiting nutrient conditions in which cells expressing the nutritional marker can survive and/or grow, but cells lacking the nutrient marker cannot. In some embodiments, the nutritional marker is selected from the group consisting of Orotidine 5-phosphate decarboxylase. Phosphite specific oxidoreductase. Alpha-ketoglutarate-dependent hypophosphite dioxygenase, Alkaline phosphatase, Cyanamide hydratase, Melamine deaminase, Cyanurate amidohydrolase, Biuret hydrolyase, Urea amidolyase, Ammelide aminohydrolase, Guanine deaminase, Phosphodiesterase, Phosphotriesterase, Phosphite hydrogenase, Glycerophosphodiesterase, Parathion hydrolyase, Phosphite dehydrogenase, Dibenzothiophene desulfurization enzyme, Aromatic desulfinase, NADH-dependent FMN reductase, Aminopurine transporter, Hydroxylamine oxidoreductase, Invertase, Beta-glucosidase, Alpha-glucosidase, Beta-galactosidase, Alpha-galactosidase, Amylase, Cellulase, and Pullulonase.

Different approaches may be used to knockout the TGL3 gene in *Y. lipolytica* (See, e.g., Dulermo et al., Biochimica Biophysica Acta 1831:1486 (2013)). The methods disclosed herein and other methods known in the art may be used to knockout different triacylglycerol lipase genes in other species. For example, these methods may be used to knockout the TGL3 gene of *Arxula adeninivorans* (SEQ ID NO:78), the TGL3/4 gene of *Arxula adeninivorans* (SEQ ID NO:80), or the TGL4 gene of *Arxula adeninivorans* (SEQ ID NO:82). Similarly, these methods may be used to knockout the TGL4 gene of *Y. lipolytica* (SEQ ID NO:88).

In some embodiments, a genetic modification decreases the expression of a native triacylglycerol lipase gene by 0.1, 0.2, 0.3, 0.4, 0.5, 0.6, 0.7, 0.8, 0.9, 1, 2, 3, 4, 5, 6, 7, 8, 9, 10, 25, 30, 35, 40, 45, 50, 55, 60, 65, 70, 75, 80, 85, 90, 91, 92, 93, 94, 95, 96, 97, 98, 99, 99.1, 99.2, 99.3, 99.4, 99.5, 99.6, 99.7, 99.8, 99.9, or 100 percent.

In some embodiments, a genetic modification decreases the efficiency of a native triacylglycerol lipase gene by 0.1, 0.2, 0.3, 0.4, 0.5, 0.6, 0.7, 0.8, 0.9, 1, 2, 3, 4, 5, 6, 7, 8, 9, 10, 25, 30, 35, 40, 45, 50, 55, 60, 65, 70, 75, 80, 85, 90, 91, 92, 93, 94, 95, 96, 97, 98, 99, 99.1, 99.2, 99.3, 99.4, 99.5, 99.6, 99.7, 99.8, 99.9, or 100 percent.

In some embodiments, a genetic modification decreases the activity of a native triacylglycerol lipase gene by 0.1, 0.2, 0.3, 0.4, 0.5, 0.6, 0.7, 0.8, 0.9, 1, 2, 3, 4, 5, 6, 7, 8, 9, 10, 25, 30, 35, 40, 45, 50, 55, 60, 65, 70, 75, 80, 85, 90, 91, 92, 93, 94, 95, 96, 97, 98, 99, 99.1, 99.2, 99.3, 99.4, 99.5, 99.6, 99.7, 99.8, 99.9, or 100 percent.

F. Decreasing Triacylglycerol Lipase Activity in a Cell with Concomitant Overexpression of Diacylglycerol Acyltransferase In some embodiments, the transformed oleaginous cell comprises a triacylglycerol lipase knockout mutation and a genetic modification that increase the expression of a native diacylglycerol acyltransferase. In certain embodiments, the transformed oleaginous cell comprises a triacylglycerol lipase knockout mutation and a genetic modification that encodes at least one copy of a diacylglycerol acyltransferase gene that is either native to the cell or from a different species of cell. In other embodiments, a TGL3 gene is disrupted and a DGA1 protein is overexpressed.

In some embodiments, one nucleic acid increases the expression of a native diacylglycerol acyltransferase or encodes at least one copy of a diacylglycerol acyltransferase gene and a second nucleic acid decreases the activity of a triacylglycerol lipase in the cell. In some embodiments the same nucleic acid encodes at least one copy of a diacylglycerol acyltransferase gene and decreases the activity of a triacylglycerol lipase in the cell. For example, the nucleic acid designed to knock out a triacylglycerol lipase gene may also contain a copy of a diacylglycerol acyltransferase gene.

G. Triacylglycerol Production

In certain embodiments, the transformed oleaginous cell are grown in the presence of exogenous fatty acids, glucose, ethanol, xylose, sucrose, starch, starch dextrin, glycerol, cellulose, and/or acetic acid. These substrates may be added during cultivation to increase lipid production. The exogenous fatty acids may include stearate, oleic acid, linoleic acid, γ-linolenic acid, dihomo-γ-linolenic acid, arachidonic acid, α-linolenic acid, stearidonic acid, eicosatetraenoic acid, eicosapenteaenoic acid, docosapentaenoic acid, eicosadienoic acid, and/or eicosatrienoic acid.

In certain embodiments, the present invention relates to a product produced by a modified host cell described herein. In certain embodiments, the product is an oil, lipid, or triacylglycerol. In some embodiments, the product is palmitic acid, palmitoleic acid, stearic acid, oleic acid, or linoleic acid. In certain embodiments, the product is a saturated fatty acid. Thus, the product may be caprylic acid, capric acid, lauric acid, myristic acid, palmitic acid, stearic acid, arachidic acid, behenic acid, lignoceric acid, or cerotic acid. In some embodiments, the product is an unsaturated fatty acid. Thus, the product may be myristoleic acid, palmitoleic acid, sapienic acid, oleic acid, elaidic acid, vaccenic acid, linoleic acid, linoelaidic acid, α-linolenic acid, arachidonic acid, eicosapenteaenoic acid, erucic acid, or docosahexaenoic acid.

In some embodiments, the product comprises an 18-carbon fatty acid. In some embodiments, the product comprises oleic acid, stearic acid, or linoleic acid. For example, the product may be oleic acid.

In some embodiments, the present invention relates to a transformed oleaginous cell comprising a first genetic modification and a second genetic modification. The first genetic modification may increase the activity of a native diacylglycerol acyltransferase. Alternatively, the first genetic modification may encode at least one copy of a diacylglycerol acyltransferase gene native to the oleaginous cell or from a different species. The second genetic modification may decrease the activity of a triacylglycerol lipase in the oleaginous cell.

In some embodiments, the second genetic modification is a triacylglycerol lipase knockout mutation.

In some embodiments, the first genetic modification encodes at least one copy of a diacylglycerol acyltransferase gene native to the oleaginous cell or from a different species. In some embodiments, a diacylglycerol acyltransferase gene is integrated into the genome of the cell.

In some embodiments, the transformed oleaginous cell is selected from the group consisting of algae, bacteria, molds, fungi, plants, and yeasts. In certain embodiments, the transformed oleaginous cell is a yeast. The transformed oleaginous cell may be selected from the group consisting of *Arxula, Aspergillus, Aurantiochytrium, Candida, Claviceps, Cryptococcus, Cunninghamella, Geotrichum, Hansenula, Kluyveromyces, Kodamaea, Leucosporidiella, Lipomyces, Mortierella, Ogataea, Pichia, Prototheca, Rhizopus, Rhodosporidium, Rhodotorula, Saccharomyces, Schizosaccharomyces, Tremella, Trichosporon, Wickerhamomyces,* and *Yarrowia*. In certain embodiments, the transformed oleaginous cell is selected from the group consisting of *Arxula adeninivorans, Aspergillus niger, Aspergillus orzyae, Aspergillus terreus, Aurantiochytrium limacinum, Candida utilis, Claviceps purpurea, Cryptococcus albidus, Cryptococcus curvatus, Cryptococcus ramirezgomezianus, Cryptococcus terreus, Cryptococcus wieringae, Cunninghamella echinulata, Cunninghamella japonica, Geotrichum fermentans, Hansenula polymorpha, Kluyveromyces lactis, Kluyveromyces marxianus, Kodamaea ohmeri, Leucosporidiella creatinivora, Lipomyces lipofer, Lipomyces starkeyi, Lipomyces tetrasporus, Mortierella isabellina, Mortierella alpina, Ogataea polymorpha, Pichia ciferrii, Pichia guilliermondii, Pichia pastoris, Pichia stipites, Prototheca zopfii, Rhizopus arrhizus, Rhodosporidium babjevae, Rhodosporidium toruloides, Rhodosporidium paludigenum, Rhodotorula glutinis, Rhodotorula mucilaginosa, Saccharomyces cerevisiae, Schizosaccharomyces pombe, Tremella enchepala, Trichosporon cutaneum, Trichosporon fermentans, Wickerhamomyces ciferrii,* and *Yarrowia lipolytica*. In other embodiments, the transformed oleaginous cell is *Yarrowia lipolytica* or *Arxula adeninivorans*.

In some embodiments, the diacylglycerol acyltransferase gene is a type II diacylglycerol acyltransferase gene. The diacylglycerol acyltransferase gene may be a type II diacylglycerol acyltransferase gene from *Arxula adeninivorans, Aspergillus terreus, Aurantiochytrium limacinum, Claviceps purpurea, Gloeophyllum trabeum, Lipomyces starkeyi, Microbotryum violaceum, Pichia guilliermondii, Phaeodactylum tricornutum, Puccinia graminis, Rhodosporidium diobovatum, Rhodosporidium toruloides, Rhodotorula graminis,* or *Yarrowia lipolytica*.

In some embodiments, the diacylglycerol acyltransferase gene is a type I diacylglycerol acyltransferase gene. The diacylglycerol acyltransferase gene may be a type I diacylglycerol acyltransferase gene from *Arxula adeninivorans, Aspergillus terreus, Chaetomium globosum, Claviceps purpurea, Lipomyces starkeyi, Metarhizium acridum, Ophiocordyceps sinensis, Phaeodactylum tricornutum, Pichia guilliermondii, Rhodosporidium toruloides, Rhodotorula graminis, Trichoderma virens,* or *Yarrowia lipolytica*.

In some embodiments, the diacylglycerol acyltransferase gene is a type III diacylglycerol acyltransferase gene. The diacylglycerol acyltransferase gene may be a type III diacylglycerol acyltransferase gene from *Ricinus communis* or *Arachis hypogaea*.

In some embodiments, the triacylglycerol lipase is TGL3, TGL3/4, or TGL4.

In some embodiments, the present invention relates to a product derived from a transformed oleaginous cell. In certain embodiments, the product is an oil, lipid, or triacylglycerol.

In some embodiments, the present invention relates to a method of increasing the lipid content of a cell, comprising transforming a parent cell with a first nucleic acid and a second nucleic acid. The first nucleic acid may increase the activity of a native diacylglycerol acyltransferase or comprise a diacylglycerol acyltransferase gene. The second nucleic acid may decrease the activity of a triacylglycerol lipase. The first nucleic acid and second nucleic acid may be the same. Thus, in some embodiments, the present invention relates to a method of increasing the lipid content of a cell comprising transforming a parent cell with a nucleic acid, wherein the nucleic acid decreases the activity of a triacylglycerol lipase in the cell and either comprises a diacylglycerol acyltransferase gene or increases the activity of a native diacylglycerol acyltransferase.

In some embodiments, the present invention relates to a method of increasing the triacylglycerol content of a cell, comprising providing a cell and growing the cell. The cell may comprise a first genetic modification and a second genetic modification. The first genetic modification may increase the activity of a native diacylglycerol acyltransferase or encode at least one copy of a diacylglycerol acyltransferase gene either native to the oleaginous cell or from a different species. The second genetic modification may decrease the activity of a triacylglycerol lipase in the cell. The cell may be grown under conditions whereby the first genetic modification is expressed, thereby producing a triacylglycerol. In some embodiments, the triacylglycerol is recovered.

In some embodiments, the first nucleic acid comprises a diacylglycerol acyltransferase gene. The diacylglycerol acyltransferase gene may encode a type I diacylglycerol acyltransferase polypeptide, a type II diacylglycerol acyltransferase polypeptide, or a type III diacylglycerol acyltransferase polypeptide.

In some embodiments, the diacylglycerol acyltransferase gene comprises a nucleotide sequence set forth in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 30, SEQ ID NO: 32, SEQ ID NO: 34, SEQ ID NO: 36, SEQ ID NO: 38, SEQ ID NO: 40, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 84, or SEQ ID NO: 86, or a complement of any one of them.

In some embodiments, the diacylglycerol acyltransferase gene comprises a nucleotide sequence having at least 70%, 75%, 80%, 85%, 90%, 95%, 96%, 97%, 98%, or 99% sequence identity to a nucleotide sequence set forth in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 30, SEQ ID NO: 32, SEQ ID NO: 34, SEQ ID NO: 36, SEQ ID NO: 38, SEQ ID NO: 40, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 84, or SEQ ID NO: 86, or a complement of any one of them.

In some embodiments, the diacylglycerol acyltransferase polypeptide comprises an amino acid sequence set forth in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61 SEQ ID NO: 29, SEQ ID NO: 31, SEQ ID NO: 33, SEQ ID NO: 35, SEQ ID NO: 37, SEQ ID NO: 39, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 83, or SEQ ID NO: 85, or a biologically-active portion of any one of them.

In some embodiments, the diacylglycerol acyltransferase polypeptide comprises an amino acid sequence having at least 80%, 85%, 90%, 95%, 96%, 97%, 98%, or 99% sequence identity to an amino acid sequence forth in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61; SEQ ID NO: 29, SEQ ID NO: 31, SEQ ID NO: 33, SEQ ID NO: 35, SEQ ID NO: 37, SEQ ID NO: 39, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 83, or SEQ ID NO: 85, or a biologically-active portion of any one of them.

In some embodiments, the second nucleic acid is capable of recombining with a nucleic acid sequence in a triacylglycerol lipase gene and/or a nucleic acid sequence in the regulatory region of a triacylglyccrol lipase gene. In certain embodiments, the second nucleic acid is capable of recombining with a nucleic acid sequence in a TGL3, TGL3/4, or TGL4 gene and/or a nucleic acid sequence in the regulatory region of a TGL3, TGL3/4, or TGL4 gene. The second nucleic acid may comprise a gene encoding a protein or a portion of a protein. In certain embodiments, the second nucleic acid comprises a gene encoding a protein that confers resistance to a drug. In other embodiments, the second nucleic acid comprises a gene encoding a protein that enables the cell to grow or proliferate more quickly on one or more particular nutrient sources than a native organism of the same species.

The present description is further illustrated by the following examples, which should not be construed as limiting in any way. The contents of all cited references (including literature references, issued patents, published patent applications and GenBank Accession numbers as cited throughout this application) are hereby expressly incorporated by reference. When definitions of terms in documents that are incorporated by reference herein conflict with those used herein, the definitions used herein govern.

EXEMPLIFICATION

Example 1: Method to Overexpress DGA in *Y. lipolytica*

Nucleic acid constructs for overexpressing the DGA1 gene were described in U.S. Ser. No. 61/943,664 (hereby incorporated by reference). FIG. 1 shows expression construct pNC243 used for overexpression of the *R. toruloides* DGA1 gene NG66 (SEQ ID No. 6) in *Y. lipolytica*. DGA1 expression constructs were linearized before transformation by a PacI/NotI restriction digest. The linear expression constructs each included an expression cassette for the DGA1 gene and for the Nat1 gene, used as a marker for selection with nourseothricin (NAT).

DGA1 expression constructs were randomly integrated into the genome of *Y. lipolytica* strain NS18 (obtained from ARS Culture Collection, NRRL#YB 392) using a transformation protocol as described in Chen (Applied Microbiology & Biotechnology 48:232-35 (1997)). Transformants were selected on YPD plates with 500 µg/mL NAT and screened for the ability to accumulate lipids by a fluorescent staining lipid assay as described below. For each expression construct, eight transformants were analysed.

For most constructs, there was significant colony variation between the transformants, likely due to the lack of a functional DGA1 expression cassette in cells that only obtained a functional Nat1 cassette, or due to a negative effect of the site of DGA1 integration on DGA1 expression. Nevertheless, all transformants had a significant increase in lipid content.

Overexpression of native *Y. lipolytica* DGA1 (NG15) under a strong promoter increased lipid content as measured by cell fluorescence by about 2-fold compared to the parental strain NS18. Transformants that demonstrated the highest fluorescence (about 3-fold higher compared to NS18) were generated by the overexpression of *R. toruloides* DGA1 (NG66, NG67) and *L. starkeyi* DGA1 (NG68).

In certain experiments, the effect of native *R. toruloides* DGA1 (NG49) overexpression on lipid production in *Y. lipolytica* was not as high as the effect of synthetic versions of *R. toruloides* DGA1 genes that did not contain introns. This result may indicate that the gene splicing of the *R. toruloides* DGA1 gene in *Y. lipolytica* was not very efficient. In certain experiments, codon optimization of the *R. toruloides* DGA1 gene for expression in *Y. lipolytica* did not have a positive effect on lipid production.

In order to select strains with the highest lipid production level, *Y. lipolytica* strain NS18 transformants expressing NG15 (*Y. lipolytica* DGA1) or NG66 (*R. toruloides* DGA1) were screened. For NG15, about 50 colonies were screened by lipid assay for the highest lipid accumulation, and the best transformant was named NS249. For NG66, 80 colonies were screened and the 8 best colonies were selected for further analysis. Strain NS249 and the 8 selected NG66 transformants were grown in shake flasks and analysed by the lipid assay for lipid content and by HPLC for glucose consumption. *Y. lipolytica* strains overexpressing *R. toruloides* DGA1 have significantly higher lipid content than *Y. lipolytica* strains with native *Y. lipolytica* DGA1 gene expressed under the same promoter as *R. toruloides* DGA1. At the same time, NG66 transformants had significantly less glucose left in the media, demonstrating that NG66 was more efficient in converting glucose to lipids. The difference in efficiency between two DGA1 genes may be attributed to either a higher level of expression of *R. toruloides* DGA1 in *Y. lipolytica* or a higher level of *R. toruloides* DGA1 specific activity, or both. One of the best performing transformants with an integrated NG66 gene was named NS281.

Example 2: Method to Knockout Triacylglycerol Lipase Knockout Gene in *Y. lipolytica*

In order to test the idea that combining DGA1 overexpression with a TGL3 deletion leads to higher lipid accumulation in *Y. lipolytica*, we deleted TGL3 in *Y. lipolytica* wild-type strain NS18 (obtained from NRLL#YB-392) and its DGA1 overexpressing derivative NS281. NS281 overexpresses the DGA1 gene from *Rhodosporidium toruloides* as described above. The *Y. lipolytica* TGL3 gene (YALI0D17534g, SEQ ID NO: 20) was deleted as follows: A two-fragment deletion cassette was amplified by PCR from a plasmid containing the hygromycin resistance gene ("hph," SEQ ID NO: 22) using primer pairs NP1798-NP656 and NP655-NP1799 (SEQ ID NOs: 23-26). The resulting PCR fragments (SEQ ID NOs: 27 & 28) were co-transformed into NS18 and NS281 according to the protocol developed in U.S. Ser. No. 61/819,746 (hereby incorporated by reference). The omission of a promoter and terminator in the hph cassette and the splitting of the hph coding sequence into two PCR fragments reduce the probability that random integration of these pieces will confer hygromycin resistance. The hph gene should only be expressed if it integrates at the TGL3 locus by homologous recombination so that the TGL3 promoter and terminator can direct its transcription. Hygromycin resistant colonies were screened by PCR to confirm the absence of TGL3 and the presence of a tgl3::hyg specific product. Deletion of TGL3 in NS18 resulted in strain NS421. Deletion of TGL3 in NS281 resulted in strain NS377.

Example 3: TGL3 Knockouts that Overexpress DGA1 Accumulate More Lipid than TGL3 Knockouts Alone NS421, which contains the TGL3 knockout, and NS377, which contains the TGL3 deletion and also overexpresses *R. toruloides* DGA1, were grown in a 24-well plate in limiting nitrogen conditions in order to promote lipid accumulation.

Specifically, each well of an autoclaved, 24-well plate was filled with 1.5 mL of filter-sterilized media containing 0.5 g/L urea, 1.5 g/l yeast extract, 0.85 g/L casamino acids, 1.7 g/L YNB (without amino acids and ammonium sulfate), 100 g/L glucose, and 5.11 g/L potassium hydrogen phthalate (25 mM). Yeast strains that had been incubated for 1-2 days on YPD-agar plates at 30° C. were used to inoculate each well. The 24-well plate was covered with a porous cover and incubated at 30° C., 70-90% humidity, and 900 rpm in an Infors Multitron ATR shaker. After 96 hours, 20 µL of 100% ethanol was added to 20 µL of cells in an analytical microplate and incubated at 4° C. for 30 minutes. 20 µL of cell/ethanol mix was then added to 80 µl of a pre-mixed solution containing 50 µL 1 M potassium iodide, 1 mM µL Bodipy 493/503, 0.5 µL 100% DMSO, 1.5 µL 60% PEG 4000, and 27 µL water in a Costar 96-well, black, clear-bottom plate and covered with a transparent seal. Bodipy fluorescence was monitored with a SpectraMax M2 spectrophotometer (Molecular Devices) kinetic assay at 30° C., and normalized by dividing fluorescence by absorbance at 600 nm. Data was averaged in triplicate growth experiments.

Figure 2:
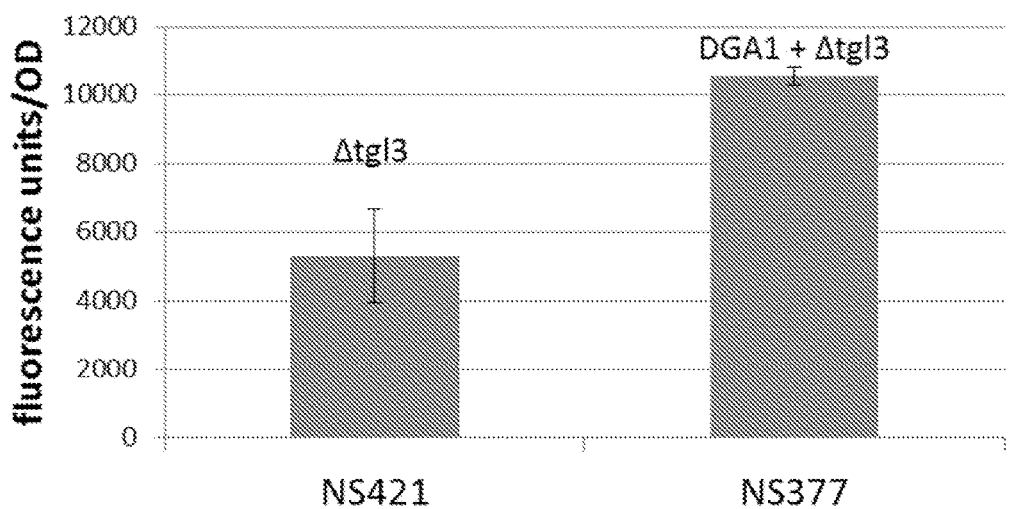
FIG. 2 is a graph depicting results from a fluorescence-based lipid assay for *Y. lipolytica* strain NS421, which is a triacylglycerol lipase knockout strain, and *Y. lipolytica* strain NS377, which is a triacylglycerol lipase knockout strain that overexpresses the diacylglycerol acyltransferase DGA1 gene NG66.

NS377 accumulated approximately double the amount of lipid as NS421 showing that deletion of TGL3 in combination with DGA1 overexpression increases a cell's lipid content relative to a TGL3 deletion alone (FIG. 2).

Figure 3:
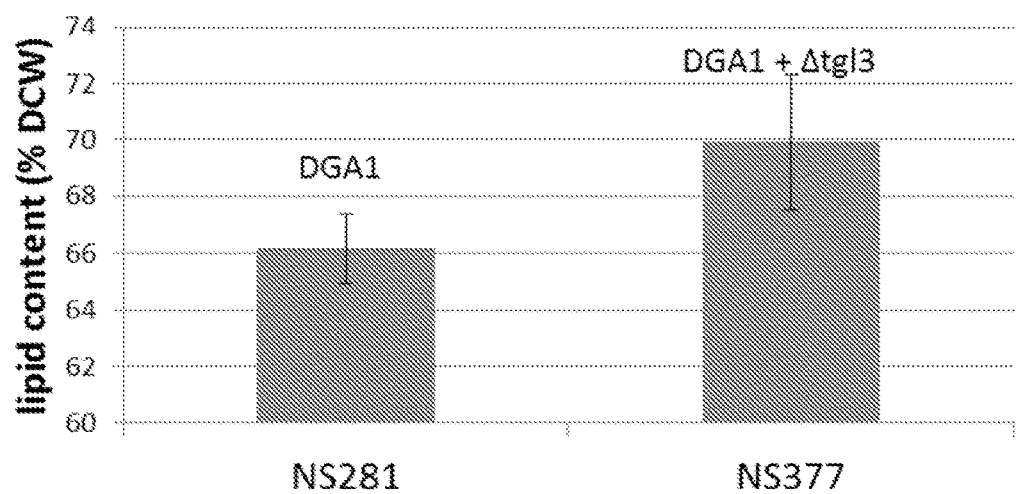
FIG. 3 is a graph depicting results from a gas chromatography analysis of *Y. lipolytica* strain NS281, which overexpresses the diacylglycerol acyltransferase DGA1 gene NG66, and *Y. lipolytica* strain NS377, containing a triacylglyccrol lipase knockout and overexpressing the diacylglycerol acyltransferase DGA1 gene NG66.

Example 4: Cells that Overexpress DGA1 and Contain a TGL3 Deletion Accumulate More TAGs than Cells that Overexpress DGA1 but have No TGL3 Modification NS281, which overexpresses *R. toruloides* DGA1, and NS377, which contains the TGL3 deletion and also overexpresses *R. toruloides* DGA1, were grown in 1-liter bioreactors using a high cell density fed-batch glucose process. After 118 hours, the cells were analyzed by gas chromatography to measure lipid content as a percentage of dry cell weight. Triplicate chromatography measurements were averaged for the same sample. NS377 reached approximately 4% higher lipid content than NS281, showing that deletion of TGL3 in combination with DGA1 overexpression yields better results than DGA1 overexpression alone (FIG. 3).

Example 5: Cells Comprising Genetic Modifications that Encode a Diacylglycerol Acyltransferase and Decrease the Activity of a Triacylglycerol Lipase Accumulate More TAGs In order to test the idea that combining DGA1 and DGA2 overexpression with TGL3 deletion leads to higher lipid accumulation in *Y. lipolytica*, DGA2 from *Claviceps purpurea* was overexpressed in strain NS377. Strain NS377 contains a deletion of TGL3 and overexpresses DGA1 from *Rhodosporidium toruloides* as described in Example 4. DGA2 from *Claviceps purpurea* was selected based on prior experiments that demonstrate that this gene increases the lipid content of *Y. lipolytica* in combination with DGA1 from *Rhodosporidium toruloides* (U.S. Ser. No. 62/004,502, incorporated by reference).

Figure 4:
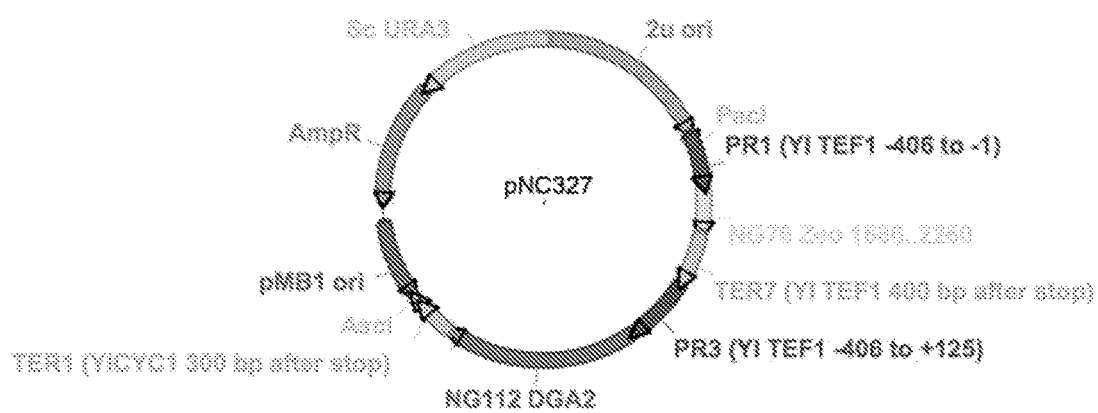
FIG. 4 depicts a map of the pNC327 construct used to overexpress the NG112 gene (*C. purpurea* DGA2) in *Y. lipolytica*. Vector pNC327 was linearized by a PacI/AscI restriction digest before transformation. "2u ori" denotes the *S. cerevisiae* origin of replication from the 2 μm circle plasmid; "pMB1 ori" denotes the *E. coli* pMB1 origin of replication from the pBR322 plasmid; "AmpR" denotes the bla gene used as a marker for selection with ampicillin; "PR3" denotes the *Y. lipolytica* TEF1 promoter-406 to +125; "NG112" denotes the *C. purpurea* DGA2 gene synthetized by GenScript; "TER1" denotes the *Y. lipolytica* CYC1 terminator 300 bp after stop; "PR1" denotes the *Y. lipolytica* TEF1 promoter-406 to -1; "NG76" denotes the *Streptoalloteichus hindtusamus* BLE gene used as marker for selection with Zeocin; "TER7" denotes the *Y. lipolytica* TEF1 terminator 400 bp after stop; and "Sc URA3" denotes the *S. cerevisiae* URA3 auxotrophic marker for selection in yeast.

FIG. 4 shows the map of pNC327, the expression construct used to overexpress *C. purpurea* DGA2 in NS377. The construct was linearized prior to transformation with a PacI/AscI restriction digest. The linear expression construct included an expression cassette for the *C. purpurea* DGA2 gene and for the BLE gene used as a marker for selection with Zeocin (ZEO). Transformants were analyzed by the fluorescent lipid assay, and the top lipid producer was designated NS432.

Figure 5:
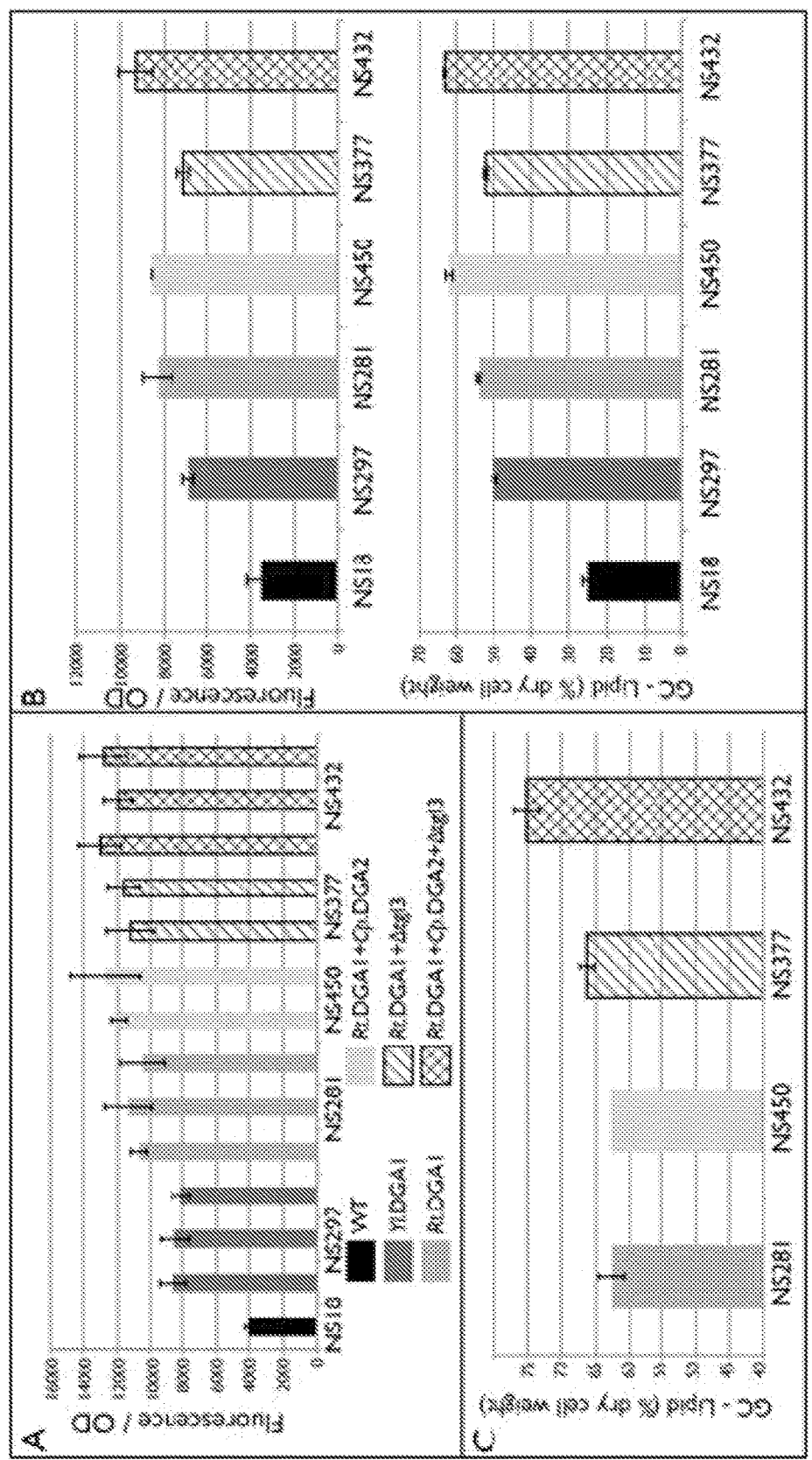
FIG. 5 comprises three panels, labeled pane (A), (B), and (C). The figure depicts lipid accumulation measured by a fluorescence-based assay or a percentage of the dry cell weight as determined by gas chromatography for *Yarrowia lipolytica* strains NS297, NS281, NS450, NS377, and NS432. NS297 expresses an additional copy of *Y. lipolytica* DGA1; NS281 expresses *Rhodosporidium toruloides* DGA1; NS450 expresses *R. toruloides* DGA1 and *Claviceps purpurea* DGA2; NS377 expresses *R. toruloides*, and carries a deletion of *Y. lipolytica* TGL3; NS432 expresses *R. toruloides* DGA1 and *C. purpurea* DGA2 and carries a deletion of *Y. lipolytica* TGL3. In panel (A), strains were analyzed by fluorescence assay after 96 hours of fermentation in a 48-well plate where two or three transformants were analyzed for each construct. In panel (B), strains were analyzed by fluorescence assay and gas chromatography after 96 hours of fermentation in 50-mL flasks. In panel (C), strains were analyzed by gas chromatography after 140 hours of fermentation in 1-L bioreactors. Data for NS281, NS377, and NS432 are averages obtained from duplicate bioreactor fermentations. Data for NS450 represents the value obtained from a single bioreactor fermentation.

The lipid production of strains NS297, NS281, NS450, NS377, and NS432 were compared. A subset of these strains were either grown using a batch glucose process (in 48-well plates or 50-mL flasks) or using a high cell density fed-batch glucose process (in 1-L bioreactors). Lipid content was analyzed by fluorescence assay or gas chromatography, and strain NS432 was found to have a higher lipid content than its parent strain NS377 and the strains without the TGL3 knockout (FIG. 5). These results demonstrate the advantage of DGA1 and DGA2 overexpression in a TGL3 knockout.

INCORPORATION BY REFERENCE

All of the U.S. patents, U.S. patent application publications, foreign patents, foreign patent publications, and non-patent literature cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A transformed oleaginous cell, comprising a first genetic modification, wherein said first genetic modification comprises at least one extra copy of a heterologous diacylglycerol acyltransferase gene from, *Rhodosporidium toruloides*; and a second genetic modification, wherein said second genetic modification is a triacylglycerol lipase knockout mutation in the oleaginous cell, wherein said transformed oleaginous cell accumulates more lipid than a non-transformed cell of the same species.

2. The transformed oleaginous cell of claim 1, wherein said triacylglycerol lipase is TGL3.

3. The transformed oleaginous cell of claim 1, wherein said first genetic modification encodes at least one copy of a diacylglycerol acyltransferase gene native to the oleaginous cell or from a different species.

4. The transformed oleaginous cell of claim 3, wherein said diacylglycerol acyltransferase gene is a type I diacylglycerol acyltransferase gene, type II diacylglycerol acyltransferase gene, or type III diacylglycerol acyltransferase gene.

5. The transformed oleaginous cell of claim 4, wherein said diacylglycerol acyltransferase gene is a type I diacylglycerol acyltransferase gene from *Yarrowia lipolytica*.

6. The transformed oleaginous cell of claim 4, wherein said diacylglycerol acyltransferase gene is a type III diacylglycerol acyltransferase gene from *Ricinus communis* or *Arachis hypogaea*.

7. The transformed oleaginous cell of claim 4, wherein said at least one copy of a diacylglycerol acyltransferase gene is integrated into the genome of said cell.

8. The transformed oleaginous cell of claim 1, wherein said cell is selected from the group consisting of algae, bacteria, molds, fungi, plants, and yeasts.

9. The transformed oleaginous cell of claim 8, wherein said cell is selected from the group consisting of *Arxula, Saccharomyces* and *Yarrowia*.

10. The transformed oleaginous cell of claim 9, wherein said cell is selected from the group consisting of *Arxula adenintvorans, Saccharomyces cerevisiae*, and *Yarrowia lipolytica*.

11. The transformed of oleaginous cell of claim 1, wherein said diacylglycerol acyltransferase gene comprises SEQ ID NO:6.

12. The transformed oleaginous cell of claim 1, wherein said diacylglycerol acyltransferase gene is a type II diacylglycerol acyltransferase.

13. The transformed oleaginous cell of claim 1, wherein said diacylglycerol acyltransferase gene is a type I diacylglycerol acyltransferase.

* * * * *